(12) United States Patent
Lihme et al.

(10) Patent No.: US 12,274,279 B2
(45) Date of Patent: Apr. 15, 2025

(54) METHODS FOR ISOLATING COMPOUNDS

(71) Applicant: DUYNIE HOLDING B.V., Alphen aan den Rijn (NL)

(72) Inventors: Allan Otto Fog Lihme, Farum (DK); Marie Bendix Hansen, Frederiksberg (DK); Bodil Ingrid Kjaer Lindved, Espergaerde (DK)

(73) Assignee: DUYNIE HOLDING B.V., Alphen aan den Rijn (NL)

( * ) Notice: Subject to any disclaimer, the term of this patent is extended or adjusted under 35 U.S.C. 154(b) by 112 days.

(21) Appl. No.: 18/079,984

(22) Filed: Dec. 13, 2022

(65) Prior Publication Data

US 2023/0111991 A1 Apr. 13, 2023

Related U.S. Application Data

(63) Continuation of application No. 16/347,466, filed as application No. PCT/DK2017/050365 on Nov. 7, 2017, now Pat. No. 11,553,724.

(30) Foreign Application Priority Data

| Nov. 7, 2016 | (DK) | PA 2016 70871 |
| Jun. 30, 2017 | (DK) | PA 2017 70532 |
| Aug. 11, 2017 | (DK) | PA 2017 70611 |
| Sep. 11, 2017 | (DK) | PA 2017 70677 |

(51) Int. Cl.

| C07K 1/30 | (2006.01) |
| A23J 1/00 | (2006.01) |
| A23K 10/35 | (2016.01) |
| A23L 2/02 | (2006.01) |
| A23L 2/70 | (2006.01) |
| A23L 5/20 | (2016.01) |
| A23L 19/12 | (2016.01) |
| B01D 61/14 | (2006.01) |
| C07K 1/32 | (2006.01) |
| C07K 14/415 | (2006.01) |

(52) U.S. Cl.
CPC .............. *A23J 1/006* (2013.01); *A23K 10/35* (2016.05); *A23L 2/02* (2013.01); *A23L 2/70* (2013.01); *A23L 5/20* (2016.08); *A23L 5/276* (2016.08); *A23L 19/12* (2016.08); *B01D 61/145* (2013.01); *C07K 1/30* (2013.01); *C07K 1/32* (2013.01); *C07K 14/415* (2013.01); *A23V 2002/00* (2013.01); *B01D 2311/12* (2013.01); *B01D 2311/2642* (2013.01)

(58) Field of Classification Search
CPC . C07K 1/30; A23L 1/006; A23L 5/276; A23L 19/22; A23K 10/35
See application file for complete search history.

(56) References Cited

U.S. PATENT DOCUMENTS

2003/0077265 A1 4/2003 Ausich et al.

FOREIGN PATENT DOCUMENTS

| WO | WO-2008/056977 A1 | 5/2008 |
| WO | WO-2008/069650 A1 | 6/2008 |
| WO | WO-2016/036243 A1 | 3/2016 |

OTHER PUBLICATIONS

Kong et al., Recovering proteins from potato juice by complexation with natural polyelectrolytes, International Journal of Food Science and Technology, 50:2160-2167 (2015).
May et al., Aqueous dissolution, solubilities and thermodynamic stabilities of common aluminosilicate clay minerals: Kaolinite and smectites, Geochimica et Cosmochimica Acta, 50:1667-1677 (1986).
Ralla et al., Separation of patatins and protease inhibitors from potato fruit juice with clay minerals as cation exchangers, Journal of Separation Science, 35:1596-1602 (2012).
Straetkvern et al., Recovery of Native Potato Protein Comparing Expanded Bed Absorption and Ultrafiltration, Food Bioprocess Technol., 5:1939-1949 (2011).
Van Koningsveld et al., The solubility of potato proteins from industrial potato fruit juice as influenced by pH and various additives, Journal of the Science of Food and Agriculture, 82:134-142 (2001).
Waglay & Karboune, Potato Proteins: Functional Food Ingredients: Chapter 4; Advances in Potato Chemistry and Technology, pp. 75-104 (Aug. 2016).

(Continued)

*Primary Examiner* — Sikarl A Witherspoon
(74) *Attorney, Agent, or Firm* — MARSHALL, GERSTEIN & BORUN LLP

(57) ABSTRACT

The present invention in its broadest aspect relates to a method for reducing glycoalkaloid content and turbidity of an aqueous phase comprising compounds selected from two or more of PA, PI, PPO, LipO, pectin, lipid, glycoalkaloid and phenolic compounds of which at least one compound is selected from PA, PT, LipO and PPO; a) providing an aqueous phase comprising compounds selected from two or more of PA, PI, PPO, LipO, pectin, lipid, glycoalkaloid and phenolic compounds of which at least one compound is selected from PA, PT, LipO and PPO; and b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1; and thereby obtaining an aqueous phase having reduced glycoalkaloid content and turbidity compared to an untreated aqueous phase.

20 Claims, 22 Drawing Sheets

(56) References Cited

OTHER PUBLICATIONS

Zwijnenberg et al., Native protein recovery from potato fruit juice by ultrafiltration, Desalination, 144:331-334 (2002).
International Search Report for PCT/DK2017/050365 dated Jan. 25, 2018.
Written Opinion for PCT/DK2017/050365 dated Jan. 25, 2018.

METHODS FOR ISOLATING COMPOUNDS

CROSS REFERENCE TO RELATED APPLICATIONS AND INCORPORATION BY REFERENCE

This application is a continuation of U.S. patent application Ser. No. 16/347,466, filed May 3, 2019, which in turn is a U.S. national stage of International Application No. PCT/DK2017/050365, filed Nov. 7, 2017, which claims the benefit of Danish Patent Application No. 2016 70871, filed Nov. 7, 2016, Danish Patent Application No. 2017 70532, filed Jun. 30, 2017, Danish Patent Application No. 2017 70611, filed Aug. 11, 2017, and Danish Patent Application No. 2017 70677, filed Sep. 11, 2017, the disclosures of which are hereby incorporated by reference.

TECHNICAL FIELD OF THE INVENTION

The present invention relates to methods for isolating compounds, particularly proteins, from materials containing such compounds, particularly plant materials, to the isolated compounds, to compositions comprising the isolated compounds and to use and application of the isolated compounds.

BACKGROUND OF THE INVENTION

Compounds such as proteins and metabolites comprised in plants are valuable and useful in many different applications such as nutrition, medical treatments, cosmetics and acceptable process aids for industrial manufacture of the same. Particularly, such proteins and metabolites in significant crop plants, such as potatoes, are interesting and become even more valuable and useful in isolated form. Potatoes, for example, contain useful patatins and protease inhibitors which are desirable to use in isolated and more pure forms.

Kong et al. (*Recovering proteins from potato juice by complexation with natural polyelectrolytes*; International Journal of Food Science and Technology 2015, 50, 2160-2167) relates to characterization of potato proteins and their protein-polyelectrolyte complexes.

Waglay & Karboune (Potato Proteins: Functional Food Ingredients; Chapter 4; Advances in Potato Chemistry and Technology, 08 2016) disclose potato proteins prepared by various methods including thermal coagulation, acidic precipitation, precipitation with salt, ethanol, ammonium sulfate or CMC, anion-exchange chromatography or size exclusion separation.

Gerrit A Van Köningsveld (Journal of the Science of Food and Agriculture, vol 82, pp 134-142, 2001) disclose the solubility of potato proteins as influenced by pH and various additives.

However, many plants, including potatoes, also contain compounds that are undesirable or even poisonous in some applications. Particularly, potatoes (belonging to the night shade family) contain several compounds which are undesired for some applications, while useful in other applications. Patatins and protease inhibitors are useful in nutrition and nutraceutical application, while glycoalkaloids (toxic), lipoxygenase (rancidify fats/oils), polyphenol oxidase (oxidizes and tans food stuff) or phenolic compounds are not desired in nutrition and nutraceutical applications. On the other hand, isolated glycoalkaloids are useful in certain cosmetic or pharmaceutical applications. Accordingly, there is a need for methods for separating and/or isolating functional plant compounds to be used in industrial applications.

Isolation of highly purified proteins from plant extracts is a demanding task due to the extremely complex and reactive compositions achieved when the plant tissue is mechanically and/or chemically disrupted. Highly selective separation methods, such as adsorption chromatography, may relatively straightforward be applied to specifically adsorb and release the proteins free from contaminants but such methods have proven too costly in many applications targeting proteins for e.g. food applications. Other methods, like membrane filtration and classical separation of proteins by isoelectric precipitation or precipitation by the use of lyotropic salts (salting put) and organic solvents, have proven to be too unspecific when applied to crude plant extracts.

The increasing need for sustainable production of food and feed materials further emphasize the complexity involved in designing industrial scale processing methods that preserves the value of any given raw material and the product and side streams resulting from processing it. This means an increased need to avoid product losses and to avoid processing methods that destroy the value of the other components in the raw material such that they may be worked up as valuable products too and thereby increase the sustainability of the entire value chain. This is in contrast to many prior art processes that may focus mainly on one product to be produced from the raw material and where the potential value of side streams is neglected.

US 2003/0077265 discloses a method to produce potato protease inhibitors comprising extracting potatoes with aqueous organic acids and salts combined with heat denaturation and removal of undesired proteins followed by ultrafiltration to concentrate and diafiltrate the protease inhibitors. However, this method cannot be applied to the potato fruit juice being produced as a large volume side stream during the manufacture of potato starch. Further this method destroys the value of the major part of the potato by the use of e.g. formic acid, salts and heating directly to the potatoes.

Especially in the field of potato protein isolation there has for many years been attempted many different techniques to economically produce food grade proteins out of the fruit juice released during the production of potato starches. It has, however, been difficult to achieve the quality needed for food proteins while at the same time applying an industrially applicable, robust and profitable processing scheme. For example, according to several scientific reports (e.g. Straetkvern K O & Schwarz J G (2012) Recovery of Native Potato Protein Comparing Expanded Bed Adsorption and Ultrafiltration. Food and Bioprocess Technology. 5(5), 1939-1949 and Zwijnenberg H J, Kemperman A J B, Boerrigter M E, Lotz M, Dijksterhuis J F, Poulsen P E & Koops G H (2002) Native protein recovery from potato fruit juice by ultrafiltration. Desalination. 144(1-3), 331-334) ultrafiltration has low selectivity and only poorly separate polyphenols and brown polyphenol complexes from proteins thus giving a powder with a final brown hue and higher content of chlorogenic acids, and in addition it is often encountered with membrane concentration of potato fruit juice that fouling of the membranes lead to low flux rates, low system productivity and a shorter membrane lifetime.

Thus, there is a strong need to develop new and improved methods that solve these issues.

SUMMARY OF THE INVENTION

The present invention in its broadest aspect relates to a method for reducing turbidity of an aqueous phase comprising compounds selected from two or more of PA, PI, PPO, LipO, pectin, lipid, glycoalkaloid and phenolic compounds of which at least one compound is selected from PA, PI, LipO and PPO;

a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) contacting the aqueous phase with a soluble silicate at a pH in the range of 3-10 and optionally, a divalent or trivalent metal ion allowing formation of an insoluble precipitate comprising said silicate and one or more the compounds selected from LipO, PPO, pectin, lipid, glycoalkaloid and phenolic compounds, and optionally, a divalent or trivalent metal ion, said insoluble precipitate is subsequently removed from the aqueous phase by physical means;

thereby obtaining an aqueous phase having reduced turbidity compared to an untreated aqueous phase.

The inventors of the present invention have also developed new methods for separating and isolating functional plant compounds, methods which are unexpectedly applicable and useful in industrial scale processing of plant materials. Accordingly, the present invention provides in a first aspect a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, glycoalkaloid and phenolic compounds said method comprising:

a) providing an aqueous phase comprising compounds selected from two or more of PA, PI, PPO, LipO, glycoalkaloid and phenolic compounds of which at least one compound is selected from PA, PI, LipO and PPO;

b) contacting the aqueous phase with a mobile solubilized ligand at physico-chemical conditions allowing formation of a complex between the ligand and the compounds selected from one or more of PA, PI, LipO and PPO;

c) allowing the complex to separate from the aqueous supernatant phase, optionally by changing said physico-chemical conditions in the composition to reduce the solubility of the complex; and d) isolating the complex separated from the aqueous phase.

One aspect of the invention relates to a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising;

a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) contacting the aqueous phase with a soluble silicate at a pH, in the range of 3-10 and optionally, a divalent or trivalent metal ion allowing formation of an insoluble precipitate comprising said silicate and one or more the compounds selected from LipO, PPO, pectin, lipid, glycoalkaloid and phenolic compounds, and optionally, a divalent or trivalent metal ion, said insoluble precipitate is subsequently removed from the aqueous phase by physical means;

c) contacting the remaining aqueous phase with a mobile solubilized ligand at physico-chemical conditions allowing formation of a complex between the ligand and the compounds selected from one or more of PA, PI, LipO and PPO;

d) allowing the complex to separate from the aqueous supernatant phase, optionally by changing said physico-chemical conditions in the composition to reduce the solubility of the complex; and e) isolating the complex separated from the aqueous phase.

OR f) adjusting pH of the remaining aqueous phase (from step b)) to allow the formation of a precipitate comprising PA;

g) isolating the precipitate from the aqueous phase

OR h) subjecting the remaining aqueous phase (from step b)) to a membrane filtration process separating at least one of PA and PI in the retentate from at least one of PA, PI, LipO, PPO, pectin, lipid, glycoalkaloid and phenolic compounds in the permeate.

In a further aspect, the invention provides a composition comprising one or more of patatin protein (PA), protease inhibitor protein (PI), polyphenol oxidase (PPO) Lipoxygenase (LipO), glycoalkaloid and phenolic compounds obtainable from the method of the invention.

In further aspects, the invention provides food or beverages, animal feeds, pet foods, cosmetics, pharmaceuticals, nutraceuticals, dietary supplements or fermentation broths comprising the composition of the invention.

In a further aspect, the invention provides use of a composition or a product of the invention in a process for providing one or more functions selected from foam control, emulsion control, control of proteolytic activity, nutrition, gelation, solubility, organoleptic improvement, allergenicity reduction and oxidation.

In a further aspect, the invention provides use of a composition comprising glycoalkaloid obtained from the method of the invention as a medicament for treating or preventing a disease.

In a further aspect, the invention provides a method for isolating one or more of glycoalkaloid, LipO and phenolic compounds said method comprising:

a) providing an aqueous phase comprising one or more of glycoalkaloid, LipO and phenolic compounds and at least one protein;

b) contacting the aqueous phase with a mobile solubilized ligand at physico-chemical conditions allowing formation of a complex between the ligand and the protein;

c) allowing the complex to separate from the aqueous supernatant phase, optionally by changing said physico-chemical conditions in the composition to reduce the solubility of the complex; and d) isolating the one or more of glycoalkaloid, LipO and phenolic compounds comprised in the aqueous phase from the complex.

In a further aspect, the invention provides a method for isolating one or more of glycoalkaloid, LipO and phenolic compounds said method comprising:

a) providing an aqueous phase comprising one or more of glycoalkaloid LipO and phenolic compounds and at least one protein;

b) contacting the aqueous phase with a mobile solubilized ligand at physico-chemical conditions allowing formation of a complex between the ligand and the one or more of glycoalkaloid, LipO and phenolic compounds;
c) allowing the complex to separate from the aqueous supernatant phase, optionally by changing said physico-chemical conditions in the composition to reduce the solubility of the complex; and
d) isolating the one or more of glycoalkaloid, LipO and phenolic compounds comprised in the complex.

In a further aspect, the invention provides a composition comprising one or more of glycoalkaloid, LipO and phenolic compounds obtainable from the method of the invention.

In a further aspect, the invention provides a method for isolating one or more proteins comprising contacting an aqueous composition, comprising the one or more proteins with a water soluble silicon containing anionic polymer capable of binding to the protein; optionally adjusting the conditions in the composition to promote binding between the protein(s) and the polymer and causing the bound protein(s) to separate from the composition, optionally by precipitation, and isolating the separated bound protein(s), optionally comprising one or more selective elution steps to achieve one or more isolated protein fractions, optionally separated from the polymer.

BRIEF DESCRIPTION OF THE FIGURES

FIG. 1
Lane 1: Potato juice (test solution 1)
Lane 2: Supernatant, PA enriched potato juice (test solution 2)
FIG. 2
Lane 1: Potato juice (test solution 1)
Lane 2: Supernatant 5 ml juice per ml adsorbent (test solution 2)
Lane 3: Supernatant 10 ml juice per ml adsorbent (test solution 3)
Lane 4: Supernatant 15 ml juice per ml adsorbent (test solution 4)
FIG. 3
Lane 1: Potato juice (test solution 1)
Lane 2: Supernatant 10 ml juice per ml adsorbent (test solution 2)
Lane 3: Supernatant from sodium alginate precipitation of PA (test solution 3)
Lane 4: Dissolved precipitate at pH 7.0, highly PA enriched product (test solution 4)
FIG. 4
Lane 1: Potato juice (test solution 1)
Lane 2: Supernatant after 10 ml juice per ml adsorbent (test solution 2)
Lane 3: Supernatant after precipitation of PA at pH 3.5 (test solution 3)
Lane 4: Dissolved precipitate at pH 7.0 (test solution 4)
FIG. 5
Lane 1: Potato juice (test solution 1)
Lane 2: Supernatant (test solution 2)
Lane 3: Wash (test solution 3)
Lane 4: Dissolved precipitate at pH 7.5 (test solution 4)
FIG. 6
Lane 1: Dissolved precipitate pH 7.5 (test solution 4)
Lane 2: Permeate from ultrafiltration (test solution 5)
Lane 3: First diafiltration, permeate (test solution 6)
Lane 4: Second diafiltration, permeate (test solution 7)
Lane 5: Third diafiltration, permeate (test solution 8)
Lane 6: Fourth diafiltration, permeate (test solution 9)
Lane 7: Retentate from ultrafiltration=PA enriched product (test solution 10)
FIG. 7
Lane 1: Potato juice (test solution 1)
Lane 2: Supernatant A, non-precipitated material (test solution 2)
Lane 3: Wash Elution A 0.2 M NaCl pH 3.5 (test solution 5)
Lane 4: Dissolved precipitate A (test solution 8)
Lane 5: Supernatant B, non-precipitated material (test solution 3)
Lane 6: Wash Elution B with 0.4 M NaCl pH 3.5 (test solution 6)
Lane 7: Dissolved precipitate B at pH 7.5 (test solution 9)
Lane 8: Supernatant C, non precipitated material (test solution 4)
Lane 9: Wash Elution C with 0.6 M NaCl pH 3.5 (test solution 7)
Lane 10: Dissolved precipitate C at pH 7.5 (test solution 10)
FIG. 8
Lane 1: Potato juice (test solution 1)
Lane 2: Supernatant, non-precipitated material (test solution 2)
Lane 3: Wash Elution 0.7 M NaCl pH 3.5 (test solution 3)
Lane 4: Dissolved precipitate (test solution 4)
FIG. 9
Lane 1: Potato juice (test solution 1)
Lane 2: Supernatant pH 4.5 (8 ml juice to 2 ml alginate polymer, test solution 2)
Lane 3: Supernatant pH 4.0 (8 ml juice to 2 ml alginate polymer, test solution 3)
Lane 4: Supernatant pH 3.5 (8 ml juice to 2 ml alginate polymer, test solution 4)
Lane 5: Supernatant pH 4.5 (13 ml juice to 2 ml alginate polymer, test solution 6)
Lane 6: Supernatant pH 4.0 (13 ml juice to 2 ml alginate polymer, test solution 7)
Lane 7: Supernatant pH 3.5 (13 ml juice to 2 ml alginate polymer, test solution 8)
Lane 8: Potato juice (test solution 1)
Lane 9: Supernatant pH 3.0 (8 ml juice to 2 ml alginate polymer, test solution 5)
Lane 10: Supernatant pH 3.0 (13 ml juice to 2 ml alginate polymer, test solution 9)
FIG. 10
Lane 1: Potato juice (test solution 1)
Lane 2: First supernatant (test solution 2)
Lane 3: Dissolved precipitate (test solution 3)
Lane 4: Supernatant after second precipitation (test solution 4)
FIG. 11
Lane 1: Potato juice (test solution 1)
Lane 2: Supernatant at pH 4.5 (test solution 2)
Lane 3: Supernatant at pH 4.0 (test solution 3)
Lane 4: Supernatant at pH 3.5 (test solution 4)

FIG. 12
Lane 1: Potato juice (test solution 1)
Lane 2: Supernatant at pH 5.0 (MW 450,000 test solution 2)
Lane 3: Supernatant at pH 4.5 (MW 450,000 test solution 3)
Lane 4: Supernatant at pH 4.0 (MW 450,000 test solution 4)
Lane 5: Supernatant at pH 5.0 (MW 15,000 test solution 5)
Lane 6: Supernatant at pH 4.5 (MW 15,000 test solution 6)
Lane 7: Supernatant at pH 4.0 (MW 15,000 test solution 7)
FIG. 13
Lane 1: Potato juice (test solution 1)
Lane 2: Supernatant pH 4.5 (kappa, test solution 2)
Lane 3: Supernatant pH 4.0 (kappa, test solution 3)
Lane 4: Supernatant pH 3.5 (kappa, test solution 4)
Lane 5: Supernatant pH 4.5 (iota, test solution 5)
Lane 6: Supernatant pH 4.0 (iota, test solution 6)
Lane 7: Supernatant pH 3.5 (iota, test solution 7)
Lane 8: Supernatant pH 4.5 (lambda, test solution 8)
Lane 9: Supernatant pH 4.0 (lambda, test solution 9)
Lane 10: Supernatant pH 3.5 (lambda, test solution 10)
FIG. 14
Lane 1: Potato juice (test solution 1)
Lane 2: Supernatant after pH adjustment to 3.5 (test solution 2)
Lane 3: Wash of precipitate (test solution 3)
Lane 4: Dissolved precipitate (test solution 4)
Lane 5: Supernatant precipitation with lambda carrageenan (test solution 5)
Lane 6: Dissolved carrageenan precipitate (test solution 6)
FIG. 15
Lane 1: Potato juice (test solution 1)
Lane 2: Solubilized precipitate without salt wash (test solution 2)
Lane 3: Wash fraction 0.3 M sodium chloride, 5 mM sodium acetate pH 4.5 (test solution 3)
Lane 4: Solubilized precipitate after 0.3 M salt wash (test solution 5)
Lane 5: Wash fraction 0.6 M sodium chloride, 5 mM sodium acetate pH 4.5 (test solution 4)
Lane 6: Solubilized precipitate after 0.6 M salt wash (test solution 6)
FIG. 16
Lane 1: Potato juice (test solution 1)
Lane 2: Supernatant A, pH 6.1 (test solution 2)
Lane 3: Supernatant B, pH 5.5 (test solution 3)
Lane 4: Supernatant C, pH 4.9 (test solution 4)
Lane 5: Supernatant D, pH 4.5 (test solution 5)
Lane 6: Supernatant E, pH 3.9 (test solution 6)
FIG. 17
Lane 1: Potato juice (test solution 1)
Lane 2: Supernatant pH 6.1 (test solution 2)
FIG. 18
Lane 1: Potato juice (test solution 1)
Lane 2: Supernatant, pH 6.1 (test solution 2)
Lane 3: Supernatant A, pH 2.8 (test solution 3)
Lane 4: Supernatant B, pH 1.9 (test solution 4)
Lane 5: Supernatant C, pH 1.4 (test solution 5)
FIG. 19
Lane 1: Potato juice (test solution 1)
Lane 2: Supernatant A (0.3 ml water glass), pH 6.0 (test solution 2)
Lane 3: Supernatant B (0.6 ml water glass), pH 6.0 (test solution 3)
FIG. 20
Lane 1: Supernatant A (700 mg sodium silicate), pH 6.1 (test solution 2)
Lane 2: Supernatant B (350 mg sodium silicate), pH 6.1 (test solution 3)
Lane 3: Potato juice (test solution 1)
Lane 4: Supernatant C (calcium silicate), pH 6.0 (test solution 4)
FIG. 21
Lane 1: Potato juice (test solution 1) pre-treated with $CaCl_2$) and water glass
Lane 2: Supernatant from alginate precipitation pH 3.5 (test solution 2)
Lane 3: Retentate from ultrafiltration (test solution 6, product 2)
Lane 4: Dissolved alginate precipitate, pH 10 (test solution 3, product 1)
Lane 5: Permeate from ultrafiltration (test solution 4)
Lane 6: Pool of diafiltration fractions (test solution 5)
FIG. 22
Lane 1: Potato juice (test solution 1)
Lane 2: Potato juice pre-treated with water glass (test solution 2)
Lane 3: Supernatant from pH adjustment to 3.0 (test solution 3)
Lane 4: Dissolved alginate precipitate, pH 9 (test solution 4)

Figure 1:
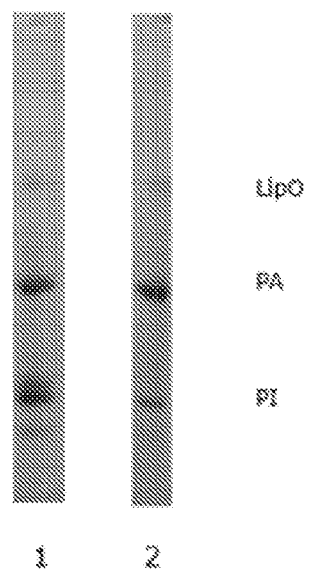
FIGS. 1 to 3:
Illustrates SDS PAGE analysis of test solutions of examples 3 to 5 respectively.

The present invention will now be described in more detail in the following.

DETAILED DESCRIPTION OF THE INVENTION

Definitions

The term "patatin", also denoted herein as "PA", means storage glycoproteins found in potatoes (*Solanum tuberosum*). Patatin represents a group of immunologically identical glycoprotein isoforms with molecular mass in the range of 40-43 kDa. Patatin also have phospolipase activity capable of cleaving fatty acids from membrane lipids. For purposes of the invention PA may be determined by different known assays, including SDS-PAGE combined with scanning densitometry as described herein (e.g. using a GS-900T™ Calibrated Densitometer from BIO-RAD Laboratories, USA) including all protein bands in the molecular weight region between 35 kD and 60 kD the PA category, ELISA testing using patatin specific antibodies, as well as enzymatic assays specific for the phospholipase activity (see e.g. Lipids, 2003, 38(6):677-82. "Determination of the phospholipase activity of patatin by a continuous spectrophotometric assay." Jiménez-Atiénzar M et al.

The term "protease inhibitor", also denoted herein as "PI", means proteins, which possess molecular weights ranging from about 3 kD to about 35 kD, e.g. found in potatoes (*Solanum tuberosum*) and other plants such as soy and lupin, animals and microorganisms capable of inhibiting the activity of e.g. serine proteases, cysteine proteases, aspartate proteases, and metalloproteases. For purposes of the invention PI, in e.g. potato derived samples, may be determined by different known assays, including SDS-PAGE combined with scanning densitometry as described herein (e.g. using a GS-900™ Calibrated Densitometer from BIO-RAD Laboratories, USA) including all protein bands in the molecular weight region between 3 kD and 35 kD in the PI category, and more broadly by enzyme inhibition assays as generally described in the art (see e.g. The Open Food Science Journal, 2011, 5:42-46. "Quantitative Determination of Trypsin Inhibitory Activity in Complex Matrices". Robin E. J. Spelbrink et al.).

The term "polyphenol oxidase", also denoted herein as "PPO", means proteins found in nearly all plant tissues including potatoes (*Solanum tuberosum*), and can also be found in bacteria, animals, and fungi. Polyphenol oxidase (tyrosinase) (TY) is a bifunctional, copper-containing oxidase having both catecholase and cresolase activity. PPO causes the rapid polymerization of o-quinones to produce black, brown or red pigments (polyphenols) which cause fruit browning. The amino acid tyrosine contains a single phenolic ring that may be oxidised by the action of PPOs to form o-quinone. Hence, PPOs may also be referred to as tyrosinases. The catalytic action of PPO has a negative impact on the quality of several fruit and vegetable crops and results in alteration of color, flavor, texture, and nutritional value. It is a limiting factor in the handling and technological processing of crops as peeled, sliced, bruised or diseased tissues rapidly undergo browning. For purposes of the invention PPO may be determined by different known assays as reviewed in: Journal of Food Biochemistry 2003, 27(5):361-422. "Physicochemical properties and function of plant polyphenol oxidase: A review". Ruhiye Yoruk et al.

The term "lipoxygenase", also denoted herein as "LipO", means proteins found in found in plants, animals and fungi capable of catalyzing the dioxygenation of polyunsaturated fatty acids. Lipoxygenases have food-related applications in bread making and aroma production but they also have negative implications for the color, off-flavour and antioxidant status of plant-based foods. In potatoes (*Solanum tuberosum*) lipoxygenase has a molecular weight of approx. 97 kD and can be detected by SDS-PAGE (see e.g. FEBS Journal, 2006, 273, 3569-3584 "Patatins, Kunitz protease inhibitors and other major proteins in tuber of potato cv. Kuras" Guy Bauw et al.). For purposes of the invention LipO may be determined by different known assays, including SDS-PAGE combined with scanning densitometry as described herein (e.g. using a GS-900™ Calibrated Densitometer from BIO-RAD Laboratories, USA) as wells as enzyme activity assays as described in e.g. J. Agric. Food Chem., 2001, 49, 32-37. "Colorimetric Method for the Determination of Lipoxygenase Activity". Gordon E. Anthon et al.

The term "glycoalkaloid" or "alkaloid glucoside" means a family of chemical compounds derived from alkaloids in which sugar groups are appended. There are several that are potentially toxic, most notably those which are the poisons commonly found in the plant species *Solanum dulcamara* (nightshade). A prototypical glycoalkaloid is solanine (composed of the sugar solanose and the alkaloid solanidine), which is found in potatoes (*Solanum tuberosum*). For purposes of the invention glycoalkaloid may be determined by different known assays, including a standard HPLC assay as described Eng. Life Sci., 2005, 5, 562-567. "Optimization of glycoalkaloid analysis for us in industrial potato fruit juice downstreaming". Alt, V., Steinhof et al.

The term "ligand" means a molecule comprising a functional group or moiety capable binding to another molecule by non-covalent bonds, such as of hydrogen bonds, hydrophobic bonds, π-π (pi-pi) bonds and ionic bonds.

The term "complex" means a molecule bound to a ligand by non-covalent bonds, such as of hydrogen bonds, hydrophobic bonds, π-π (pi-pi) bonds and ionic bonds.

The term "protein:ligand dry weight ratio" means the dry weight ratio in a complex between a protein and the molecule comprising the ligand. If for example the ligand is a polymer comprising a multitude of functional groups bound to a protein, then the protein:ligand dry weight ratio is the ratio between the dry weight of protein in the complex and the dry weight of polymer in the complex.

The term "dry weight" means the weight or mass of a substance remaining after removal of water by heating to constant weight at 110 degrees Celcius. The dry weight per ml sample is thus the weight or mass of a substance remaining after removal of water by heating to constant weight at 110 degrees Celcius per ml sample applied to drying.

The term "isolating" or "separating" means any human intervention which change the relative amount of the compound compared to another selected constituent in a given matrix to a higher relative amount of the compound relative to the other constituent. In an embodiment, the compound may be isolated into a pure or substantially pure form. In this context, a substantially pure compound means that the compound preparation contains less than 10%, such as less than 8%, such as less than 6%, such as less than 5%, such as less than 4%, such as less than 3%, such as less than 2%, such as less than 1%, such as less than 0.5% by weight of other selected constituents. In an embodiment, an isolated compound is at least 50% pure, such as at least 60% pure, such as at least 80% pure, such as at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by dry weight.

The term "synthetic" or "non-naturally occurring" means that A compound is not normally found in nature or natural biological systems. In this context, the term "found in nature or in natural biological systems" does not include the finding of a compound in nature resulting from releasing the compound to nature by deliberate or accidental human intervention. Synthetic compounds may include compounds completely or partially synthetized by human intervention and/or compounds prepared by human modification of a natural compound.

The term "membrane separation process" refers to a process using a semi-permeable membrane, allowing only compounds having a size lower that a certain value to pass, to separate molecules of a higher size in a liquid or gas continuous phase composition from molecules of a lower size. In this context, liquid or gas continuous phase compositions are to be understood in the broadest sense, including both single phase compositions such as solutions or gases, and dual phase compositions such as slurries, suspensions or dispersions wherein a solid is distributed in a liquid or gas phase.

The term "retentate" means compounds which are not allowed to pass a selected membrane in a which have a membrane separation process.

The term "permeate" or "filtrate" means compounds which can has passed a selected membrane in a which have a membrane separation process.

The term "precipitation" refers to the phenomenon that a dissolved compound exceeding its solubility in the solvent undergoes a phase transition from a dissolved liquid state to a solid state. Precipitation is often caused by a chemical reaction and/or a change in the solution conditions. The solidified compound is referred to as the "precipitate".

The term "diafiltration" means a technique that uses ultrafiltration membranes to completely remove, replace, or lower the concentration of salts or solvents from solutions containing proteins, peptides, nucleic acids, and other biomolecules. The process selectively utilizes permeable (porous) membrane filters to separate the components of solutions and suspensions based on their molecular size. An ultrafiltration membrane retains molecules that are larger than the pores of the membrane while smaller molecules such as salts, solvents and water, which are 100% permeable, freely pass through the membrane. In a diafiltration process the retentate is added water or a buffer composition while the membrane filtration process continuously removes water, salts and low molecular weight compounds to the permeate side of the membrane.

The term "adsorption" means a process in which molecules from a gas, liquid or dissolved solid adhere to a surface of a solid phase adsorbent. Likewise, and adsorbent (also named a solid phase adsorbent) is an insoluble material on which adsorption can occur.

The term "mobile solubilized", as used herein about a ligand, means that the ligand which is at least partially dissolved in a solvent and is sufficiently mobile allowing the ligand to form complexes with a compound dissolved in the solvent. Thus, mobile solubilized ligands are, in contrast to solid phase adsorbents, at least partially dissolved in a solvent. Fully dissolved "mobile solubilized" ligands form homogeneous solutions in a solvent while partly dissolved "mobile solubilized" ligands form colloidal dispersions or solutions.

The term "immobilized solid carrier" means a solid phase adsorbent which may be in the form of insoluble, permeable or impermeable, materials such as spherical or amorphous beads or fibers, or membranes.

The term "water activity" in a solution is defined as:

$$aw=p/p0$$

where p is the vapor pressure of water over the solution, and $p0$ is the vapor pressure of pure water at the same temperature.

The term "pectin" means pectic polysaccharides, which are rich in galacturonic acid. The amount, structure and chemical composition of pectin differs among plants, within a plant over time, and in various parts of a plant. In natural pectins around 80 percent of carboxyl groups of galacturonic acid are esterified with methanol or are acetylated.

The term "phenolic compounds" means aromatic or heteroaromatic compounds comprising one or more ring systems and one or more phenolic hydroxyl groups.

The term "potato" means the tubers of plant genus *Solanum*, particularly the species *S. tuberosum*.

The term "protein concentration" means the amount of protein per liter of a sample calculated as the total weight or mass of amino acids per liter as determined according to EUROPEAN PHARMACOPOEIA 5.0 section 2.2.56. AMINO ACID ANALYSIS or by determination of total nitrogen in a sample by the method of Kjeldahl using the conversion factor N×6.25. All samples are dialyzed against demineralized water in dialysis tubing cellulose membrane (Sigma-Aldrich, USA, cat. No.: D9652) to remove any free amino acids and low molecular weight peptides prior to the amino acid determination.

The term "silicon containing anionic polymer" means a polysilicate or polysiloxane (silicone) or mixtures of these. Silicates are compounds formed by the reaction of the acidic oxide silica ($SiO_2$) with various basic metal oxides. Silicates contain silicon oxo anions which possess covalent Si—O bonds. These compounds have 2-coordinate oxygen atoms that link silicon atoms together into oligomeric or one-, two-, or three-dimensional polymers. Polysiloxane (or silicone) are polymerized siloxanes, silicones consist of an inorganic silicon-oxygen backbone chain ( . . . —Si—O—Si—O—Si—O— . . . ) with organic side groups attached to the silicon atoms. These silicon atoms are tetravalent.

So, silicones are polymers constructed from inorganic-organic monomers. Silicones have in general the chemical formula [$R_2SiO$]n, where R is an organic group. In the context of the invention silicates and silanes are defined as being polymers.

The term "soluble" means solubility in water at a concentration of at least 1 g/L at 25 degrees Celsius.

The term "solubilized silicon containing anionic polymer" means a solution of the polymer (as opposed to the solid polymer without added solvent). The solution may be saturated and non-dissolved polymer may be present in the solution.

The term "anionic polymer" means a polymer carrying one or more negative charges in solution.

The term "comprise" and "include" as used throughout the specification and the accompanying items/claims as well as variations such as "comprises", "comprising", "includes" and "including" are to be interpreted inclusively. These words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The Method for Isolating Protein Compounds from Plant Material

The present inventors have surprisingly found that certain combinations of processing steps, each providing specific improvements to the purity of the proteins, can provide both the protein quality and the industrial applicability, robustness and profitability which enables a long-needed solution to the valorization of the very large volume of liquid side-streams resulting from the starch manufacturing industry.

Such solution will not only bring value to the starch and potato industry but also mean an increased production of plant derived food grade proteins that can supplement and substitute the animal derived proteins which—due to the intensive animal farming associated with it—is an increasing burden to the environment and is predicted soon to become a scarce resource.

With one objective being to prepare industrial scale isolates of useful compounds present in plant materials, in particular in tubers of plants of the genus *Solanum*, such as *S. tuberosum* the inventors of this invention have developed and provided a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, glycoalkaloid and phenolic compounds said method comprising:

a) providing an aqueous phase comprising compounds selected from two or more of PA, PI, PPO, LipO, glycoalkaloid and phenolic compounds of which at least one compound is selected from PA, PI, LipO and PPO;

b) contacting the aqueous phase with a mobile solubilized ligand at physico-chemical conditions allowing formation of a complex between the ligand and the compounds selected from one or more of PA, PI, LipO and PPO;

c) allowing the complex to separate from the aqueous supernatant phase, optionally by changing said physico-chemical conditions in the composition to reduce the solubility of the complex; and
d) isolating the complex separated from the aqueous phase.

It is to be understood that in one embodiment a compound selected in the first group is deselected in the second group. It is also to be understood that in another embodiment the aqueous phase of step a) comprises a compound selected from one or more of PA, PI, PPO and a compound selected from one or more of glycoalkaloid, LipO and phenolic compounds.

This method has demonstrated unexpectedly useful for industrial scale separation of useful compounds from undesirable compounds, because plant materials applied in industry often are unprocessed and raw both to preserve nutritional value and to save costs. For example, when processing potatoes into e.g. potato starch usually unpeeled potatoes are used and since many unwanted compounds are present in the peel, it may be important to be able to remove such unwanted compounds from the wanted ones.

In an embodiment of the invention the separated complex comprises a combination of PA and PI and PPO and wherein the complex is separated from the aqueous supernatant phase by precipitation.

In an embodiment the precipitate is enriched in PA compared to other compounds so that the dry weight ratio PA:PI in the precipitate is preferably higher than the dry weight PA:PI ratio for PA and PI remaining dissolved in the aqueous supernatant phase. In this embodiment the enriched precipitate may be further processed by re-dissolving the precipitated complex in an aqueous solvent and further isolating PA from the PI and PPO by a mechanical separation process concentrating the PA in the retentate. As an alternative in this embodiment the PA-enriched precipitated complex may also be isolated without re-dissolution, by a mechanical separation process concentrating one or more of PA, PI and PPO in the retentate. In this embodiment, further the aqueous supernatant phase remaining from the PA enriched precipitate may be
a) contacted with a further mobile solubilized ligand at physico-chemical conditions in the aqueous supernatant phase allowing formation of a complex between the ligand and compounds selected from one or more of PI, and PPO remaining in the aqueous supernatant phase;
b) allowing the complex to separate from the aqueous supernatant phase, optionally by changing said physico-chemical conditions in the composition to reduce the solubility of the complex so that the complex separates from the aqueous supernatant phase; and
c) isolating the complex.

In another embodiment, the precipitate comprises the majority of PA and PI, so that the sum of PA and PI remaining dissolved in the aqueous supernatant phase is less than 20 wt %, optionally less than 10 wt. %, optionally less than 5 wt %, optionally less that 1 wt % of the total PA and PI (depletion of PA and PI in the aqueous phase). In this embodiment, the precipitate may be further processed by dissolving the precipitated complex in an aqueous solvent and isolating PA from one or more compounds selected from PI, and PPO by a mechanical separation process concentrating the PA in the retentate. As an alternative in this embodiment the precipitated complex may also be isolated without re-dissolution, by a mechanical separation process concentrating one or more of PA, PI and PPO in the retentate. As a further alternative in this embodiment, the precipitate may be further processed by dissolving the precipitated complex in an aqueous solvent and isolating PA from one or more compounds selected from PI and PPO by selectively adsorbing the one or more compounds selected from PI and PPO on an immobilized solid carrier at conditions where the carrier will bind the one or more compounds selected from PI and PPO.

In another embodiment of the invention the dry weight ratios PI:PA or PPO:PA in the precipitate is higher than the dry weight ratios PI:PA or PPO:PA for PA, PI and PPO remaining dissolved in the aqueous supernatant phase. In this embodiment, the method may further comprise concentrating PA in the aqueous supernatant phase by a mechanical separation process concentrating PA in the retentate, optionally combined with diafiltration. As an alternative in this embodiment, the method may further comprise:
a) contacting the aqueous supernatant phase with a further mobile solubilized ligand at physico-chemical conditions in aqueous supernatant phase allowing formation of a complex between the ligand and PA;
b) allowing the complex to separate from the aqueous supernatant phase, optionally by changing said physico-chemical conditions in the composition to reduce the solubility of the complex so that the complex separates from the aqueous supernatant phase; and
c) isolating the complex.

In a further embodiment, the method of the invention further comprises adsorbing dissolved PA in the aqueous supernatant phase on an immobilized solid carrier at conditions where the carrier will bind PA.

In a further embodiment the method of the invention further comprises pre-treating the aqueous phase by adsorbing one or more of PI, LipO and PPO on an immobilized solid carrier at conditions where the carrier will bind the one or more of PI, LipO or PPO.

An aspect of the present invention relates to a method for reducing turbidity of an aqueous phase comprising compounds selected from two or more of PA, PI, PPO, LipO, pectin, lipid, glycoalkaloid and phenolic compounds of which at least one compound is selected from PA, PI, LipO and PPO;
a) providing an aqueous phase comprising compounds selected from two or more of PA, PI, PPO, LipO, pectin, lipid, glycoalkaloid and phenolic compounds of which at least one compound is selected from PA, PI, LipO and PPO;
b) contacting the aqueous phase with a soluble silicate at a pH in the range of 3-10, allowing formation of an insoluble precipitate comprising said silicate and one or more the compounds selected from LipO, PPO, pectin, lipid, glycoalkaloid and phenolic compounds, said insoluble precipitate is subsequently removed from the aqueous phase by physical means;
thereby obtaining an aqueous phase having reduced turbidity compared to an untreated aqueous phase.

In another aspect, the invention provides a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) performing one or more steps to reduce the concentration of solanine in the dry matter of the aqueous phase with at least 5 percent, and to achieve an optical density at 620 nm of the remaining aqueous phase of less than 0.7;

thereby obtaining an aqueous phase having reduced turbidity compared to an untreated aqueous phase.

In one embodiment of the invention the precipitate in step b) of the methods of the present invention comprise at least 10% of the PA initially present in the aqueous phase, such as at least 20%, such as at least 30%, such as at least 50%, such as at least 70%, such as at least 85%, such as at least 90% of the PA initially present in the aqueous phase.

The present invention may in one embodiment be described as a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) contacting the aqueous phase with a soluble silicate at a pH, in the range of 3-10 and optionally, a divalent or trivalent metal ion allowing formation of an insoluble precipitate comprising said silicate and one or more the compounds selected from LipO, PPO, pectin, lipid, glycoalkaloid and phenolic compounds, and optionally, a divalent or trivalent metal ion, said insoluble precipitate is subsequently removed from the aqueous phase by physical means;

c) contacting the remaining aqueous phase with a mobile solubilized ligand at physico-chemical conditions allowing formation of a complex between the ligand and the compounds selected from one or more of PA, PI, LipO and PPO;

d) allowing the complex to separate from the aqueous supernatant phase, optionally by changing said physico-chemical conditions in the composition to reduce the solubility of the complex; and e) isolating the complex separated from the aqueous phase.

OR f) adjusting pH of the remaining aqueous phase (from step b of the methods of the present invention)) to allow the formation of a precipitate comprising PA;

g) isolating the precipitate from the aqueous phase

OR h) subjecting the remaining aqueous phase (from step b of the methods of the present invention)) to a membrane filtration process separating at least one of PA and PI in the retentate from at least one of PA, PI, LipO, PPO, pectin, lipid, glycoalkaloid and phenolic compounds in the permeate Siicates and Polymers Such as Silicate The polymer of the invention may be an inorganic polymer, optionally comprising one or more organic groups. Such an inorganic polymer may comprise silicon, optionally in the form of silicate or silicone, such as polymeric sodium silicate or polymeric silicone or a combination thereof. In a preferred embodiment the polymer is a solubilized silicon containing anionic polymer.

Sodium silicate is the common name for compounds with the formula $Na_2(SiO_2)nO$. A well-known member of this series is sodium metasilicate, $Na_2SiO_3$. Also, known as water glass or liquid glass, these materials are available in aqueous solution and in solid form.

For silicate and silicone based polymers, it has unexpectedly been found that in order to form the right conformation for binding the compounds of the invention, the complexing reaction should be done by first solubilizing the polymer such that it is in aqueous solution prior to contacting the compound of the invention with the polymer carrying the ligand. Thus, it has surprisingly been found that in some embodiments the efficiency of the complex formation and separation is significantly lower if the solid (non-solubilized) polymer is added directly to the composition.

In one embodiment, the silicate is sodium silicate, or a silicon containing anionic polymer as describe above. In another embodiment, the silicate is sodium alginate.

The silicate concentration is in the range of 0.2-5 g/L in the present context may preferably in the range of 0.5-3 g/L, 0.5-4 g/L, 0.5-5 g/L, 1-3 g/L, 1-4 g/L, 1-5 g/L, 1.5-3 g/L, 1.5-4 g/L, 1.5-5 g/L, 2-3 g/L, 2-4 g/L, 2-5 g/L, 2.5-3 g/L, 2.5-4 g/L, or 2.5-5 g/L. The silicate concentration may be in the range of 0.2-5 g/L, preferably in the range of 0.5-3 g/L.

In one embodiment, the invention relates to a method as described above, wherein the silicate concentration is in the range of 0.2-5 g/L.

Metal Ions

In one embodiment, the invention relates to a method, wherein the concentration of the divalent or trivalent metal ion in the aqueous phase is between 2-100 mM, such as but not limited to the range of 2-50 mM, 3-40 mM, 4-40 mM or 5-25 mM.

In one embodiment, the invention relates to a method, wherein the divalent or trivalent metal ion is a calcium, magnesium or aluminum ion.

Thus, one embodiment of the present invention relates to a method of the present invention, wherein step b) further comprises addition of a divalent or trivalent metal ion at a concentration in the aqueous phase of between 2-100 mM.

The divalent or trivalent metal ion may be a calcium, magnesium or aluminum ion.

Physical Means for Removal of Supernatant

In one embodiment, the invention relates to a method, wherein the physical means in step b) of the methods of the present invention is centrifugation and the supernatant is subsequently removed.

In one embodiment, the invention relates to a method, wherein the precipitate is washed by resuspension in water and pH adjusted to 3.0 with hydrochloric acid and centrifuged and the supernatant removed. Other pH levels may be applicable depending on the intended use, and such levels is contemplated by the disclosure herein such as but not limited to pH between 2-5.

In one embodiment, the invention relates to a method, wherein the washed precipitate is suspended in water and pH is slowly adjusted to pH 7-10 with e.g. 1 M NaOH.

In one embodiment, the invention relates to a method, wherein the physical means in step b) of the methods of the present invention is centrifugation and the supernatant is subsequently removed.

In one embodiment of the invention the isolation of the precipitate from the aqueous phase in step c of the methods of the present invention is performed using a decanter centrifuge.

In one embodiment of the invention the isolated precipitate in step c) of the methods of the present invention is further treated to produce a protein powder as an animal feed product. In one embodiment, the precipitate is washed with an aqueous solution of an acid and dried.

Reduction of Optical Density

In one embodiment of the present invention is the optical density at 620 nm of the remaining aqueous phase less than 0.8. The optical density may be less than 0.7. The optical density may be less than 0.6. The optical density may be less than 0.5. The optical density may be less than 0.2. The optical density may be less than 0.1.

The reduction of the concentration of solanine in step b) of the methods of the present invention can be done by changing the physico-chemical conditions by any of the methods mentioned herein, including contacting the aqueous phase with soluble silicate (see below).

In one embodiment of the present invention is the reduction of the concentration of solanine (step b above) of the methods of the present invention and achieving an optical density at 620 nm of the remaining phase the result of two or more independent steps.

In another embodiment of the present invention is the reduction of the concentration of solanine (step b above) of the methods of the present invention and achieving an optical density at 620 nm of the remaining phase the result of a single step.

Example 24 shows an experimental basis for a single step. Here is a single step with treatment using silicate and calcium used to achieve a reduction in turbidity and solanine.

Thus, the one or more steps needed to achieve the reduction of the concentration of solanine (step b of the methods of the present invention) and achieving an optical density at 620 nm of the remaining phase can comprise any of the procedures for reducing turbidity mentioned herein. For example a combined step with treatment using silicate and calcium.

However, in a certain aspect of the invention the one or more steps needed to achieve the reduction of the concentration of solanine (step b of the methods of the present invention) and achieving an optical density of the remaining aqueous phase of less than 0.7 may surprisingly comprise a complete or partial precipitation of PA and other impurities essentially without the co-precipitation of PI, which may then be isolated and concentrated with a high yield, high purity and exceptional high clarity. This is exemplified in the experimental section of the present disclosure, including example 33.

Thus, a further aspect of the present invention relates to a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) adjusting pH of the aqueous phase to allow the formation of a precipitate comprising at least 10% of the PA initially present in the aqueous phase and to achieve an optical density at 620 nm of the remaining aqueous phase of less than 0.7;

c) isolating the precipitate from the aqueous phase d) isolating PI from the remaining aqueous phase (from step c)).

In one embodiment of the invention the optical density at 620 nm of the remaining aqueous phase in step b) of the methods of the present invention is less than 0.5; such as less than 0.3; such as less than 0.2; such as less than 0.1; such as less than 0.07

In another embodiment of the present invention is the concentration of solanine in the dry matter of the remaining aqueous phase in step b) of the methods of the present invention reduced with at least 5 percent.

In one embodiment, the invention relates to a method, wherein step b) of the methods of the present invention comprises performing one or more steps to reduce the concentration of solanine in the dry matter of the aqueous phase with at least 5 percent.

In one embodiment, the invention relates to a method, wherein step b) of the methods of the present invention comprises performing one or more steps to reduce the concentration of solanine in the dry matter of the aqueous phase with at least 25 percent.

In one embodiment, the invention relates to a method, wherein step b) of the methods of the present invention comprises performing one or more steps to reduce the concentration of solanine in the dry matter of the aqueous phase with at least 15 percent, and to achieve an optical density at 620 nm of the remaining aqueous phase of less than 0.7.

Time and Temperature

In one embodiment, the invention relates to a method, wherein the formation of an insoluble precipitate in step b) of the methods of the present invention is made by incubating the aqueous phase for less than 120 min, preferably less than 60 min, preferably less than 30 min, preferably less than 15 min.

In one embodiment, the invention relates to a method, wherein the formation of an insoluble precipitate in step b) of the methods of the present invention is made by incubating the aqueous phase at 15-50° C., preferably at 20-45° C., preferably at 22-40° C., preferably at 25-35° C. As shown in Example 30 elevation of the temperature makes the process faster, which may be desirable in commercial settings.

In one embodiment of the invention the aqueous phase in step b) of the methods of the present invention has a temperature in the range of 20-62 degrees Celsius, such as in the range of 24-48 degrees Celsius, such as in the range of 30-45 degrees Celsius, such as in the range of 35-45 degrees Celsius, such as in the range of 41-60 degrees Celcius, such as in the range of 45-58 degrees Celcius, such as in the range of 48-58 degrees Celcius.

In one embodiment of the invention pH adjustment in step b) of the methods of the present invention is performed less than 200 minutes after the fruit juice has been released from the potatoes, such as less than 150 minutes, such as less than 100 minutes, such as less than 60 minutes, such as less than 30 minutes, such as less than 20 minutes, such as less than 10 minutes, such as less than 5 minutes after the fruit juice has been released from the potatoes.

In one embodiment of the invention the formation of an insoluble precipitate in step b) of the methods of the present invention is made by incubating the aqueous phase for less than 120 min.

In one embodiment of the invention the formation of an insoluble precipitate in step b) of the methods of the present invention is made by incubating the aqueous phase at 15-50° C.

No Use of Synthetic Polymers

Common water-soluble silicates like sodium silicate and sodium meta-silicate, also known in the form of highly concentrated solutions as "water glass", are naturally occurring inorganic compounds that are present in small concentrations in most living organisms and find widespread use both as food processing aids, for pharmaceutical products and for many technical applications.

Addition of synthetic polymers into food materials or contacting of food raw materials with synthetic polymers, such as e.g. polyacrylamide derivatives and anionic polyacrylamides, is generally unwanted due to the risk of unknown toxicological effects arising in the food matrix. For certain applications, such synthetic polymers may be used as non-ingredient process aids but must in any case be scrutinized and approved for the purpose by proper regulatory affairs which is a costly and lengthy process. Common to all of these it must further be assured that the synthetic polymer does not migrate into the final food product posing a risk to the consumers.

In the present context, the formation of an insoluble precipitate in the methods of the present invention does not comprise contacting the aqueous phase with a synthetic anionic acrylamide.

In one embodiment of the invention step b) of the methods of the present invention does not comprise the addition of a synthetic polymer.

In one embodiment of the invention step b) of the methods of the present invention does not comprise the addition of an acrylic polymer.

Mobile Solubilized Ligand

The mobile solubilized ligand of the invention is in principle any ligand which is soluble in aqueous solution and capable of binding to a compound of the invention and separate from the aqueous phase, by changing its conditions. However in particular, the ligand of the invention is a functional group of a polymer, said functional group in an embodiment being selected from one or more of a hydrophobic group, an amphiphilic group and a hydrophilic group, optionally an organic group. In particular, the ligand may be selected from one or more of anionic groups, cationic groups, aryl groups, aromatic groups, heteroaromatic groups and alkyl groups. More particularly, the functional group may be selected from one or more of carboxyl, sulphate, sulphonate, phosphate, phosphonate, silicate and silicone groups, such as groups selected from one or more of aromatic sulfonic acids including polystyrene sulfonic acid (PSS), aromatic carboxylic acids, aromatic phosphonic acids.

The ligand of the invention is capable of binding to PA, PI, LipO or PPO by bonds selected from one or more of hydrogen bonds, hydrophobic bonds, π-π (pi-pi) bonds and ionic bonds.

In an embodiment of the invention the polymer of the invention has an average molecular size of at least 500 KDa, optionally at least 1500, optionally at least 5,000 kDa, optionally between 5,000 to 10,000,000 KDa, optionally between 10,000 to 1,000,000 KDa, optionally between 10,000 to 500,000 KDa, optionally between 10,000 to 200,000 KDa, optionally between 12,000 to 190,000 KDa, optionally between 200,000 to 400,000 KDa, The polymer of the invention carrying the ligand may be linear or branched and may in aqueous solution at pH 7 and 20° C. have a solubility of at least 50 g/L, optionally at least 100 g/L. The polymer of the invention may further be an aqueous solution at a concentration of 50 g/L, at pH 7 and at 20° C. have a shear viscosity of less than 100000 cP, optionally less than 50000, optionally less than 25000 cP.

In a further embodiment, the polymer of the invention carrying the ligand provides in aqueous solution a shear thinning liquid, a Newtonian liquid or a thixotropic liquid.

The polymer of the invention carrying the ligand has in an embodiment an isoelectric point of less than pH 4, while it in another embodiment in aqueous solution has a net negative charge at pH less than 7, optionally less than pH 6, optionally less than pH 5, optionally less than pH 4.5, optionally less than pH 4.0.

In a further embodiment, the polymer of the invention comprises in aqueous solution at pH 7 at least 0.5 millimoles anionic groups per gram polymer, such as at least 2 millimoles anionic groups per gram polymer, such as at least 4 millimoles anionic groups per gram polymer, such as between 0.5 to 8 millimoles anionic groups per gram polymer, such as 1 to 7 millimoles anionic groups per gram polymer, such between 2 to 6 millimoles anionic groups per gram.

Accordingly, in an embodiment the silicon containing polymer is solubilized prior to contacting with the compounds selected from two or more of PA, PI, PPO, LipO, glycoalkaloid and phenolic compounds and in a further embodiment the silicon containing polymer is dissolved in the aqueous composition under conditions which do not lead to formation of substantial amounts of separated proteins until the conditions have been adjusted to effect separation. Further, the silicon containing polymer may advantageously be dissolved in the aqueous composition at pH 7 or higher, optionally at pH 8 or higher, optionally at pH 9 or higher, optionally at pH 10 or higher. In addition, precipitation of protein bound to the silicon containing polymer is caused by adjusting pH to below pH 8, optionally to below 7, optionally to below pH 6.5, optionally to a pH between 1 to 9, optionally to a pH between 2 to 8, optionally to a pH between 3 to 7, optionally to a pH between 3.5 to 6.5, optionally to a pH between 4.5 to 6.5, optionally to a pH between 5.5 to 6.5. The silicon containing polymer is preferably a metal silicate such as selected from one or more of sodium silicate, potassium silicate, ammonium silicates, quaternary ammonium silicates. One preferred metal silicate is water glass (sodium metasilicate). The silicon containing polymer may also comprise silicone moieties, optionally in a mixture with silicates. The silicone moieties may comprise an organic functional group capable of binding to proteins and the organic functional group may comprise a hydrophobic group such as a C2-C12 branched or un-branched alkyl group, an aromatic or heteroaromatic ring system or combinations of these. The organic functional group may also comprise one or more anionic groups, one or more cationic groups or combinations of these. In an embodiment. The silicone moieties may be derived from the a reactive silane, optionally glycidoxypropyl or allyl silane, optionally 3-Glycidoxypropyldimethoxymethylsilane, 3-Glycidoxypropyldimethylethoxysilane (3-Glycidyloxypropyl)trimethoxysilane, Allyltrimethoxysilane, Allyltriethoxysilane. In another embodiment the silicone moieties are mixed with silicates in a molar ratio silicone:silicate in the range of 0.001 to 0.99, optionally 0.01 to 0.90, optionally 0.02 to 0.8, optionally 0.03 to 0.7, optionally 0.05 to 0.6, optionally 0.07 to 0.5, optionally 0.1 to 0.4, optionally 0.05 to 0.30, optionally 0.1 to 0.2.

The polymer of the invention may also be a naturally occurring polymer, such as a naturally occurring polysaccharide. The polysaccharide may be selected from one or more of chitosanate, carrageenanate, alginate, pectinate, xanthan gum, gum Arabic and dextran.

Alternatively, the polymer of the invention may be a synthetic polymer. Such synthetic polymers include derivatized naturally occurring polysaccharide, such as those selected from one or more of dextran sulphate, carboxymethyl dextran, carboxymethylcellulose (CMC), carboxymethyl starch, cellulose sulphate, starch sulphate, cellulose phosphate, cellulose phosphonate, starch phosphate, starch phosphonate. The synthetic polymer may also be one or more of polyacrylic acids (PAA), polymethacrylic acids (PMAA) and polyvinylsulfonic acids (PVS), silicones, and derivatives hereof.

One embodiment of the present invention relates to a method as described herein, which after step b) of the methods of the present inventions comprises the steps of;
c) contacting the remaining aqueous phase with a mobile solubilized ligand at physico-chemical conditions allowing formation of a complex between the ligand and the compounds selected from one or more of PA, PI, LipO and PPO;
d) allowing the complex to separate from the aqueous supernatant phase, optionally by changing said physico-chemical conditions in the composition to reduce the solubility of the complex; and
e) isolating the complex separated from the aqueous phase.

In one embodiment of the invention the PI isolated in step d) of the methods of the present invention contains less than 0.30 g PA per PI, such as less than 0.20 g PA, such as less than 0.15 g PA, such as less than 0.10 g PA per g PI.

In one embodiment of the invention the PI isolated in step d) of the methods of the present invention contains less than 200 ppm solanine, such as less than 100 ppm solanine such as less than 70 ppm solanine, such as less than 50 ppm solanine, such as less than 25 ppm solanine, such as less than 10 ppm solanine on a dry matter basis.

In one embodiment of the invention the PI isolated in step d) of the methods of the present invention has a purity (N×6.25) corresponding to at least 70%, such as at least 75%, such as at least 80%, such as at least 85%, such as at least 90% PI on a dry matter basis.

In one embodiment of the invention the PI isolated in step d) of the methods of the present invention constitutes more than 75%, such as more than 80%, such as more than 85%, such as, more than 90%, such as more than 95% of the PI present in the aqueous phase of step a).

In one embodiment of the invention the PI isolated in step d) of the methods of the present invention contains less than 25%, such as less than 15%, such as less than 10%, such as less than 5%, such as less than 2% of the polyphenoloxidase activity present in the aqueous phase provided in step a) on a dry matter basis.

Immobilized Carriers

In several embodiments, the method of the invention also comprises a step of adsorbing and/or binding compounds selected from one or more of PA, PI, LipO, PPO, glycoalkaloid and phenolic compounds to a solid immobilized carrier. Such carrier would preferably comprise a porous cross-linked polymer comprising or derivatised with a ligand. The polymer with ligand which is cross linked is preferably selected among the above mentions polymers and ligands. The cross-linking may be covalent or non-covalent and for cross-linking the polymer one or more of the abundant well known standard methods for cross-linking may be applied, such as those described in "Methods for affinity-based separations of enzymes and proteins, pp 112-123 Ed.: M. N. Gupta. Springer, Basel 2002"

The solid immobilized carrier may be applied in the form of a powder capable of being packed in a chromatographic column or it may be formed into solid beads. The step of binding compounds to the solid immobilized carrier may comprise allowing an aqueous solution of the compounds to pass the pores of the carrier at conditions allowing the ligand to bind one or more of the compounds.

In a specific embodiment, the immobilized carrier at the selected conditions adsorbs more PI than compounds selected from one or more of PA, LipO and PPO. In another embodiment, the carrier at the selected conditions adsorbs more PA than compounds selected from one or more of PI, LipO and PPO. In a further embodiment, the carrier at the selected conditions adsorbs more PPO and LipO than compounds selected from one or more of PA an PI. In a further embodiment, the carrier at the selected conditions adsorbs more compounds selected from one or more of PI, LipO and PPO than PA. In a further embodiment, the carrier at the selected conditions adsorbs more compounds selected from one or more of PI and PA than PPO and LipO. In a further embodiment, the carrier at the selected conditions adsorbs more compounds selected from one or more of PPO, LipO and PA than PI. In a further embodiment, the carrier at the selected conditions adsorbs more compounds selected from one or more of glycoalkaloid and phenolic compounds than compounds selected from one or more of PPO, PA, LipO and PI. Such carriers (adsorbents) may suitably by made of porous synthetic polymers and may be hydrophobic in nature. In one embodiment of the invention the porous synthetic polymer is a hydrophobic adsorbent comprising a cross-linked aromatic backbone such as a cross-linked vinyl benzene backbone. In one embodiment of the invention the porous adsorbent is a Dowex, Lewatit or Amberlite adsorbent.

Complex Formation Between Compound(s) and Ligand(s)

In the method of the invention the ligand will bind to the compound in a condition dependent manner, so that the choice of ligand and conditions chosen in the aqueous phase will determine which compound(s) are bound and in which ratios.

One important condition is the pH of the aqueous phase, and accordingly the complex formation between the ligand and the compound selected from one or more of PA, PI, LipO, PPO, glycoalkaloid and phenolic compounds is carried out in aqueous phase at pH 8 or less, such as pH 7 or less, optionally at pH 6 or less, optionally at pH 5.0 or less, optionally pH at 4.6, optionally pH at 4.5 or less, at pH 2 or more, optionally at pH 3 or more, optionally at pH between 3.5 to 4, optionally at pH between 5 to 6. optionally at pH between 5.5 to 8.0, such as pH between 6 to 7.

Higher pH values are useful when applying silicon containing polymers, which binds proteins at a higher pH.

Another important condition is the conductivity and/or the ionic strength of the aqueous solution and accordingly the complex formation between the ligand and the compound selected from one or more of PA, PI, LipO, PPO, glycoalkaloid and phenolic compounds is carried out in aqueous phase having a conductivity of at least 5 mS/cm, optionally at least 7 mS/cm, optionally at least 9 mS/cm, optionally at least 10 mS/cm, optionally at least 12 mS/cm, optionally between 5-20 mS/cm, optionally between 8-15 mS/cm, optionally between 9-13 mS/cm.

A further important condition is the temperature of the aqueous phase and accordingly the complex formation between the ligand and the compound selected from one or more of PA, PI, LipO, PPO, glycoalkaloid and phenolic compounds is carried out in aqueous phase having a temperature of between 4° C. to 50° C., optionally between 10° C. to 45° C., optionally between 12° C. to 40° C., optionally between 15° C. to 35° C.

A still further important condition is the concentration of the mobile solubilized ligand in the aqueous phase and accordingly the complex formation between the ligand and the compound selected from one or more of PA, PI, LipO, PPO, glycoalkaloid and phenolic compounds is carried out in aqueous phase having a polymer concentration between 0.1 to 50 g/L, optionally between 0.2 to 20 g/L, optionally between 0.2 to 5 g/L, optionally between 0.2 to 3 g/L, optionally between 0.2 to 2 g/L, optionally between 0.5 to 3 g/L optionally between 0.5 to 2 g/L, optionally between 1.0 to 10 g/L, optionally between 1.0 to 5 g/L, optionally between 1.0 to 3 g/L.

A further important condition is the protein concentration in the aqueous phase and accordingly the complex formation between the ligand and the compound selected from one or more of PA, PI, LipO and PPO is carried out in aqueous phase having a protein concentration corresponding to the sum of PA, PI, LipO and PPO of at least 2 g/L g/L. optionally at least 4 g/L, optionally at least 7 g/L, optionally at least 8 g/L, optionally at least 9 g/L, optionally between 2 to 22 g/L, optionally between 3 to 20 g/L, optionally between 5 to 15 g/L, optionally between 6 to 12 g/L, optionally between 7 to 11 g/L.

Following these conditions, in an embodiment, the complex formed between the mobile solubilized ligand and the compound selected from one or more of PA, PI, LipO and PPO comprise between 0.01 mg to 0.5 mg, optionally 0.03 mg to 0.3 mg, optionally 0.05 mg to 0.3 mg complexed polymer per mg complexed protein. In a further embodiment, the complex formed between the mobile solubilized ligand and the compound selected from one or more of PA, PI, LipO and PPO comprise between optionally 1 mg to 30 mg complexed polymer per mg complexed protein, such as between 2 mg to 25 mg, such as between 4 mg to 20 mg, such as between 6 mg to 16 mg, such as between 7 mg to 15 mg.

Separation of Compound-Mobile Solubilized Ligand Complex from Supernatant

When the complex between the mobile solubilized ligand and compound is formed, the complex is separated and/or isolated from the aqueous phase and this separation is preferably achieved by changing the physico-chemical conditions in the aqueous phase to reduce the solubility of the complex in the aqueous phase, preferably so that the complex solidifies of precipitates from the aqueous supernatant.

In an embodiment, the changing of the physico-chemical conditions comprises adjusting the pH, optionally to between 2 to 6, optionally to between 3 to 6, optionally between 3.5 to 5.5, optionally between 4.0 to 5.0. In a particular embodiment, the changing of the physico-chemical conditions comprises adjusting the pH to between 3.5 to 4. In another embodiment, the changing of the physico-chemical conditions comprises adjusting the pH to between 5 to 6. In a still further embodiment the changing of the physico-chemical conditions comprises adjusting the pH to between 5 to 9, such as between 5.5 to 8.0, such as between 5.8 to 7.5.

In a further embodiment, the changing of the physico-chemical conditions comprises adjusting the conductivity and/or the ionic strength, for example by adding salts such as sodium chloride or calcium chloride.

In a further embodiment, the changing of the physico-chemical conditions comprises adding an organic solvent, such as ethanol.

In a further embodiment, the changing of the physico-chemical conditions comprises adjusting the temperature.

In a further embodiment, the changing of the physico-chemical conditions comprises a combination of one or more of adjusting pH, adjusting conductivity, adjusting the temperature and adding organic solvent.

When the complex between the mobile solubilized ligand(s) and the compound(s) has separated from the aqueous supernatant by precipitation, the precipitated complex is separated from the aqueous supernatant phase preferably by a mechanical separation process selected from one or more of membrane separation and centrifugal separation.

The membrane separation process is in one embodiment a continuous membrane separation process, such as a cross flow, a dynamic or a tangential flow membrane separation process. Such membrane separation methods are well known to the skilled person. Suitable membrane separation processes include but is not limited to employing a membrane module selected from one or more of tubular membranes, hollow fibre membranes, spiral wound membranes and plate and frame membranes. Suitable membrane materials for such membrane modules include but is not limited to one or more of ceramics, metal, synthetic polymers and natural polymers. In an embodiment, the membrane is a polyether sulfone membrane or an esterified cellulose membrane. In another embodiment, the membrane process is a filtration process such as a dead-end filtration process.

When employing a membrane module with a hollow fibre membrane the separation process is preferably performed at the following conditions:
pH of the aqueous phase of between 2 to 6.
Feed pressure of between 9 to 15 psi
Backwash pressure of between 9 to 15 psi.
Temperature of the aqueous phase of between 5° C. to 30° C.

When employing a membrane module with a spiral wound membrane the separation process is preferably performed at the following conditions:
pH of the aqueous phase of between 2 to 6.
Feed pressure of less than 120 psi
Backwash pressure of between 20 to 40 psi.
Temperature of the aqueous phase of between 5° C. to 45° C.

When employing a membrane module with a ceramic tubular membrane the separation process is preferably performed at the following conditions:
pH of the aqueous phase of between 3 to 7.
Feed pressure of 60 to 100 psi
Backwash pressure of between 10 to 30 psi.
Temperature of the aqueous phase of between 5° C. to 40° C.

Once the precipitated complex has been retained from aqueous supernatant by the membrane is may be subjected to a diafiltration step by adding further solvent to the feed stream.

The centrifugal separation process involves in an embodiment a centrifuge and/or a liquid cyclone separator. The centrifugal acceleration employed is preferably between 500 to 5000 G, optionally between 1000 to 4000 G, optionally between 1500 to 3000 G and the centrifugal separation process is preferably a continuous process, optionally having a retention time of less than 30 min, optionally less than 15 min, optionally less than 10 min, optionally less than 5 min, optionally less than 3 min, optionally less than 2 min. The centrifuge of liquid cyclone separator preferably is designed to have a flow rate capacity of more than 50 L/min, optionally more than 100 L/min, optionally more than 200 L/min, optionally more than 300 L/min, optionally more than 400 L/min, optionally more than 500 L/min, optionally between 50 to 1000 L/min, optionally between 100-750 L/min, optionally between 75 to 400 L/min.

Where the centrifugal separation process involves a liquid cyclone separator, the liquid cyclone separator is preferably a multistage separator comprising at least two serial hydrocyclones, optionally at least three serial hydrocyclones, optionally at least four serial hydrocyclones.

Cyclonic separation is a method of removing particulates from an air, gas or liquid stream, without the use of filters, through vortex separation. When removing particulate matter from liquids, a hydrocyclone is used. Rotational effects and gravity are used to separate mixtures of solids and fluids. A high-speed rotating liquid flow is established within a cylindrical or conical container called a cyclone. Flows in a helical pattern, beginning at the top (wide end) of the cyclone and ending at the bottom (narrow) end before exiting the cyclone in a straight stream through the center of the cyclone and out the top. Larger (denser) particles in the rotating stream have too much inertia to follow the tight curve of the stream, and strike the outside wall, then drop to the bottom of the cyclone where they can be removed. In a conical system, as the rotating flow moves towards the narrow end of the cyclone, the rotational radius of the stream is reduced, thus separating smaller and smaller particles.

In a further embodiment, the mechanical separation method is capable of retaining compounds having a size of more than 50 kDa, optionally having a size of more than 75 kDa, optionally having a size of more than 100 kDa, optionally having a size of more than 125 kDa, optionally having a size of more than 150 kDa.

Redissolution of Precipitated Complex

When the precipitated complex has been separated from the aqueous supernatant, the compound(s) in the complex may advantageously be further purified and/or separated by mixing the precipitated complex with a substance capable of extracting one or more compounds selected from PA, PI, LipO, PPO, glycoalkaloid and phenolic compounds from the complex and isolating the one or more compounds selected from PA, PI, LipO, PPO, glycoalkaloid and phenolic compounds by a mechanical separation process concentrating the one or more compounds selected from PA, PI, LipO, PPO, glycoalkaloid and phenolic compounds in the retentate.

In a preferred embodiment, the substance is an aqueous solvent, optionally having, an increased pH and optionally an increased conductivity and/or ionic strength compared to the aqueous supernatant phase from which the complex separated.

In a specific embodiment, the aqueous solvent has a pH between 7 to 14 and optionally a conductivity between 10 mS/cm to 200 mS/cm. In a further embodiment to avoid cost of chemicals and waste effluent treatments the aqueous solvent has a conductivity 0.1 mS/cm and 10 mS/cm.

The substance may also be a solid substance increasing the pH in the isolated complex. Such solid substances include but is not limited to solid substance is selected from one or more of oxides, hydroxides, phosphates, carboxylates and ammonia, optionally in the form of salts of ammonium or metals, such as sodium, potassium, calcium, magnesium.

The mechanical separation process concentrating the one or more compounds selected from PA, PI, LipO, PPO, glycoalkaloid and phenolic compounds in the retentate, may be selected from the membrane separation and centrifugal separation processes described, supra.

Selective Elution of Undesired Compounds

When the precipitated complex has been isolated/separated from the aqueous supernatant, the compound(s) in the complex may advantageously be further purified and/or separated by incorporating a step of selective elution. The selective elution step releases one or more compounds associated with the isolated complex, compounds which are typically entrapped in the solid complex matrix or bound to a moiety of the ligand or the complexed compound or comprised in liquid remaining in the complex. Besides impurities from the plant juice the eluted compound(s) may be selected from one or more of glycoalkaloid, phenolic compounds, PPO, PA, LipO, PI and the ligand. In an embodiment, the eluted compound(s) may be selected form one or more of glycoalkaloid, LipO, phenolic compounds, PPO and the ligand. In a further embodiment, the eluted compound(s) may be selected form one or more of PA and PI. In a further embodiment, the eluted compound(s) may be selected from one or more of PPO, PA and PI.

The selective elution is preferably performed by contacting the isolated complex with a solvent which releases the compound and the solvent is preferably an aqueous solvent, optionally wherein conditions are selected from pH 1 to pH 6, optionally from pH 6 to 9, optionally from pH 6.5-8.5, optionally from pH 7 to 8 and a conductivity between 1 mS/cm to 300 mS/cm optionally from pH 2 and a conductivity between 10 mS/cm to 200 mS/cm, optionally from pH 3 to pH 4.5 and a conductivity between 50 mS/cm and 100 mS/cm, optionally from pH 4.6 to pH 5 and a conductivity between 25 mS/cm to 250 mS/cm. Carefully selecting these conditions influences which compounds are eluted and in which amounts. The solvent may also comprise or consist of an organic solvent, optionally selected from one or more of alcohols, glycols, esters, ethers, amines, aromatic acids, alkyl acids such as methanol, ethanol, propanol, polyethylene glycol, (PEG), propylene glycol (PG), monopropylene glycol (MPG), glycerol, benzoic acid, hexanoic acid, octanoic acid and derivatives of these. The solvent may further comprise a surfactant, preferably selected from one or more of non-ionic surfactants, anionic surfactants, cationic surfactants, zwitterionic or amphoteric surfactants. Examples of useful surfactants are Sodium Dodecyl Sulphate, Tween 20 and cetyl trimethyl ammonium bromide. In one embodiment, the eluted compound is PI and the solvent is an aqueous solution of sodium chloride at a concentration between 0.2 M to 2 M, optionally a concentration between 0.3 M to 1 M, optionally a concentration between 0.4 M to 0.8 M, optionally a concentration between 0.45 M to 0.65 M. In a further embodiment the aqueous solvent further comprises a buffer having a pH between pH 1 to pH 4.5, optimally a pH between 2 to pH 4.0, optionally a pH between pH 2.5 to pH 3.6. In a further embodiment, the aqueous solvent comprises a salt, optionally selected from alkali or earth alkali metal salts of chloride, nitrate, nitrite sulphate, sulphite, phosphate, acetate or citrate.

Further Method Steps

The isolated compound(s) selected from one or more of PA, PI, LipO, PPO, glycoalkaloid and phenolic compounds may be subjected to further processing steps for preparing a finished product applicable to a desired use.

In one embodiment, the isolated compound(s), whether in solid or dissolved form, is subjected to a microbial control step. This micro control step may comprise adding an agent to the compound(s) selected from one or more of bactericidal agents, bacteriostatic agent, fungicidal agents and fungistatic agents. An addition or alternatively the microbial control step may also comprise operations selected from one or more of heating, irradiating and filtering.

The isolated compound(s) may still be bound to the ligand and the ligand may in some applications provide additional functionality, while in other applications being unwanted. Accordingly, in one embodiment, the method of the invention further comprises a step of separating the one or more of PA, PI, LipO, PPO, glycoalkaloid and phenolic compounds from the ligand.

The isolated compound(s) may also still possess certain properties, which in some applications may be unwanted, for example enzymes activity. Accordingly, in an embodiment the method of the invention further comprises a step of inactivating the one or more of PA, PI, LipO and PPO, optionally irreversibly inactivating the said compounds. Such inactivation may for example be achieved by denaturation, such as thermal or solvent denaturation.

The isolated compound(s) may also be processed into a formulation which is suitable for its use and its distribution. The form may also be beneficial for its stability and/or shelf life. Accordingly, in an embodiment the method of the invention comprises forming the isolated compound(s) complex into a formulation selected from powders, pastes, slurries or liquids. The powder may in a preferred embodiment be made from known methods including drying, spray drying, spray cooling or prilling, (fluid bed) coating, extrusion, mixer granulation, core absorption, lyophilization, flash freezing, microgranulation, encapsulation or microencapsulation.

If the formulation form is a liquid, it is considered important for the stability to keep the water activity under control. Accordingly, in an embodiment the water activity, aw, of the formulation is below 0.9, optionally below 0.7, optionally below 0.6. The water activity can be reduced by adding a mono- or disaccharide to the formulation, such as mono- or disaccharide is selected from one or more of glucose, fructose, sucrose and lactose. The water activity may also be reduced by adding a dextrin derived from starch. For further stabilization, the formulation may be added stabilizing agents, optionally selected from one or more antioxidants, reducing agents, PVP, PVA and PEG.

Spray drying is to be understood as when a liquid solution of compound is atomized in a spray drying tower to form small droplets which during their way down the drying tower dry to form a particulate material containing the compound. Very small particles can be produced this way (Michael S. Showell (editor); Powdered detergents; Surfactant Science Series; 1998; vol. 71; page 140-142; Marcel Dekker).

Coating is to be understood as when wherein the compounds is coated as a layer around a pre-formed inert core particle, wherein a solution containing the compound is atomized, typically in a fluid bed apparatus wherein the pre-formed core particles are fluidized, and the solution adheres to the core particles and dries up to leave a layer of dry compound on the surface of the core particle. Particles of a desired size can be obtained this way if a useful core particle of the desired size can be found. This type of product is described in e.g. WO 97/23606.

Core absorption is to be understood as when the compound is absorbed onto and/or into the surface of a porous core particle. Such a process is described in WO 97/39116.

Extrusion or pelletation is to be understood as when a paste containing the compound is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the paste, which may be harmful to the compound. (Michael S. Showell (editor); Powdered detergents; Surfactant Science Series; 1998; vol. 71; page 140-142; Marcel Dekker).

Prilling or spray cooling is to be understood as when compound is suspended in molten wax and the suspension is sprayed, e.g. through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the compound is uniformly distributed throughout an inert material instead of being concentrated on its surface. Also U.S. Pat. Nos. 4,016,040 and 4,713,245 are documents relating to this technique.

Mixer granulation is to be understood as when a liquid containing the compound is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the compound. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of the compound, fillers and binders etc. are mixed with cellulose fibers to reinforce the particles.

Unit Operations for Carrying Out the Method of the Invention

The method of the invention is very applicable to industrial scale processes of plant materials. Accordingly, the formation of the complex in the aqueous phase is preferably carried out in a reactor having a volume of at least 500 L, optionally at least 1000 L, optionally at least 4000 L, optionally at least 8000 L optionally at least 15000 L optionally at least 25000 L, said reactor optionally equipped with means for thermal control and agitation. In an embodiment, the reactor is a continuous reactor or a batch reactor. The means for agitation may include stirring, shaking, rotation, vibrating or pumping, while the means for thermal control may involve heating sources selected from steam, electricity and fuel and cooling sources from liquid or gas cooling.

PH Adjustment and Precipitation

As disclosed in the Examples, one way of carrying out the present invention may be as described in Example 32. Thus, the present invention relates to e.g. how to isolate a PA enriched fraction with pH adjustment from pretreated potato juice (with water glass). This show that an aqueous phase comprising compounds selected from two or more of PA, PI, PPO, LipO, pectin, lipid, glycoalkaloid and phenolic compounds of which at least one compound is selected from PA, PI, LipO and PPO with a true protein concentration for example 11 g/L can be pre-treated by addition of a water glass solution followed by incubation. The sample may then be centrifuged and the supernatant collected.

The precipitate may then be washed by resuspension in water pH adjusted to 3.0 with hydrochloric acid and repeated centrifugation (precipitate 1). The precipitate may then be then suspended in water and pH may then be slowly adjusted to pH 9 with 1 M NaOH during mixing at ambient temperature.

Figure 22:
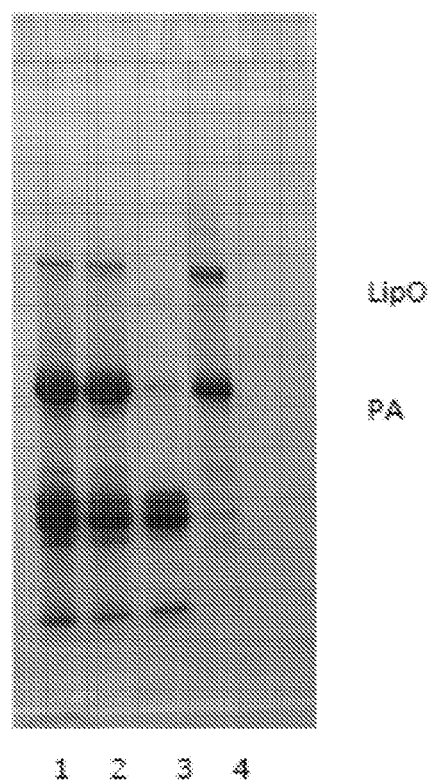

The SDS-PAGE of FIG. 22 illustrates that the supernatant from the pH precipitation (see lane 3) contains only a very small fraction of the PA compared to the starting material. The major part of PI is still in solution resulting in a highly enriched PI fraction (see lane 3, strong PI bands). The dissolved precipitate contains PA and only an insignificant fraction of PI resulting in a highly enriched PA product, see lane 4. The low turbidity of test solution 3 (containing the non-precipitated PI fraction) is highly advantageous for further processing e.g. by membrane filtration or an additional precipitation step.

When compared to a corresponding dissolved precipitate containing PA from a potato juice that is not pre-treated according to the invention, test solution 4 would have significantly better re-solubilization characteristics and a lower turbidity.

In one embodiment of the invention the aqueous phase in step b) is adjusted to a pH below pH 5.5, such as below pH 5.0, such as below pH 4.5, such as below pH 4.0

In one embodiment of the invention the aqueous phase in step b) is adjusted to a pH in the range of pH 1-5.5, such as in the range of pH 1.5-5.0, such as in the range of 2.0-4.5, such as in the range of pH 2.0-3.8, such as in the range of pH 2.5-3.5.

In certain product applications, it is of interest to separate lipoxygenase from PI without completely separating PA from PI. Thus, in one embodiment of the invention the aqueous phase in step b) is adjusted to a pH in the range of pH 3.0-5.0, such as in the range of pH 3.0-4.5, such as in the range of pH 3.3-4.2, whereby Lipoxygenase in the resulting precipitate is separated from PI in the remaining aqueous phase.

An aspect of the present invention relates to a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 5 percent and to achieve an optical density at 620 nm of the remaining aqueous phase of less than 0.7;
  c) adjusting pH of the remaining aqueous phase (from step b)) to allow the formation of a precipitate comprising PA; and
  d) isolating the precipitate from the aqueous phase.

An aspect of the present invention relates to a method as described herein, which method after step b) comprises the steps of;
  f) adjusting pH of the remaining aqueous phase (from step b)) to allow the formation of a precipitate comprising PA;
  g) isolating the precipitate from the aqueous phase.

In one embodiment of the invention the pH of the aqueous phase in step b) is adjusted to a pH in the range of 5-9.

In one embodiment of the invention the isolated precipitate in step c) is dissolved by adjusting pH to a pH above pH 5 such as a pH above pH 6, such as a pH above 7 such as a pH in the range of pH 5-10, such as in the range of 6-9, such as in the range of pH 6.5-8.5.

In one embodiment, the invention relates to a method, wherein the pH of the aqueous phase in step b) is adjusted to a pH in the range of 5-9, preferably in the range of 6-8.

In one embodiment, the dissolved precipitate is treated to further increase the purity of the PA.

In one embodiment, the dissolved precipitate is clarified by centrifugation and/or filtration.

In one embodiment the dissolved precipitate is re-precipitated by changing pH. This may be repeated several times as part of a washing process to achieve a higher purity of PA.

In one embodiment, the dissolved precipitate is added a soluble silicate and pH adjusted (if necessary) to achieve the precipitation of unwanted impurities.

In one embodiment, the dissolved precipitate is added a divalent or trivalent metal ion and pH adjusted (if necessary) to achieve the precipitation of unwanted impurities.

In one embodiment, the dissolved precipitate is treated with a solid phase adsorbent to adsorb unwanted impurities.

In one embodiment, the dissolved precipitate is treated with a solid phase adsorbent to adsorb glycoalkaloids and/or phenolic compounds.

In one embodiment, the dissolved precipitate is subjected to a membrane filtration process to separate PA in the retentate from unwanted impurities in the permeate In one embodiment, the membrane filtration process is a tangential flow ultrafiltration process employing a membrane having a nominal pore size in the range of approx. 10,000-200,000 kDa, such as in the range of approx. 30,000-150,000 kDa, such as in the range of approx. 50,000-100,000 kDa In one embodiment of the invention the isolation of PI in step d) of the methods of the present invention above comprise subjecting the remaining aqueous phase to a solid phase adsorption step thereby adsorbing the PI and separating it from the aqueous phase.

In one embodiment of the invention the solid phase adsorption is performed using an adsorbent having negatively charged ligands such as ion exchanging ligands including carboxylic acid, sulfonic acid and phosphonic acid ligands.

In one embodiment of the invention the solid phase adsorption is performed using an adsorbent having aromatic acid ligands attached thereto.

In one embodiment of the invention the solid phase adsorbent comprises a benzoic acid, a carboxymethyl benzene, a benzene sulfonic acid or a (sulfomethyl) benzene ligand or derivatives hereof.

In one embodiment of the invention the isolation of PI in step d) of the methods of the present invention above comprise subjecting the remaining aqueous phase to a membrane filtration process separating PI in the retentate from at least one of lipid, glycoalkaloid and phenolic compounds in the permeate.

In one embodiment of the invention said membrane filtration process is a tangential flow ultrafiltration process.

In one embodiment of the invention said ultrafiltration process is performed using a membrane having a nominal pore size (cut-off value) of less than 50,000 D, such as less than 30,000 D. In one embodiment, the membrane has a nominal pore size of about 10,000 D.

In one embodiment of the invention the ultrafiltration process is performed at a pH value in the range of pH 1-6, such as pH 1.5-5.0, such as pH 2.0-4.5, such as pH 2.5-4.0 such as pH 3.0-4.0, such as pH 1.5-2.5.

In one embodiment of the invention the ultrafiltration process is performed at a pH value in the range of pH 0.1-1.0, such as pH 0.5-0.9, In one embodiment of the invention the isolation of PI in step d) of the methods of the present invention above comprise subjecting the remaining aqueous phase to a solid phase adsorption step thereby adsorbing glycoalkaloids and phenolic compounds and separating it from the aqueous phase.

In one embodiment of the invention the isolation of PI in step d) of the methods of the present invention comprise subjecting the PI retentate after the ultration process to a solid phase adsorption step thereby adsorbing glycoalkaloids and phenolic compounds and separating it from the PI retentate.

In one embodiment of the invention the solid phase adsorption is performed by contacting the remaining aqueous phase or the PI retentate with a solid phase adsorbent selected from the group of activated carbon, layered silicate adsorbents and porous synthetic polymers.

In one embodiment of the invention the porous synthetic polymer is a hydrophobic adsorbent In one embodiment of the invention the porous synthetic polymer is a hydrophobic adsorbent comprising a cross-linked aromatic backbone such as a cross-linked vinyl benzene backbone.

In one embodiment of the invention the porous synthetic polymer is a Dowex, Lewatit or Amberlite adsorbent.

In one embodiment of the invention the isolation of PI in step d) of the methods of the present invention above comprise subjecting the remaining aqueous phase to a precipitation step thereby precipitating the PI and separating it from the aqueous phase.

In one embodiment of the invention said precipitation step comprise the addition of a precipitation agent to the remaining aqueous phase.

In one embodiment of the invention said precipitation agent comprise one or more compounds selected from lyotropic salts, anionic polymers, silicates, polyphosphates, organic solvents.

In one embodiment of the invention said precipitation is performed at a pH in the range of 0.1-5.0, such as a pH in the range of 0.7-4.9, such as a pH in the range of 1.0-4.5, such as a pH in the range of 1.5-4.0, such as a pH in the range of 1.9-3.6, such as a pH in the range of 2.5-3.5, such as a pH in the range of 3.5-4.5.

Membrane Filtration

An aspect of the present invention relates to a method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) performing one or more steps to reduce the concentration of solanine in the dry matter of the aqueous phase with at least 5 percent and to achieve an optical density at 620 nm of the remaining aqueous phase of less than 0.7; and c) subjecting the remaining aqueous phase (from step b) of the methods of the present invention) to a membrane filtration process separating at least one of PA and PI in the retentate from at least one of PA, PI, LipO, PPO, pectin, lipid, glycoalkaloid and phenolic compounds in the permeate.

In one embodiment of the present invention is the concentration of solanine in the dry matter of the aqueous phase reduced with at least 10%, such as at least 20%. The reduction may be at least 25%.

An aspect of the present invention relates to a method as described herein, which method after step b) comprises the step of;

h) subjecting the remaining aqueous phase (from step b) of the methods of the present invention) to a membrane filtration process separating at least one of PA and PI in the retentate from at least one of PA, PI, LipO, PPO, pectin, lipid, glycoalkaloid and phenolic compounds in the permeate.

Aqueous Phase and Plant Material

The aqueous phase of the invention is typically a crude fraction or stream from industrial processing of plant materials. It may be undiluted aqueous juices directly obtained from shredding, crushing, squeezing and/or pressurizing plant materials or it may also result from adding an aqueous solvent to the plant material and extracting water soluble compound therefrom. To avoid generating excess waste water the method of the invention is advantageously capable of employing undiluted plant juices directly obtained from and released from disintegrating the plant material. The plant material can be any plant material comprising the compounds of the invention, such as the tuber portion of a plant of the genus *Solanum*, in particular the species *S. tuberosum* (potato). Accordingly, in an embodiment the aqueous phase of the invention comprise an aqueous solution liberated when disintegrating a portion of a plant optionally a tuber portion of a plant of the genus *Solanum*, optionally of the species *S. tuberosum*. In another embodiment, the aqueous phase of the invention consists of an aqueous solution liberated when disintegrating a portion of a plant optionally a tuber portion of a plant of the genus *Solanum*, optionally of the species *S. tuberosum*. In a further embodiment the aqueous phase of the invention comprise the aqueous solution liberated when disintegrating the plant material diluted with less than 50 wt % added solvent, optionally less than 25 wt % added solvent, optionally less than 20 wt % added solvent, optionally less than 15 wt % added solvent, optionally less than 10 wt % added solvent, optionally less than 5 wt % added solvent, optionally less than 2 wt % added solvent, optionally less than 1 wt % added solvent.

The aqueous phase of the invention comprises in an embodiment at least 3 grams protein per litre, optionally at least 5 g/L, optionally at least 8 g/L, optionally at least 10 g/L, optionally at least 12 g/L, optionally between 5 to 25 g/L, optionally between 6 to 20 g/L, optionally between 7 to 15 g/L, optionally between 8 to 12 g/L, optionally between 9 to 11 g/L.

In an embodiment of the invention 30 to 50% of the protein in the aqueous phase is PA, while in another embodiment 30 to 50% of the protein in the aqueous phase is PI. Particularly, at least 60% of the protein in the aqueous phase is PA or PI.

The aqueous phase of the invention further comprises in an embodiment at least 50 mg/kg of glycoalkaloid, optionally at least 75 mg/kg, optionally at least 100 mg/kg, optionally at least 125 mg/kg, optionally at least 150 mg/kg, optionally at least 175 mg/kg, optionally at least 200 mg/kg, optionally at least 250 mg/kg, optionally at least 300 mg/kg, optionally between 50-400 mg/kg, optionally between 75-350 mg/kg, optionally between 100-300 mg/kg of glycoalkaloid. Further, the aqueous phase of the invention further comprises in an embodiment, at least 10 mg/kg of phenolic compound, optionally at least 25 mg/kg, optionally at least 50 mg/kg, optionally at least 125 mg/kg, optionally at least 170 mg/kg, optionally at least 225 mg/kg, optionally at least 300 mg/kg, optionally at least 400 mg/kg, optionally at least 600 mg/kg, optionally between 25 to 2000 mg/kg, optionally between 75 to 1500 mg/kg, optionally between 200 to 1000 mg/kg phenolic compounds.

In one embodiment of the invention the aqueous phase in step a) of the methods of the present invention is potato fruit juice obtained from industrial manufacture of potato starch.

In one embodiment of the invention the fruit juice is further treated in a defoamer to substantially reduce the amount of foam in the fruit juice.

In one embodiment of the invention the fruit juice has been treated to substantially reduce the amount of insoluble substances in the fruit juice prior to pH adjustment in step b) of the methods of the present invention.

In one embodiment of the invention the fruit juice is pH adjusted by an in-line mixing with an acid.

In one embodiment of the invention the fruit juice has been added an antioxidant, such as sodium bisulfite or sodium sulfite.

In one embodiment, the fruit juice has a total true protein concentration of at least 5 g/L such at least 6 g/L, such as at least 7 g/L, such as at least 8 g/L fruit juice.

In one embodiment, the aqueous phase is a root or tuber juice, also known herein as fruit juice.

In one embodiment, the juice is potato juice.

One embodiment of the present invention relates to a root or tuber juice, obtainable by a method according to the present invention, comprising at least 0.5 wt. % of dissolved protein, wherein the protein is native and wherein the clarity, expressed as OD620, is less than 0.8.

In one embodiment, the root or tuber juice does not comprise an acrylic polymer.

In industrial processing of plant materials, it is desired to avoid costly and mechanically complicated steps such as removal of peelings from the inner portions of the plant material. However, peelings may contain considerable amounts of undesired compounds, such as glycoalkaloid and phenolic compounds, and one advantage of the present invention is that the method works surprisingly well also for crude plant juices. Accordingly, in one embodiment the plant portion is unpeeled before disintegration, and optionally the aqueous solution includes juices from plant peelings as well. It may however be desirable after disintegrating the plant material and before precipitating the complex to separate insolubles, such as suspended fibres and inorganic solids from the plant juice and/or aqueous phase and accordingly in an embodiment the method of the invention further comprises separating insoluble solid components, including suspended fibres, of the disintegrated plant portion from the aqueous solution liberated from the plant material.

Applications of the Methods and Products

The invention also provides a composition comprising the isolated one or more compounds of patatin protein (PA), protease inhibitor protein (PI), lipoxygenase (LipO) and polyphenol oxidase (PPO), glycoalkaloid and phenolic compounds obtainable from the method of the invention. The composition may also in an embodiment comprise the ligand bound to the compound(s). Accordingly, the composition may comprise at least 25%, optionally at least 50%, optionally at least 75% of the ligand contained in the complex formed between the compound(s) and the ligand. Preferably the composition comprises one or more of PA, PI and PPO.

The composition of the invention may be an additive for one or more of foods, animal feeds, pet foods, beverages, cosmetics, pharmaceuticals, nutraceuticals, dietary supplements and fermentations. Additives for food or beverage include additives for meats, confectionary, bread, dairy, ready-to-eat food, senior nutrition products and sports foods and drinks. Additives for animal feed includes additives for poultry feed, ruminants feed, pig feed, horse feed, fish feed and insect feed. Additives for pet food include additives for canine or feline pet foods. Additives for cosmetics include additives for lotions, creams, gels, ointments, soaps, shampoos, conditioners, antiperspirants, deodorants, mouth wash, contact lens products and foot bath products. Additives for dietary supplements include additives for protein supplements and senior nutrition products. Additives for fermentations include additives for bacterial, fungal and yeast fermentations.

In further embodiments, the composition of the invention may be selected from one or more of food or beverages, animal feeds, pet foods, cosmetics, pharmaceuticals, nutraceuticals, dietary supplements and fermentation broths.

In an embodiment, the composition is a cosmetic composition comprising glycoalkaloid, optionally for use as an exfoliant.

In another embodiment, the composition is a pharmaceutical composition comprising glycoalkaloid for use as a medicament, preferably a medicament for treating cancer.

Depending on the ligand and the conditions chosen the complex may comprise different compounds bound to the ligand. In an embodiment, the compound is a protein and a particularly complex of the invention may comprise one or more of PA, PI, LipO and PPO.

In one embodiment, the complex comprises, on a dry weight basis, more than 51.9 wt % PA, optionally more than 55 wt % PA, optionally more than 65 wt % PA, optionally more than 75 wt % PA, optionally more than 85 wt % PA, optionally more than 95 wt % PA relative to the total amount of PA, PI, LipO and PPO in the complex. In an alternative embodiment, the complex comprises more than 88.6 wt % PA of total PA, optionally more than 90 wt % PA of total PA, optionally more than 95 wt % PA of total PA, optionally more than 97 wt % PA of total PA, optionally more than 99 wt % PA of total PA.

In another embodiment, the complex comprises, on a dry weight basis, more than 50 wt % PI, optionally more than 55 wt % PI, optionally more than 65 wt % PI, optionally more than 75 wt % PI, optionally more than 85 wt % PI, optionally more than 95 wt % PI relative to the total amount of PA, PI, LipO and PPO in the isolated complex. In an alternative embodiment, the complex comprises more than 90 wt % PI of total PI, optionally more than 95 wt % PI of total PI, optionally more than 97 wt % PI of total PI, optionally more than 99 wt % PI of total PI.

The complex may also comprise, on a dry weight basis, more than 50 wt % PPO, optionally more than 55 wt % PPO, optionally more than 65 wt % PPO, optionally more than 75 wt % PPO, optionally more than 85 wt % PPO, optionally more than 95 wt % PPO relative to the total amount of PA, PI, LipO and PPO in the isolated complex. In an alternative embodiment, the complex comprises more than 90 wt % PPO of total PPO, optionally more than 95 wt % PPO of total PPO, optionally more than 97 wt % PPO of total PPO, optionally more than 99 wt % PPO of total PPO.

The complex may also comprise from 60 to 95 wt % PA; and from 0.9 to 39.9 wt % PI and from 0.1 to 4.1 wt % PPO relative to the total amount of PA, PI, LipO and PPO in the complex.

The complex may also comprise from 80-99.9 wt % PA of total PA in the aqueous phase; from 0.1 to 20 wt % PI of total PI in the aqueous phase and from 0.1 to 20 wt % PPO of total PPO in the aqueous phase.

The PA may be complexed to the ligand in a PA:ligand dry weight ratio of at least 4:1, optionally at least 8:1, optionally at least 10:1, optionally at least 15:1. PI may be complexed to the ligand in a PI:ligand dry weight ratio of at least 3:1, optionally at least 5:1, optionally at least 8:1, optionally at least 10:1. PPO may be complexed to the ligand in a PPO:ligand dry weight ratio of at least 2:1, optionally at least 4:1 optionally at least 7:1

In an embodiment, PA is complexed to the ligand in a PA:ligand dry weight ratio of at least 6:1; the PI is complexed to the ligand in a PI:ligand dry weight ratio of at least 5:1 and the PPO is complexed to the ligand in a PPO:ligand dry weight ratio of at least 2:1, optionally in a PA:ligand dry weight ratio of at least 6:1; a PI:ligand dry weight ratio of at least 7:1 and a PPO:ligand dry weight ratio of at least 2:1.

Using the method of the invention the complex is enriched in PA over PI compared to PA and PI originally in the aqueous phase, characterised by that the PA:PI dry weight ratio in the precipitate is at least 25% higher than the PA:PI dry weight ratio for PA and PI remaining dissolved in the aqueous supernatant phase, optionally at least 50% higher, optionally at least 75% higher.

Using the method of the invention a significant portion of the PA and PI can be isolated from the aqueous phase and in an embodiment the sum of PA and PI remaining dissolved in the aqueous supernatant phase is less than 15 wt. % of the total PA and PI, optionally less than 12%, optionally less than 10%, optionally less than 8%, optionally less than 6%, optionally less than 5%, optionally less than 4%, optionally less than 3%, optionally less than 2%, optionally less than 1%, optionally less than 0.5%.

The method of the invention may also advantageously separate what in some applications are desired compounds such as PA and PI from undesired compounds. Accordingly, in an embodiment the complex contains less than 200 milligram of glycoalkaloid per kilogram dry matter, optionally less than 150, optionally less than 110, optionally less than 95 mg, optionally less than 80, optionally less than 65, optionally less than 45, optionally less than 25, optionally less than 10 milligram glycoalkaloid per kilogram dry matter. Alternatively, at least 50%, optionally at least 65%, optionally at least 75%, optionally at least 82%, optionally at least 89%, optionally at least 93% of the glycoalkaloid in the aqueous phase remains in the aqueous supernatant phase after separation/precipitation of the complex. In a further embodiment, the complex contains less than 300 milligram phenolic compounds per kilogram dry matter. optionally less than 250, optionally less than 200, optionally less than 150, optionally less than 125, optionally less than 95, optionally less than 70, optionally less than 35 milligram phenolic compounds per kilogram dry matter. Alternatively, at least 50%, optionally at least 65%, optionally at least 75%, optionally at least 85%, optionally at least 90% of the phenolic compounds in the aqueous phase remains in the aqueous supernatant phase after separation of the complex.

Particularly, the phenolic compound is chlorogenic acid (CGA). In this context chlorogenic acid is to be understood as being an ester of hydroxycinnamic acid and quinic acid, particularly esters between caffeic acid, ferulic acid or p-coumaric acid with quinic acid or combinations thereof. In an embodiment, the complex comprise, on a dry weight basis, less than 120 mg/kg of chlorogenic acid, optionally less than 100 mg/kg CGA, optionally less than 80 mg/kg CGA, optionally less than 60 mg/kg CGA, optionally less than 40 mg/kg CGA, optionally less than 20 mg/kg CGA, optionally less than 10 mg/kg CGA.

An aspect of the present invention relates to a product obtainable by a method according to the present invention, for use as a feed material, a food ingredient, or in the food or feed industry.

In some cases, the optimal business model for utilizing potato fruit juice is the combined production of a PA product not intended for use as a functional protein and a highly functional PI product, rather than the production of both a functional PA and a functional PI product.

Thus, in one embodiment the isolated precipitate in step c) of the methods of the present invention contains less than 50%, such as less than 40%, such as less than 30%, such as less than 20%, such as less than 10% functional PA.

In one embodiment, the isolated precipitate in step c) of the methods of the present invention contains less than 50%, such as less than 40%, such as less than 30%, such as less than 20%, such as less than 10% PA being soluble by suspension of the precipitate in an aqueous phosphate buffer at 2% dry matter and at pH 7.0.

In one embodiment of the invention the isolated precipitate in step c) of the methods of the present invention is further treated to produce a protein powder as a human nutritional food product. In one embodiment, the precipitate is washed with an aqueous solution of an acid and dried.

In one embodiment of the invention the isolated precipitate in step c) of the methods of the present invention is further treated to produce a protein powder as a functional protein ingredient product for human consumption. In one embodiment, the precipitate is washed with an aqueous solution of an acid and dried.

The invention also provides methods of using the composition comprising the isolated one or more compounds of PA, PI, LipO, PPO, glycoalkaloid and phenolic compounds obtainable from the method of the invention. PA, PI, LipO, PPO, glycoalkaloid and phenolic compounds have a wide range of applications in particular in the food/feed/nutrition and health industry, since they may provide one or more functions selected from foam control, emulsion control, control of proteolytic activity, nutritional improvement, gelation, solubility improvement, organoleptic improvement, allergenicity reduction, oxidation, exfoliation and treatment of diseases such as cancer.

The invention also provides packaging means for containing the compositions of the invention. Accordingly, a container is provided comprising the composition of the invention.

Ligand Compositions

The invention further provides a polymer having aromatic or heteroaromatic acid ligands covalently attached. The polymer may be natural or synthetic and the polymer is preferably soluble in aqueous solvent above pH 6 and preferably insoluble below pH 5.9. optionally below pH 5.5, optionally below pH 5.0, optionally below pH 4.8, optionally below pH 4.5, optionally below pH 4.2, optionally below pH 4.0, optionally below pH 3.5. In an embodiment, the polymer comprises a soluble polysaccharide, such as starch, reacted with a bifunctional reagent for attachment of ligands. The bifunctional reagent may be chosen from one or more of epichlorohydrin, allyldiglycidyl ether, allyl bromide and divinyl sulfone. The aromatic or heteroaromatic acid is preferably chosen from one or more of hydroxybenzoic acid, aminobenzoic acid, mercaptobenzoic acid and derivatives hereof.

EXAMPLES

Materials & Methods:

Chemicals used in the examples herein e.g. for preparing buffers and solutions are commercial products of at least reagent grade.

Water used for conducting the experiments is all deionized water.

Aqueous Solutions Comprising PA, PI, PPO, Glycoalkaloid and Polyphenol

Potatoes of the variety Folva are obtained from a local supermarket.

The potatoes are washed and their surface are dried off before the potatoes are shredded with the peel while the liberated liquid (juice) concomitantly is separated from the main mass of insolubles using a commercial juicer (Nutrijuicer PRO) without diluting with water.

10 ml sodium sulphite (10 wt %) per 1000 ml juice is added immediately to the juice and the juice is centrifuged for 10 min at 1430 G to remove any remaining large insoluble particles such as fibers and starch.

10 kg of potatoes yields about 4.65 L of centrifuged juice (test solution 1) with a pH of 6.2 and a conductivity of 10.7 mS/cm, measured with a Seven2Go S3 conductivity meter from Mettler Toledo, Switzerland.

Mobile Polymeric Ligand Preparations a) Sodium alginate is obtained from Sigma Aldrich, USA (cat. no.: W201502). 15 g of sodium alginate is added up to 1 L of water and the alginate is solubilized by magnetic stirring yielding a 1.5 wt % sodium alginate solution (ligand solution A).

b) Kappa carrageenan is obtained from Sigma Aldrich, USA (cat. no.: C1013). 15 g of kappa carrageenan is added up to 1 L of water and the kappa carrageenan is solubilized by magnetic stirring yielding a 1.5 wt % kappa carrageenan solution (ligand solution B).

c) Iota carrageenan is obtained from Sigma Aldrich, USA (cat. no.: C1138) 15 g of iota carrageenan is added up to 1 L of water and the iota carrageenan is solubilized by magnetic stirring yielding a 1.5 wt % iota carrageenan solution (ligand solution C)

d) Lambda carrageenan is obtained from Sigma Aldrich, USA (cat. no.: 22049). 15 g of lambda carrageenan is added up to 1 L of water and the lambda carrageenan is solubilized by magnetic stirring yielding a 1.5 wt % lambda carrageenan solution (ligand solution D)

e) Polyacrylic acid ($PAA_{450}$) having average MW of 450,000 kDa, is obtained from Sigma Aldrich, USA (cat. no.: 181285). 1.5 g of $PAA_{450}$ is added up to 100 mL of water and the PAA is solubilized by magnetic stirring yielding a 1.5 wt % $PAA_{450}$ solution (ligand solution E).

f) Polyacrylic acid ($PAA_{15}$), having an average MW of 15,000 kDa and in a 35 wt % aqueous solution, is obtained from Sigma Aldrich, USA (cat. no.: 416037). 10 ml of the 35 wt % aqueous solution of $PAA_{15}$ is diluted with 223.3 ml water and mixed by magnetic stirring, yielding of 1.5 wt % $PAA_{15}$ solution (ligand solution F).

Buffer Solutions

A 10 wt % sodium sulphite buffer solution is prepared by dissolving 10 g of sodium sulphite from Sigma Aldrich USA (cat. No.: 13471) in 100 mL water. pH was not adjusted. Measured to pH 7.7.

A 0.1 M di-potassium hydrogen phosphate pH 7.0 buffer solution is prepared by dissolving 17.42 g di-potassium hydrogen phosphate from Sigma Aldrich USA (cat. no.: P3786) in 900 ml water followed by adjusting pH to 7.0 with 4 M hydrochloric acid. Finally, water is added to 1 L.

A 0.1 M pyrocatechol in 0.1 M di-potassium hydrogen phosphate pH 7.0 (for PPO detection) is prepared by dissolving 11.01 g pyrocatechol from Sigma Aldrich, USA (cat. no.: C9510) in 100 ml 0.1 M di-potassium hydrogen phosphate pH 7.0

SDS-PAGE Electrophoresis Reagents a) LDS sample buffer, 4× is obtained from Expedeon, USA (Cat. no.: NXB31010)
b) SDS Run buffer, 20× is obtained from Expedeon, USA (Cat. no.: NXB50500)
c) Precast 4-20% gradient gels are obtained from Expedeon, USA (Cat. no.: NXG42012K)
d) Instant Blue Coomassie staining solution is obtained from Expedeon, USA (Cat. no. ISB1L).

Assays a) SDS-PAGE Electrophoresis

The samples produced in each example are analyzed using SDS-PAGE gel electrophoresis showing the protein composition in each sample. The SDS-PAGE gel electrophoresis is performed using an electrophoresis apparatus and precast 4-20% gradient gels from Expedeon USA (Cat. no.: NXG42012K). The protein samples are mixed with LDS sample buffer and incubated for 10 minutes at 70° C. The samples are applied to a precast gel and proteins are allowed run for one hour at 200 V 90 mA in the SDS Run buffer at non-reduced running conditions. The gel is developed in the staining solution for three hours and the protein bands are evaluated by visually inspection or analyzed by scanning densitometry to quantify the amount of specific proteins in the test solutions.

b) Dry Matter Determination

A Sartorius moisture analyzer (MA37, Sartorius) is used to determine dry matter in a sample by applying 5-10 mL of a sample to the instrument. The sample is then dried at 110° C. until constant weight and the remaining dry matter is determined and calculated by the instrument.

c) Semi-Quantitative Determination of Polyphenol Oxidase (PPO) Activity.

A sample is mixed with a pyrocathecol solution pH 7.0 at ambient temperature. If the sample contains PPO the solution changes color from colorless to orange within 15 minutes. The color intensity obtained after 15-minute incubation at room temperature indicates the amount of PPO enzyme activity in the sample. A sample with an unknown amount of enzyme activity may quickly be estimated relative to the activity expressed by a reference sample (e.g. the starting material) and dilutions hereof by visual inspection.

Procedure:

1.95 ml 0.1 M potassium phosphate pH 7.0
1 ml 0.1 M pyrocatechol in 0.1 M potassium phosphate pH 7.0
50 µl sample The solution is mixed well and incubated for 15 min at ambient temperature. After 15 min the color intensity is scored relative to a reference sample.

d) Determination of Glycoalkaloids

A HPLC method for determination of glycoalkaloids is applied according to Alt, V., Steinhof, R., Lotz, M., Ulber, R., Kasper, C., Scheper, T. *Optimization of glycoalkaloid analysis for us in industrial potato fruit juice downstreaming.*

*Eng. Life Sci.* 2005, 5, 562-567.

Alpha-solanine (Sigma Aldrich, USA, cat no.: S3757) is used as a reference.

e) Test for Alkaline Colored Phenolic Compounds

A qualitative test for the content of complex phenolic compounds based on the development of color in alkaline medium. 0.5 ml sample is mixed with 3 ml 1 M sodium hydroxide and the absorbance at 405 nm is determined within one minute from mixing (BK-UV1800 spectrophotometer, Biobase, China). The result is calculated relative to the protein concentration in the sample as OD405×7/(mg protein per ml sample).

f) Total True Protein Determination.

Standard amino acid quantification is performed according to EUROPEAN PHARMACOPOEIA 5.0 section 2.2.56. AMINO ACID ANALYSIS. Total protein concentration is also determined by the method of Kjeldahl using the conversion factor N×6.25. All samples are initially dialyzed against demineralised water in dialysis tubing cellulose membrane (Sigma-Aldrich, USA, cat. No.: D9652) to remove any free amino acids and low molecular weight peptides.

Ultrafiltration

Samples are ultrafiltrated using a system from Spectrum Labs, USA, fitted with KrosFlo TFF system KM0i using hollow fiber ultrafiltration membranes. A membrane cut-off value of 10 kDA and 100 kDa and membrane area of 75 cm2 is employed (Spectrum Labs, USA cat. no.: T02-E100-10-N).

Example 1. Preparation of a Soluble Starch Polymer Coupled with a Mixed Mode Ligand (4-Aminosalicylic Acid)

Soluble potato starch Sigma Aldrich, USA (cat. no.: S2004) is activated with AGE, bromine treated and coupled with 4-aminosalicylic acid using the following procedure: Activation with AGE: 25 g soluble starch is mixed thoroughly with 50 ml of water followed by addition of 25 ml AGE and 4 ml 30% sodium hydroxide. The solution is then incubated for 7.5 hours at 65-70° C. followed by addition of acetic acid to neutralize the hydroxide and stop the reaction. The resulting solution is dialyzed in a dialysis tube for two days against water to produce a solution free of remaining low molecular weight reactants while the allylated starch stay in the dialysis bag. The allylated starch polymer is then treated with bromine water (1% solution) until a red-brown color remains indicating that substantially all allyl groups have been brominated. The bromine treated polymer is coupled with 4-aminosalicylic acid by mixing 50 ml activated starch polymer with 5 g of amino salicylic acid and pH is adjusted to 12 with 5 M sodium hydroxide. The solution is mixed at ambient temperature for 24 hours where after the solution is dialyzed in a dialysis hose for two days against several shifts of water to produce a solution of ligand derivatized starch without any significant amount of free ligand in solution. Dry matter determination of the final starch-ligand solution indicated a final concentration of 9 mg per ml solution. The amount of 4-aminosalicylic acid ligand per mg starch is estimated by acid base titration to be in the range of 3-7 micromoles ligand per mg starch.

Example 2. Preparation of Adsorbent Beads Coupled with a Mixed Mode Ligand (4-Aminosalicylic Acid)

6% spherical agarose beads (50-150 µm diameter) from ABT, Spain (cat. no.: A-1060M-X) are crosslinked with 1,4-butanediol diglycidyl ether (BDDGE) from Sigma Aldrich, USA (cat. no.: 124192, 60%) by mixing 450 ml agarose beads with 60 ml BDDGE and 27 ml 50 wt % sodium hydroxide for 18 hours at ambient temperature followed by washing with 10 L water on a sintered glass funnel.

The cross-linked beads are then activated with allyl glycidyl ether (AGE) Sigma Aldrich, USA (cat. no.: 32608) by mixing 200 ml cross-linked beads with 80 ml AGE and 20 ml 30 wt % sodium hydroxide on a temperature controlled water bath (60-65° C.) for three hours. The activated beads are then washed thoroughly with 5 L water on a sintered glass filter. The cross linked and activated beads are the suspended in 200 ml water and added bromine water (1%, solution) while mixing until a red-brown color remains in the mixture indicating that a surplus of bromine has been added. After bromine treatment, the beads are washed thoroughly with water (2 L) on a sintered glass filter.

The mixed mode ligand 4-aminosalicylic acid, Sigma Aldrich, USA (cat. no.: A79604) is coupled to the bromine treated AGE-beads by mixing 20 ml bromine treated beads with 2 g of 4-aminosalicylic acid and 10 ml water followed by adjustment of pH to pH 12 with 5 M sodium hydroxide. The suspension is mixed 24 hours at ambient temperature. The beads are then washed thoroughly with water, 0.1 M sodium hydroxide and 0.1 M sodium chloride.

The ligand concentration on the resulting beads is determined to be in the range of 50-80 micromoles per milliliter sedimented wet beads by acid-base titration.

Example 3. Precipitating the PI Fraction from Potato Juice with a Ligand Derivatised Starch Polymer 4 ml of potato juice produced according to materials and methods (true protein concentration: 8 g/L) (test solution 1) is mixed with 1 ml of 4-aminosalicylic acid starch polymer (prepared according to example 1). The pH in the solution is adjusted to pH 5.5 with 1 M hydrochloric acid under mixing at ambient temperature for 10 minutes. The precipitated solution is then centrifuged for 5 min at 1340 g and the supernatant is collected (test solution 2).

The test solutions are analyzed by SDS-PAGE as illustrated in FIG. 1. The PPO activity of the test solutions is further determined according to materials and methods and shown in table 1.

The SDS-PAGE illustrates that the major part of PI is precipitated with the starch polymer modified with 4-aminosalicylic acid resulting in a PA enriched juice, see lane 2 which has a rather faint PI band compared to non-treated juice of lane 1.

Table 1 showing the PPO activity in test solution 1 and 2.

| Samples | PPO activity |
| --- | --- |
| Non-treated potato juice (test solution 1) | ++++ (dark orange) |
| Test solution 2 | + (pale yellow) |

The results indicate that the PPO is eliminated efficiently from the PA enriched juice.

Figure 2:
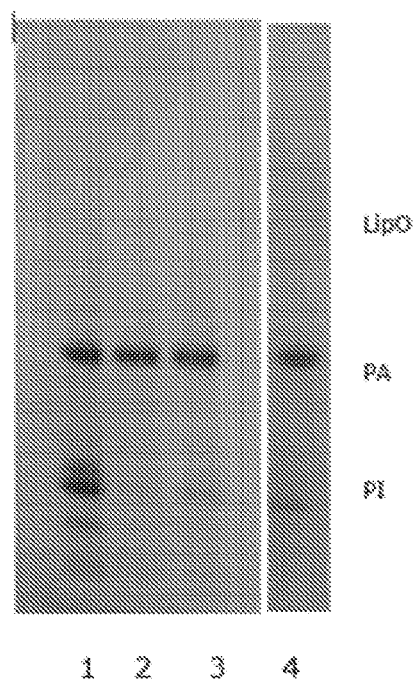

Example 4. Isolating PI Fraction from Potato Juice with a Mixed Mode Adsorbent 5 respectively 10 and 15 ml of potato juice samples (test solution 1, produced according to materials and methods, true protein concentration: 8 g/L) is adjusted to pH 5.5 with 1 M hydrochloric acid and mixed with 1 ml of 4-aminosalicylic acid adsorbent (produced according to example 2). The juice samples are incubated with the adsorbent on a roller mixer for 30 min at ambient temperature. After incubation, the samples are set at rest for 30 min to settle the adsorbent. The resulting supernatants (test solution 2, 3 and 4 respectively) are collected and tested by SDS-PAGE according to materials and methods as illustrated in FIG. 2. Test solutions 1-4 is further tested for PPO activity according to materials and methods as illustrated in table 2.

Results:

The SDS-PAGE of FIG. 2, illustrates that the mixed mode adsorbent binds substantially all the PI present in the juice at all three juice:adsorbent ratios. There is a rather small amount of PI left in the supernatant with 10 and 15 ml juice, see lane 3 and 4. The PA is not bound by the adsorbent in any significant amount resulting in a juice that is highly enriched with respect to PA.

Table 2 showing the PPO activity in test solution 1-4.

| Samples | PPO activity |
|---|---|
| Non-treated potato juice (test solution 1) | ++++ (dark orange) |
| Test solution 2 | + (pale yellow) |
| Test solution 3 | + (pale yellow) |
| Test solution 4 | + (pale yellow) |

The results indicate that the PPO is eliminated efficiently from all the PA enriched samples.

Example 5. Isolating PI Fraction from Potato Juice with a Mixed Mode Adsorbent Followed by Precipitation of PA with Sodium Alginate 10 ml juice prepared according to materials and methods (test solution 1, true protein concentration: 12 g/L) is depleted for PI according to example 4 by incubation with 1 ml adsorbent (test solution 2).

7 ml of the PI depleted sample is then mixed with 1 ml of ligand solution A and pH is adjusted to 3.5 with 1 M hydrochloric acid under thorough mixing at ambient temperature. After 10 minutes mixing the precipitated solution is centrifuged for 10 min at 1340 g. The supernatant is removed (test solution 3) and the precipitate is washed by resuspension in water and repeated centrifugation. The precipitate is hereafter dissolved by addition of 7 ml 0.1 M potassium phosphate pH 7.0 (test solution 4).

Figure 3:
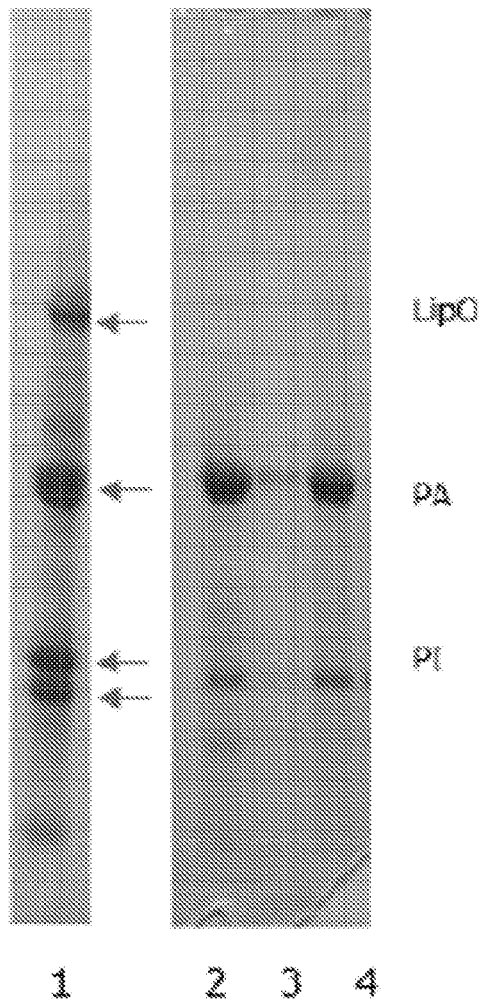

The test solutions are tested by SDS-PAGE as illustrated in FIG. 3. Test solutions 1 and 4 are tested for glycoalkaloids and alkaline colored phenols.

Results:

The SDS-PAGE of FIG. 3 illustrates that the PA enriched juice only contains a minor fraction of the PI, see lane 2 (rather faint PI band compared to non-treated juice). LipO is also eliminated from the PA enriched juice, see lane 2 (LipO band has disappeared). Further it can be observed that the precipitation of PA with sodium alginate is rather effective, see lane 3 (very faint bands meaning that most of the protein is precipitated and thereby removed from the supernatant). The resulting dissolved product, see lane 4, is a highly enriched PA fraction with a low content of PI. Determination of the glycoalkaloid content of test solution 4 relative to test solution 1 shows that also a significant reduction of this toxic substance is taking place. Visual inspection of the color intensity of the dissolved PA (test solution 4) compared to the starting material (test solution 1) indicates that almost all colored substances (phenolic compounds) remain in the juice and very little is found in the re-dissolved PA solution (test solution 4). Likewise, the presence of alkaline colored phenols is much lower in test solution 4 compared to test solution 1.

Example 6. Isolating Protein from Potato Juice Using Silicate Polymers 60 ml of potato juice produced according to materials and methods (test solution 1, protein concentration 13 g/L) is divided into 5 samples (A through E respectively) of 12 ml juice and each mixed with 0.25 ml of a concentrated sodium silicate solution, reagent grade water glass (Sigma Aldrich, USA cat. No.: 338443, Na2O=10.6%, SiO2=26.5%) density 1.39 g/ml at 25° C. Addition of the waterglass is performed in aliquots of 0.05 ml and pH is immediately adjusted to pH 7 with 1 M hydrochloric acid in between each addition. When the full amount of waterglass has been added the samples are adjusted to a final pH value of 6.0. Following incubation for 5 minutes with stirring at ambient temperature the samples are centrifuged for 5 min at 1430 G and the supernatant (test solution 2) is separated from the precipitate.

The precipitate remaining in each centrifuge tube is resuspended in 6 ml water and then centrifuged again. This procedure is repeated twice. Following the last centrifugation, the water washing supernatants are discarded while the precipitates are transferred into small beakers under addition of 12 ml water each. The beakers are labelled A-E and adjusted to varying pH values with 1 M sodium hydroxide under stirring as follows: A) pH 7.0, B) pH 8.0, C) pH 9.0, D) pH 10.0 and E) pH 11.0. The samples are then incubated with stirring for 10 min at ambient temperature where after they are centrifuged for 5 min at 1430 g. By visual inspection sample A) through D) contained the same amount of precipitate as the first centrifugation at pH 6.0. There was practically no remaining precipitate in sample E) pH 11.0. The supernatants A), B), C), D) and E) are separated from the precipitates to form test solution 3-7 respectively. The precipitate in each test tube is added 6 ml 0.1 M sodium hydroxide to dissolve the precipitate resulting in test solution 8-11. SDS-PAGE is performed on test solutions 1 to 11 as illustrated in FIG. 4.

Figure 4:
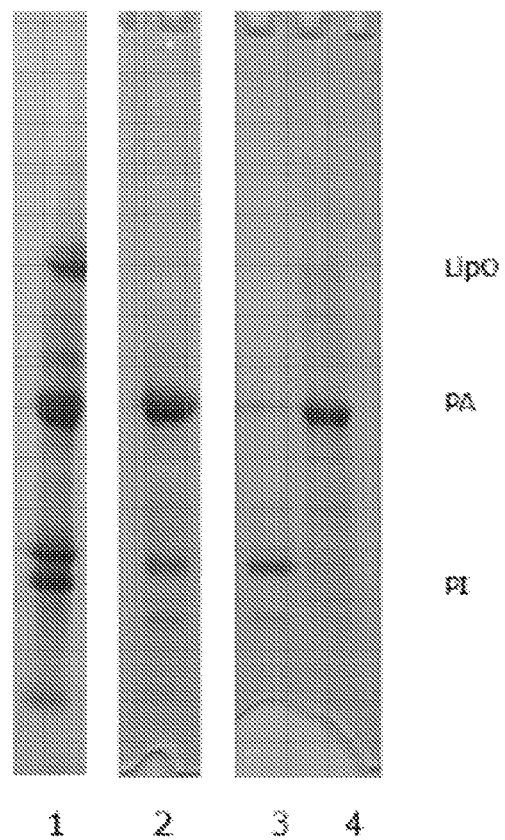
FIG. 4:
Illustrates SDS PAGE analysis of test solutions of example 22.
Figure 5:
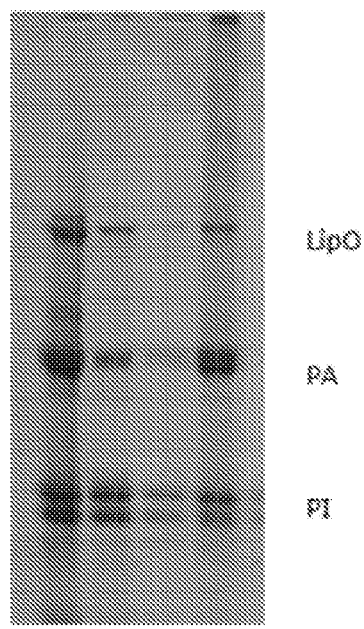
FIGS. 5 and 6:
Illustrates SDS PAGE analysis of test solutions of examples 7.
Figure 6:
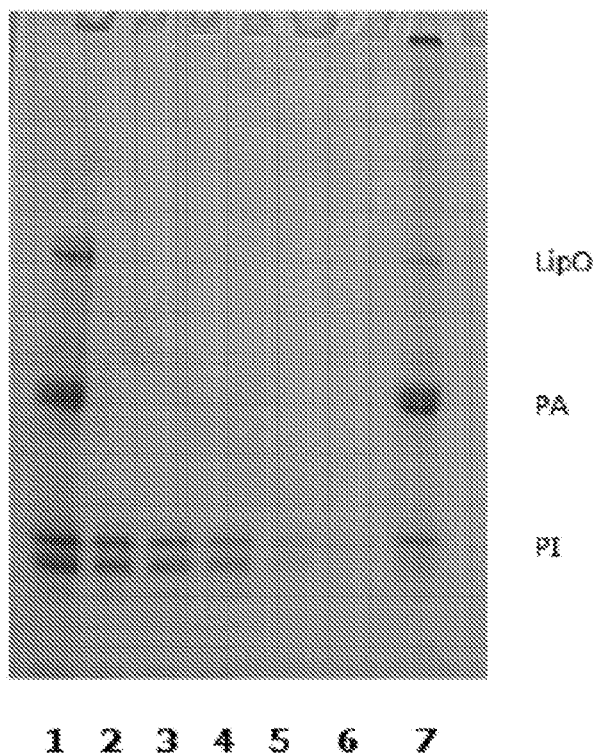
Figure 7:
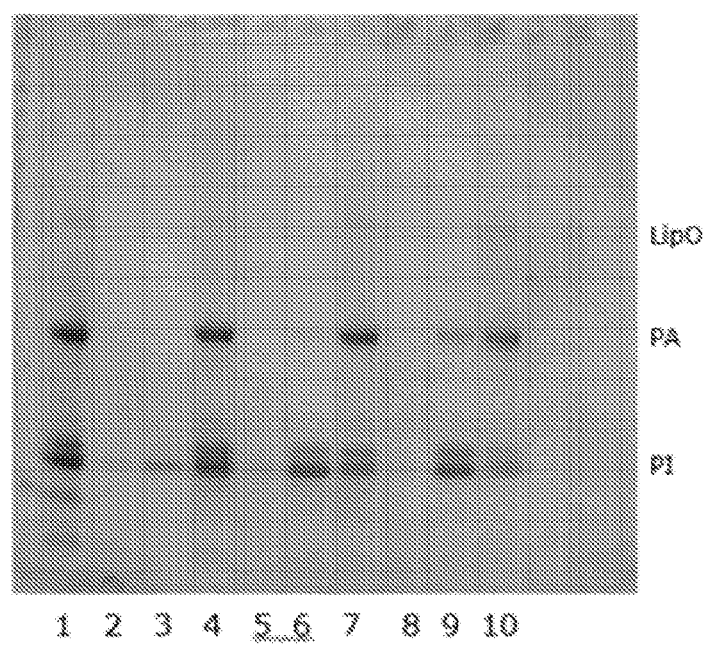
FIGS. 7 to 22:
Illustrates SDS PAGE analysis of test solutions of examples 8 to 32 respectively.

The SDS PAGE analysis of FIG. 4, illustrates that the sodium metasilicate solution is capable of precipitating almost all the protein present in the potato fruit juice—see lane 2 which shows that only a minor fraction of the PI is left in the supernatant. Further, it is seen that after washing of the precipitate with water and then incubating at pH 7 results in a highly selective release of PA proteins (see lane 3) with a rather small amount of PI being released from the precipitate. Increasing the pH of the incubation to pH 9.0 (see lane 7 compared to lane 8) results in an almost complete elution of PA and only a fraction of PI resulting in a highly enriched PA supernatant and a PI enriched precipitate (see lane 8). At pH 10.0 practically all the precipitated proteins are released in one pool while it is important to note that also at this pH the silicate is still precipitated. Lane 11 illustrates that practically all the bound proteins are present in the dissolved precipitate. There is practically no precipitate left at pH 11 and the proteins are therefore in this sample still in the same fraction as the silicate.

Example 7. Isolating a Protein Fraction Enriched in PA from Potato Juice 474 ml potato juice produced according to materials and methods (test solution 1, true protein concentration: 11 g/L) is mixed with 26 mL of sodium alginate solution (ligand solution A) and pH is adjusted to 3.8 using 1 M HCl under thorough stirring. Protein and sodium alginate are allowed to form complexes during mixing for 10 minutes at ambient temperature.

The solution is then centrifuged for 5 min at 1430 G and the supernatant (test solution 2) separated from the precipitate. The precipitate is washed briefly by resuspension in water and repeated centrifugation (test solution 3).

The precipitate is then again suspended in water and pH is adjusted to pH 7.5 with 1 M NaOH to a final volume of 500 mL (test solution 4). During this step the precipitate is dissolved to produce a slightly hazy solution.

The solubilized precipitate is ultrafiltered using a 100 kDa hollow fiber membrane. When 310 ml permeate (test solution 5) is collected the retentate is diafiltered with four portions of 100 mL 1 mM NaCl solution—the next portion only added after permeation of the foregoing portion. The permeate of each portion of diafiltration is denoted test solutions 6, 7, 8 and 9, while the retentate resulting from the diafiltration is denoted test solution 10.

SDS-PAGE is performed on the fractions.

SDS-PAGE is performed on test solutions 1 to 4 as depicted in FIG. 5 wherein lanes starting from the left are test solutions 1, 2, 3 and 4 respectively.

Results:

From the SDS-PAGE of FIG. 5 it is observed that the majority of the PA is precipitated with the polymeric ligand (see lane 2, the PA band in test solution 2 is faint), the majority of the PI's are still in test solution 2 (see lane 2, the bands representing PI are very strong in test solution 2). Test solution 4 contains a high concentration of PA and a low concentration of PI compared to test solution 1 showing that PA is isolated in test solution 4 (see lane 4)

SDS-PAGE is performed on test solutions 4 and 5 to 10 as depicted in FIG. 6, wherein lanes starting from the left are test solutions 4 and 5 to 10 respectively.

From the SDS-PAGE gel of FIG. 6, it is observed that ultra-filtering test solution 4 enriches PA in the retentate even further. It is contemplated that during the ultrafiltration and diafiltration of test solution 4, PI passes the membrane and the PA and LipO is left in the retentate (no PA or LipO is detected in test solutions 5 to 9). Test solution 10 on the other hand contains a high concentration of PA and a low concentration of PI.

This experiment shows that PA and a fraction of the PI is precipitated with sodium alginate at pH 3.8. The precipitate can be collected and redissolved and the PA can be further enriched by ultrafiltration separating the majority of PI in the permeate from the ultrafiltration filter, while the retentate is a highly enriched PA product mixed with sodium alginate.

Determination of the glycoalkaloid content, color and alkaline colored phenols of the final PA enriched product (test solution 10) shows that only very little of these contaminants are present.

Example 8. Isolating a PA and a PI Fraction from a Precipitate by Selective Elution 21 ml of potato juice produced according to materials and methods (test solution 1, true protein concentration 7 g/L) is divided into 3 samples (A, B and C respectively) of 7 ml juice and each is mixed with 1 ml of 1.5% sodium alginate solution (ligand solution A) and pH is adjusted to 3.5 with 1 M hydrochloric acid under thorough stirring at ambient temperature. The resulting solutions are incubated under stirring for 10 min.

The solutions are centrifuged in 3 separate tubes for 5 min at 1430 g and the supernatants removed (test solutions 2-4 respectively). The precipitates are briefly washed by resuspension in 5 ml water each and repeated centrifugation.

The three identical precipitates labelled A, B and C and then washed by resuspension with 7 ml of each of the following solutions:

A: 0.2 M NaCl, 5 mM sodium acetate pH 3.5,

B: 0.4 M NaCl, 5 mM sodium acetate pH 3.5,

C: 0.6 M NaCl, 5 mM sodium acetate pH 3.5.

After mixing the precipitates thoroughly with the salt containing buffers at ambient temperature the samples are centrifuged 5 min at 1430 g. The supernatants, A, B and C are collected for analysis (test solution 5-7 respectively).

The 3 precipitates are then each added 7 ml 0.1 M potassium phosphate pH 7.5 under mixing which dissolves the precipitates to produce slightly hazy solutions (test solutions 8-10 respectively). SDS-PAGE is performed on test solutions 1-10 as illustrated in FIG. 7.

Results:

The SDS-PAGE of FIG. 7 illustrates that substantially all the protein precipitates at pH 3.5 together with the alginate, only very faint protein bands are detected in the supernatant, see lane 2, 5 and 8. It is also concluded that washing the precipitate with salt solution pH 3.5 releases mainly PI from the precipitate the higher salt concentration the more PI is released, see lane 3, 6 and 9. When washing with 0.6 M sodium chloride pH 3.5 the major part of the PI is released and a minor fraction of PA, see lane 9. After washing the precipitate with 0.6 M NaCl pH 3.5 the resulting solubilized precipitate mainly contains PA and a slight amount of PI, see lane 10.

Example 9. Isolating a PA and a PI Fraction from a Precipitate by Selective Elution 7 ml of potato juice produced according to materials and methods (true protein concentration: 7 g/L, test solution 1) is mixed with 1 ml of 1.5% sodium alginate solution (ligand solution A) and pH is adjusted to 3.5 with 1 M hydrochloric acid under thorough stirring at ambient temperature. The resulting solution is incubated under stirring for 10 min.

The solution is centrifuged for 5 min at 1430 g and the supernatant (test solution 2). The precipitate is briefly washed by resuspension in 5 ml water and repeated centrifugation.

The precipitate is then washed by resuspension with 7 ml 0.7 M NaCl, 5 mM sodium acetate pH 3.0. After mixing the precipitate thoroughly with the salt containing acetate buffer for 5 min at ambient temperature the sample is centrifuged 5 min at 1430 g. The supernatant is collected for analysis (test solution 3). The precipitate is mixed with 7 ml 0.1 M potassium phosphate pH 7.5 which dissolves the precipitate to produce a slightly hazy solution (test solution 4). SDS-PAGE is performed on the test solutions as illustrated in FIG. 8

Figure 8:
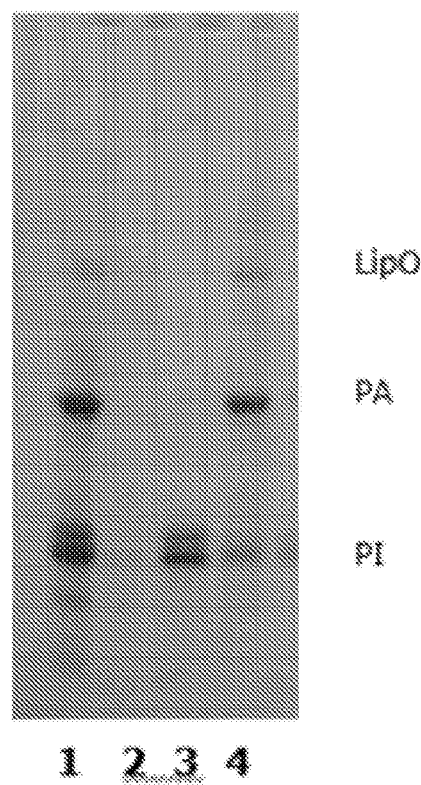

Results:

The SDS-PAGE of FIG. 8 illustrates that substantially all the protein precipitates at pH 3.5 together with the alginate, only very faint protein bands are detected in the supernatant, see lane 2. It is also illustrated that washing the precipitate with 0.7 M NaCl plus acetate pH 3.0 releases the major part of PI from the precipitate, see lane 3. No significant amount of PA is released (eluted) during this wash. After washing the precipitate with 0.7 M NaCl pH 3.0 the resulting solubilized precipitate mainly contains PA and a small amount of PI, see lane 4. Washing the precipitate with salt solutions at higher pH-values than 3.5 elutes both PA and PI to a significant degree.

Determination of the true protein concentration of test solution 3 and 4 relative to the starting material (test solution 1) indicates a total yield corresponding to more than 90%, while practically no true protein remains in the supernatant (test solution 2).

Determination of the glycoalkaloid content, color and alkaline colored phenols of the PI enriched product (test solution 3) and the PA enriched product (test solution 4) shows that only very little of these contaminants are present, while most of these contaminants remain in the supernatant (test solution) and water washing fraction.

Example 10. Isolating a PA and PI Fraction from Potato Juice with Sodium Alginate 8 ml potato juice produced according to materials and methods (true protein concentration 8 g/L, test solution 1) is mixed with 2 ml of 1.5% sodium alginate solution (ligand solution A) and pH is adjusted in steps to pH 4.5, pH 4.0, pH 3.5 and pH 3.0 with 1 M hydrochloric acid. At each pH-value a 250 μl sample is taken out and centrifuged at 2680 g for 5 min. The supernatants are collected to produce test solutions 2, 3, 4 and 5 respectively.

Figure 9:
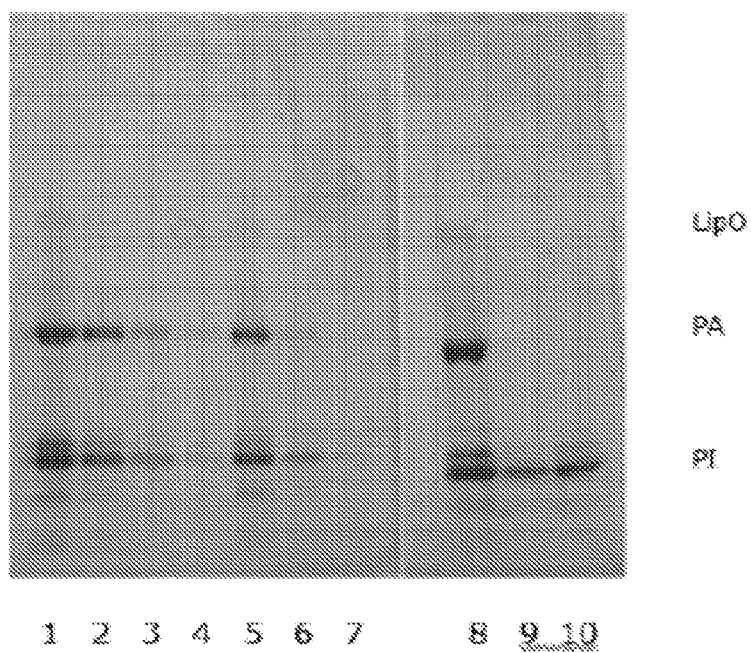

In a further experiment 13 ml of the same potato juice is mixed with 2 ml of ligand solution A and pH is again adjusted to respectively pH 4.5, pH 4.0, pH 3.5 and pH 3.0 with 1 M hydrochloric acid. At each pH-value a 250 μl sample is taken out. The samples are centrifuged at 2680 g for 5 min. The supernatants are collected to produce test solutions 6, 7, 8 and 9 10 respectively. The test solutions are analyzed with SDS-PAGE as illustrated in FIG. 9.
Results:

The SDS-PAGE of FIG. 9 illustrates that for both experiments practically all the PA is precipitated at pH 4.0, see lane 3 and 6 which has only faint PA bands for both ratios. In addition is it seen that for both experiments practically all the proteins are precipitated at pH 3.5, see lane 4 and 7. At lower pH (pH 3.0) a fraction of PI for both ratios is still in solution, see lane 9 and 10 which indicates that the optimal conditions for a high yield are above pH 3.0.

Example 11. Isolating a PA Enriched Fraction from Potato Juice with Sodium Alginate Second precipitation of non-precipitated proteins with additional alginate 40 ml of potato juice produced according to materials and methods (test solution 1, true protein concentration 11 g/L) is mixed with 1 ml of 1.5% sodium alginate solution (ligand solution A) and pH is adjusted to pH 3.8 with 1 M hydrochloric acid. Following mixing for 5 minutes at ambient temperature the sample is centrifuged at 1430 g for 10 min. The supernatant is collected (test solution 2). The precipitate is washed by resuspension in water and repeated centrifugation. The precipitate is then suspended 35 ml water and pH is slowly adjusted to pH 7.5 with 1 M NaOH during mixing at ambient temperature for 30 min. Hereafter the volume of the dissolved precipitated is adjusted to 40 ml by addition of water to produce a slightly hazy solution (test solution 3).

Figure 10:
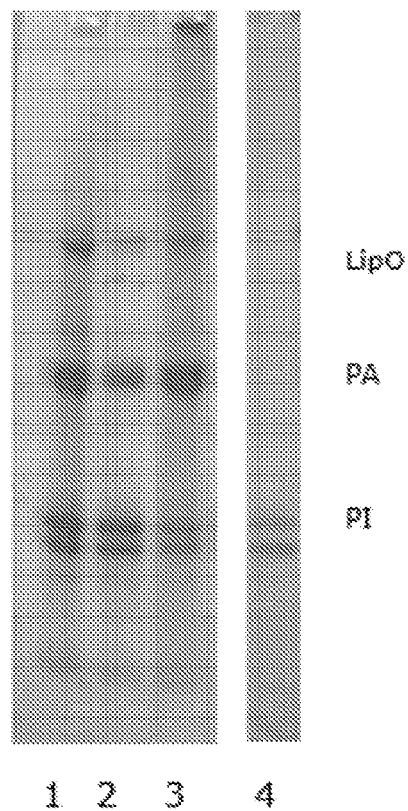

The supernatant (40 ml, test solution 2) is adjusted to pH 4.5 and mixed with 4.4 ml 1.5% sodium alginate solution (produced according to materials and methods, ligand solution A) and pH is adjusted to 3.8 with 1 M hydrochloric acid during mixing at ambient temperature for 5 min. The sample is then centrifuged at 1430 g for 10 min. The supernatant is collected (test solution 4). The test solutions are analyzed with SDS-PAGE as illustrated in FIG. 10.
Results:

The SDS-PAGE of FIG. 10 illustrates that the supernatant from the first precipitation (see lane 2) contains only a small fraction of the PA compared to the starting material). The major part of PI is still in solution (see lane 2, strong PI bands in supernatant).

The dissolved precipitate contains a large amount of PA and only a minor fraction of PI resulting in a highly enriched PA product, see lane 3.

The second precipitation precipitates practically all the remaining protein, rather weak PI bands are left no detection of PA (see lane 4), resulting in an isolated product mainly containing PI and a minor fraction of the PA (not shown).

Example 12. Isolating Protein from Potato Juice with Polyacrylic Acid Polymer (MW 450,000)

Figure 11:
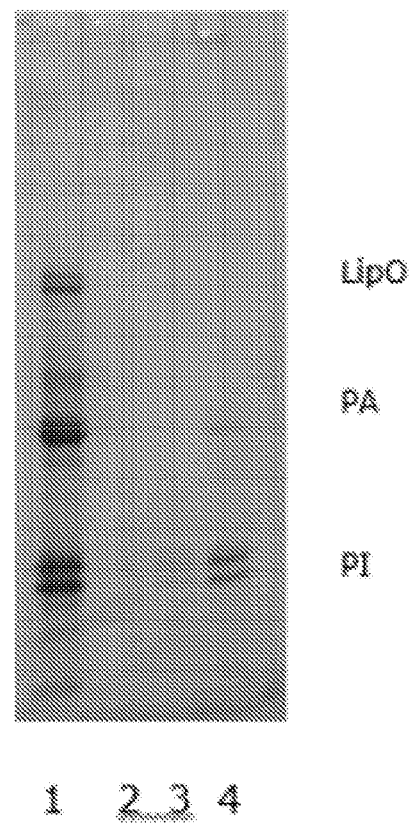

10 ml potato juice produced according to materials and methods (test solution 1, true protein concentration 9 g/L) is mixed with 1 ml 1.5% polyacrylic acid solution, molecular weight 450,000 (ligand solution E) and pH is adjusted in steps to pH 4.5, pH 4.0 and pH 3.5 respectively with 1 M hydrochloric acid. At each pH-value a 250 μl sample is taken out and centrifuged at 2680 g for 5 min. The supernatants (test solutions 2, 3 and 4 respectively) are collected and analyzed with SDS-PAGE as illustrated in FIG. 11.
Results:

The SDS PAGE of FIG. 11 illustrates that all the proteins are precipitated quantitatively at pH 4.5, no protein bands are detected on the gel, see lane 2. The major part of all the proteins are also precipitated at pH 4.0, only very faint PI bands are detected, see lane 3. At pH 3.5 a minor fraction of PI is still in solution while a very small amount of PA is detected, see lane 4. The results thus indicate that the optimal binding conditions are above pH 3.5

Example 13. Isolating Protein from Potato Juice with Polyacrylic Acid Polymer (MW 450,000 and MW 15,000)

Two samples of 20 ml from a potato juice produced according to materials and methods (test solution 1, true protein concentration: 8 g/L) is mixed with 1 ml 1.5% polyacrylic acid solution, molecular weight 450,000 respectively 1.5% polyacrylic acid solution (ligand solution E), molecular weight 15,000 (ligand solution F) and pH is adjusted under mixing to respectively pH 5.0, pH 4.5 and pH 4.0 with 1 M hydrochloric acid. At each pH-value a 250 μl sample is taken out. The samples are centrifuged at 2680 g for 5 min. The supernatants are collected to produce test solutions 2-7 respectively and analyzed by SDS-PAGE as illustrated in FIG. 12.

Figure 12:
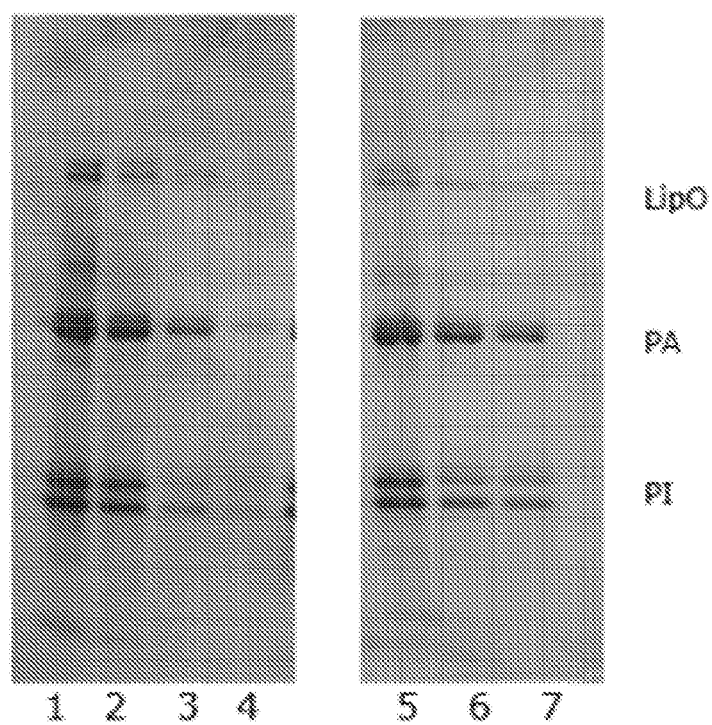

Results:

The SDS-PAGE of FIG. 12 illustrates that the acrylic acid polymer with high molecular weight (450,000 D) precipitates practically all the PA and PI at pH 4.0, see lane 4 (rather weak bands are detected for both PI, PA and LipO). The polyacrylic acid with a molecular weight of 15,000 D also precipitates PA and PI but not as effective as the high molecular weight polymer. The lower pH the more protein is precipitated but still at pH 4.0 a significant amount of both PA and PI remain in solution, see lane 7.

Example 14. Isolating Protein from Potato Juice with Carrageenan (Kappa, Iota and Lambda)

Figure 13:
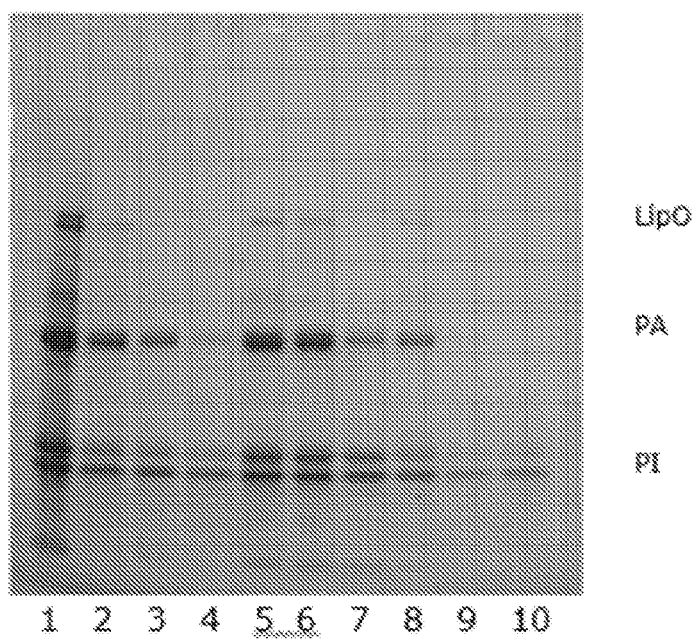

Three 10 ml samples of a potato juice produced according to materials and methods (test solution 1, true protein concentration 10 g/L) is mixed with 1 ml of 1.5% kappa carrageenan, iota carrageenan and lambda carrageenan respectively (ligand solution B, C and D respectively) and pH is adjusted with mixing at ambient temperature for 5 min to respectively 4.5, 4.0 and 3.5 with 1 M hydrochloric acid. At each pH-value a 250 µl sample is withdrawn. The samples are centrifuged at 2680 g for 5 min. The supernatants (test solutions 2-10 respectively) are collected and analyzed by SDS-PAGE as illustrated in FIG. 13.
Results:

The SDS-PAGE of FIG. 13 illustrates that for all three types of carrageenan the lower pH the more protein is precipitated of both PA and PI. Lambda carrageenan is the most effective polymer to precipitate both PA and PI, already at pH 4.5 most of both PA and PI is precipitated, see lane 8. For Lambda carrageenan at pH 4.0 and 3.5 all the PA is precipitated, see lane 9 and 10. At pH 4.0 the major part of PI is also precipitated, see lane 9 (very weak PI bands left). There is slightly more PI in the supernatant at pH 3.5, see lane 10.

For kappa carrageenan, practically all PA is precipitated at pH 3.5, see lane 4 but there is still a fraction of PI in the supernatant. For iota carrageenan, most of the protein both PA and PI is still in the supernatant at pH 4.5 and 4.0, see lane 5 and 6. At pH 3.5 a large fraction of the PA is precipitated but a significant fraction of the PI is still in solution.

Example 15. Isolating a PA Fraction from Potato Juice with pH-Adjustment Followed by Precipitation of PI Enriched Product with Lambda Carrageenan 50 ml of potato juice produced according to materials and methods (test solution 1, true protein concentration 11 g/L) is adjusted to pH 3.5 with 1 M hydrochloric acid at ambient temperature. The solution is then centrifuged for 10 min at 1340 g. The supernatant is collected and pH-adjusted to 4.5 (test solution 2). The precipitate is washed by resuspension in 10 ml water and repeated centrifugation. The washing water is collected after centrifugation (test solution 3). The washed precipitate is hereafter suspended in 25 ml 0.1 M NaCl. The pH is slowly adjusted to 7.5 with 1 M NaOH under mixing at ambient temperature to dissolve the precipitate and create a hazy solution (test solution 4). The supernatant (test solution 2) is added 2.5 ml 1.5% lambda carrageenan (ligand solution D) produced according to materials and methods and pH is adjusted to pH 4.0 with 1 M hydrochloric acid. The sample is centrifuged at 1340 g for 10 min and the supernatant is collected (test solution 5). The precipitate is washed by resuspension in water and repeated centrifugation. Hereafter the precipitate is added 25 ml water and pH is slowly adjusted to pH 8.5 under mixing at ambient temperature to solubilize the precipitate and create a slightly hazy solution (test solution 6).

Figure 14:
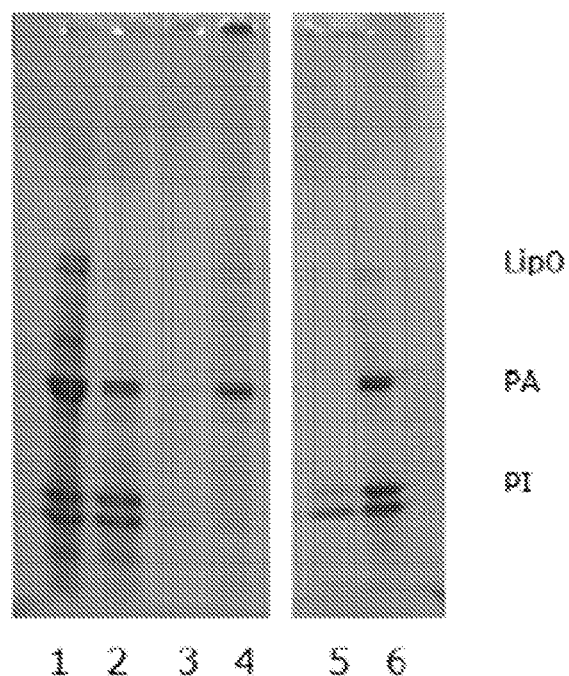

The test solutions are analyzed by SDS-PAGE as illustrated in FIG. 14 and dry matter content is determined according to materials and methods for test solution 4 and 6.
Results:

The SDS-PAGE of FIG. 14 illustrates that the pH-adjustment to 3.5 only precipitates PA resulting in a very pure PA product, see lane 4 (practically no PI in this fraction). The supernatant contains all the PI and a small amount of PA. The lambda carrageenan precipitates practically all the protein left in the supernatant, see lane 5 (only very faint bands from PI is left in this fraction). The dissolved precipitate contains practically all the PI and a small amount of PA.

Results from dry matter determination: The PA product (test solution 4) contains 187.5 mg dry matter, this corresponds to 3.75 mg dry matter per ml juice applied in the test. The enriched PI product (test solution 6) contains 339.9 mg dry matter, which corresponds to is 6.8 mg dry matter per ml juice applied in the test. The dry matter values are corrected for the content of sodium chloride respectively lambda carrageenan. Therefore, it can be concluded that in a total 10.6 g dry matter is isolated per liter of potato juice applied in the test. Determination of the true protein show that the dry matter comprises more than 91% protein when corrected for the content of sodium chloride and carrageenan corresponding to a yield of 9.65 g true protein. Thus, compared to the starting material (test solution 1) the yield is 9.65/11×100%=87.7%

Figure 15:
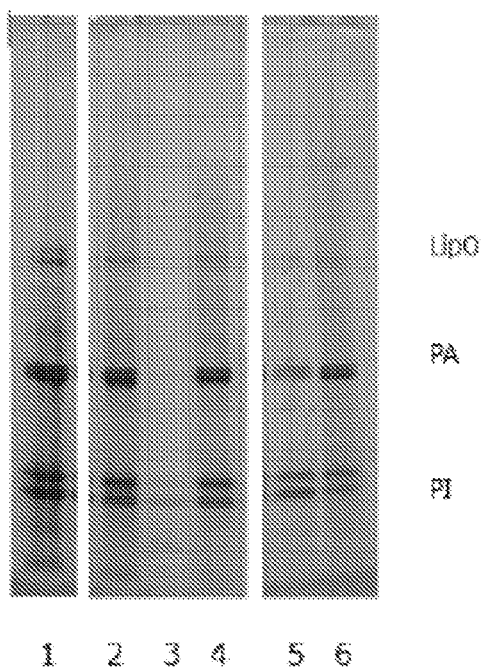

Example 16. Precipitation of Protein from Potato Juice with Lambda Carrageenan, Washing the Precipitate with a Salt Buffer to Selectively Elute PI and Obtain a PA Enriched Dissolved Product Three samples of each 10 ml from a potato juice produced according to materials and methods (true protein concentration 8 g/L, test solution 1) is mixed with each 0.71 ml of 1.5% lambda carrageenan (ligand solution D) and pH is adjusted to pH 4.0 with 1 M hydrochloric acid with mixing at ambient temperature for 5 min. The samples are centrifuged at 1340 g for 10 min. The precipitates are washed by resuspension in water and repeated centrifugation. The first precipitate is then added 10 ml of water and pH is increased to pH 8.0 by slow addition of 1 M sodium hydroxide resulting in a first re-solubilized sample (test solution 2). To the second precipitate is added 10 ml 0.3 M sodium chloride, 5 mM sodium acetate pH 4.5 and to the third precipitate is added 10 ml 0.6 M sodium chloride, 5 mM sodium acetate pH 4.5 with mixing. The two still precipitated samples are mixed well for 5 min at ambient temperature and centrifuged at 1340 g for 10 min. The supernatants are collected as test solution 3 and 4 respectively. 10 ml of water is added to each of the two corresponding precipitates and pH is increased to pH 8.0 by slow addition of 1 M sodium hydroxide resulting in two re-solubilized samples (test solution 5 and 6 respectively). The test solutions are analyzed by SDS-PAGE as illustrated in FIG. 15.
Results:

The SDS-PAGE of FIG. 15 illustrates that without washing with salt the solubilized product contains both PA and PI, see lane 2. When washing with 0.3 M sodium chloride a small amount of PI is released, see lane 3 so that the resulting solubilized product still contains a large amount of PI, see lane 4. When increasing the salt concentration to 0.6

M sodium chloride a large amount of especially the PI is released, see lane 5 resulting in a PA enriched fraction, see lane 6.

Example 17 Isolating protein from potato juice using silicate polymers 50 ml of potato juice produced according to materials and methods (test solution 1, true protein concentration 13 g/L) is divided into 5 samples (A through E respectively) of 10 ml juice and each mixed with 0.25 ml of a concentrated solution of sodium metasilicate, technical grade waterglass (Matas, Denmark) 36-38 degrees Baumé, dry matter concentration 52 wt %. Addition of the waterglass is performed in aliquots of 0.05 ml and pH is immediately adjusted to pH 7 with 1 M hydrochloric acid in between each addition. When the full amount of waterglass has been added the samples are adjusted to the following final pH values: A) 6.1, B) 5.5, C) 4.9, D) 4.5 and E) 3.9. Following incubation for 5 minutes with stirring at ambient temperature the samples are centrifuged for 5 min at 1430 G and the supernatant (test solutions 2-6) separated from the precipitate. SDS-PAGE is performed on test solutions 1 to 6 as illustrated in FIG. 16.

Figure 16:
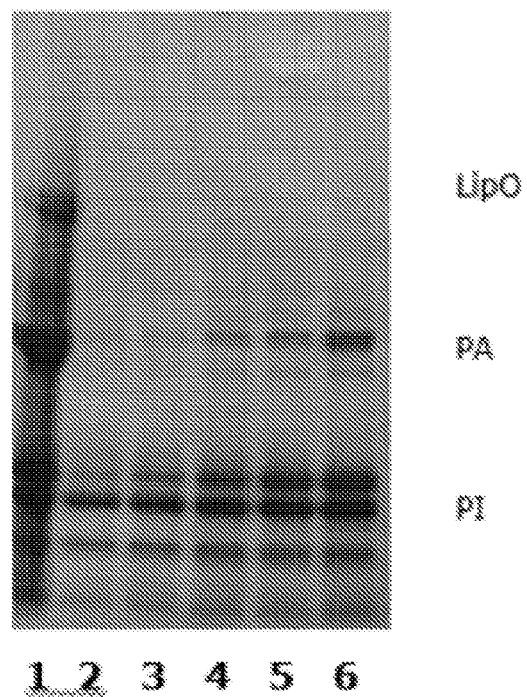

Results:

From the SDS-PAGE of FIG. 16 it is observed that almost all the protein in the juice is precipitated with the water glass at pH 6.1 (lane 2, only a small fraction of the PI is remaining in the supernatant). It is further indicated that with decreasing pH the selectivity of the precipitation becomes pronounced such that at pH 3.9 and 4.5 (lane 5 and 6) most of the PI is in solution while almost all the patatin and LipO is precipitated. Remarkably it is further observed by visual inspection that all the test solutions 2 through 6 are practically colorless indicating that the brownish colored polyphenols present in the starting juice (test solution 1) are eliminated from the protein in solution.

Example 18 Isolating protein from potato juice using silicate polymers 50 ml of potato juice produced according to materials and methods (test solution 1, true protein concentration 13 g/L) is mixed with 0.5 ml of a concentrated solution of sodium metasilicate, technical grade waterglass (Matas, Denmark) 36-38 degrees Baumé, dry matter concentration 52 wt %. Addition of the waterglass is performed in aliquots of 0.25 ml and pH is immediately adjusted to pH 7 with 1 M hydrochloric acid in between each addition. When the full amount of waterglass has been added the sample is adjusted to a final pH of 6.1. Following incubation for 5 minutes with stirring at ambient temperature the sample is centrifuged for 5 min at 1430 G and the supernatant (test solutions 2) is separated from the precipitate. SDS-PAGE is performed on test solutions 1 and 2 as illustrated in FIG. 17.

Figure 17:
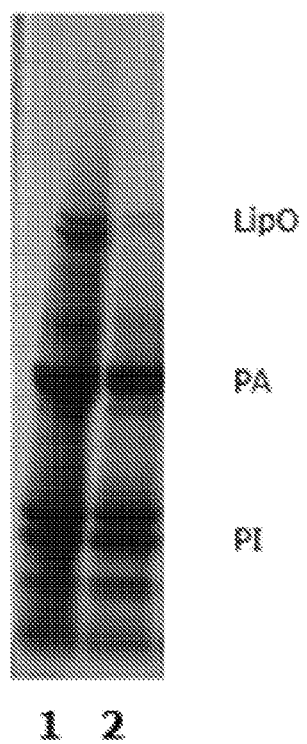

Results:

The result of the SDS-PAGE of FIG. 17 illustrates that under these conditions the precipitation is highly selective. LipO is practically eliminated from the supernatant while the PA and PI mainly stay in solution. Visual inspection of the supernatant show that also the colored polyphenols have been removed.

Figure 18:
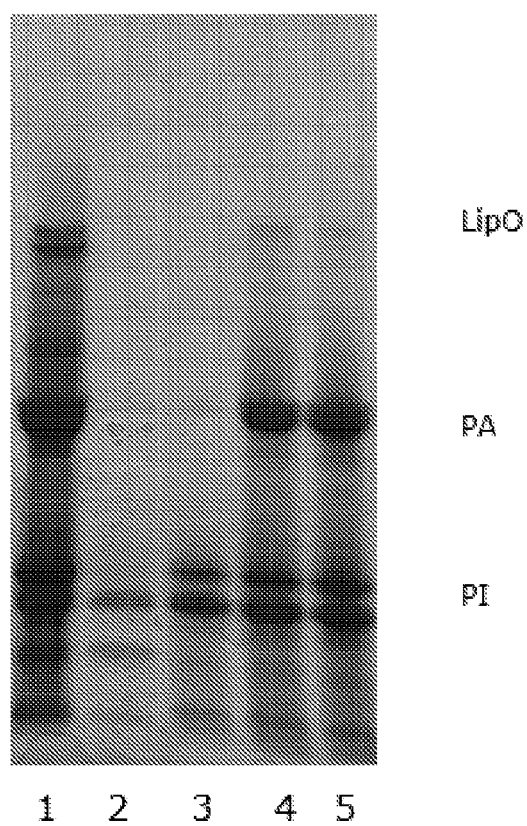

Example 19 Isolating protein from potato juice using silicate polymers 30 ml of potato juice produced according to materials and methods (test solution 1) is mixed with 1 ml of a concentrated solution of sodium metasilicate, technical grade waterglass (Matas, Denmark) 36-38 degrees Baumé, dry matter concentration 52 wt %. Addition of the waterglass is performed in aliquots of 0.25 ml and pH is immediately adjusted to pH 7 with 1 M hydrochloric acid in between each addition. When the full amount of waterglass has been added the sample is adjusted to a final pH of 6.1. Following incubation for 5 minutes with stirring at ambient temperature the sample is divided into three 10 ml centrifuge tubes and centrifuged for 5 min at 1430 g and the supernatant from each tube is poured back into one container (test solution 2). The precipitate remaining in each centrifuge tube is resuspended in 6 ml water and then centrifuged again. This procedure is repeated twice. Following the last centrifugation the water washing supernatants are discarded while the precipitates are transferred into small beakers under addition of 6 ml water each. The beakers are labelled A-C and adjusted to varying pH values with 1 M hydrochloric acid under stirring as follows: A) pH 2.8, B) pH 1.9, C) pH 1.4. The samples are then incubated with stirring for 10 min at ambient temperature where after they are centrifuged for 5 min at 1430 g. The supernatants A), B) and C) are separated from the remaining precipitate to form test solution 3, 4 and 5 respectively. SDS-PAGE is performed on test solutions 1-5 and as illustrated in FIG. 18.

Figure 19:
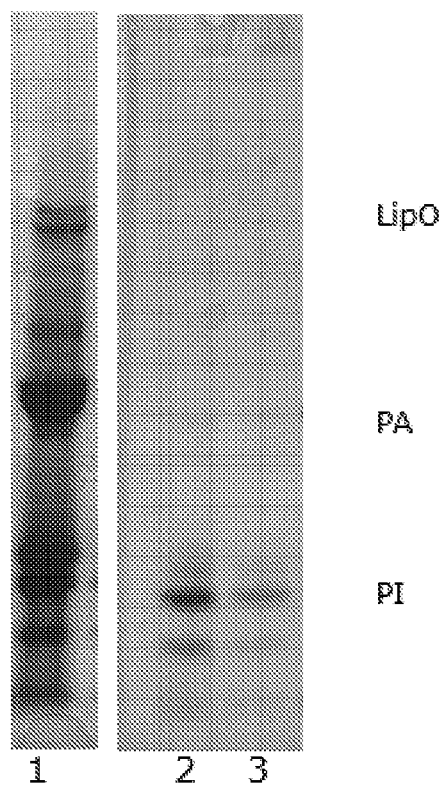

Results:

The SDS PAGE analysis of FIG. 19 illustrates that the sodium metasilicate is able to precipitate almost all the protein present in the potato fruit juice (lane 2 which shows that only a minor fraction of the PI is left in the supernatant). Further, it can be seen, that after washing of the precipitate with water and then incubating at pH 2.8 results in a highly selective release of PI proteins (lane 3) without any PA being released from the precipitate. Lowering the pH of the incubation to pH 1.9 or pH 1.4 (lane 4 and 5) results in an almost complete elution of PA and PI while the LipO remains in the remaining precipitate.

For all the elutions (test solution 3-5) it is observed that the released proteins are practically colorless while the corresponding precipitates are yellow-brown indicating that the colored polyphenols to a very large extent are separated from the released proteins.

Example 20 Isolating Protein from Potato Juice Using Silicate Polymers 30 ml of potato juice produced according to materials and methods (test solution 1, true protein concentration 13 g/L) is divided into 2 samples (A and B respectively) of 15 ml juice and each mixed with 0.3 ml respectively 0.6 ml of a concentrated sodium silicate solution, reagent grade water glass (Sigma Aldrich, USA cat. No.: 338443, $Na_2O$=10.6%, $SiO_2$=26.5%) density 1.39 g/ml at 25° C. Addition of the water glass is performed in aliquots of 0.15 ml and pH is immediately adjusted to pH 7 with 1 M hydrochloric acid in between each addition. When the full amount of water glass has been added the samples are adjusted to a final pH value of 6.0. Following incubation for 5 minutes with stirring at ambient temperature the samples are centrifuged for 5 min at 1430 G. The supernatants A) and B) are separated from the remaining precipitate to form test solution 2 and 3 respectively. SDS-PAGE is performed on test solutions 1, 2 and 3 as illustrated in FIG. 19.

Results:

The SDS PAGE analysis of FIG. 19 illustrates that the sodium silicate solution from Sigma Aldrich is capable of precipitating almost all the protein present in the potato fruit juice at pH 6.0. The more water glass added to the juice the more protein is precipitated. Lane 2 shows that only a minor fraction of the PI is left in the supernatant A (0.3 ml water glass). Lane 3 shows even fainter bands for the PI left in the supernatant B (0.6 ml water glass.

Example 21 Isolating Protein from Potato Juice Using Sodium and Calcium Silicate (Addition of Solids to the Juice)

100 ml of potato juice produced according to materials and methods (test solution 1, true protein concentration 13 g/L) is mixed with 700 mg sodium metasilicate powder respectively 350 mg sodium metasilicate powder (Sigma Aldrich, USA cat. No.: 307815). While the mixing with the sodium metasilicate creates an increase in this is continuously adjusted and stabilized at pH 6.1 with 1 M hydrochloric acid over a period of 10 min. Following incubation for 15 minutes with stirring at ambient temperature the samples are centrifuged for 5 min at 1430 G. The supernatants A) and B) (respectively 700 and 350 mg sodium metasilicate) are separated from the remaining precipitate to form test solution 2 and 3 respectively.

10 ml of the same batch of potato juice (test solution 1) is mixed with 100 mg calcium silicate (Sigma Aldrich, USA cat. No.: 742503) and pH is adjusted to pH 6.0 with 1 M hydrochloric acid. Following incubation for 15 minutes with stirring at ambient temperature the sample is centrifuged for 5 min at 1430 G. The supernatant C) is separated from the remaining precipitate to form test solution 4. SDS-PAGE is performed on test solutions 1, 2, 3 and 4 as illustrated in FIG. 20.

Figure 20:
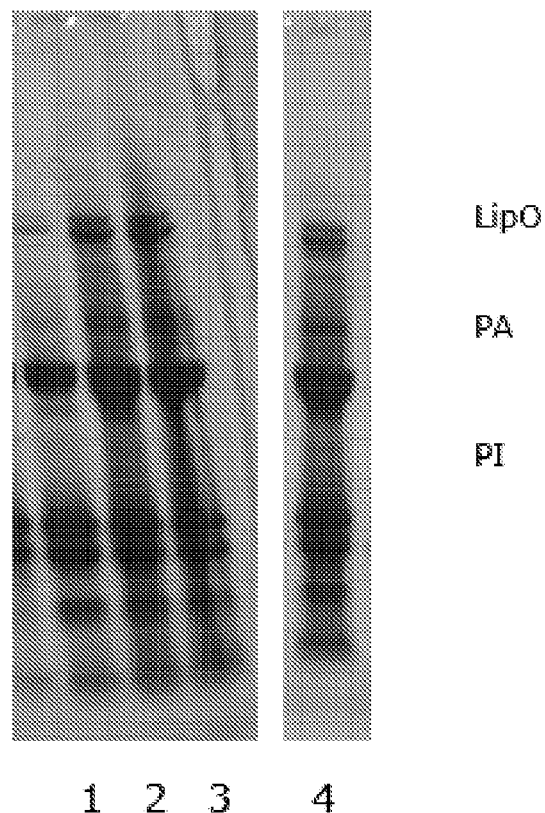

Results:

The SDS PAGE analysis of FIG. 20 illustrates that in contrast to the addition of soluble sodium silicate (water glass, see e.g. previous examples) the solid sodium silicate when adding 700 mg per 100 ml juice only precipitates rather selectively the LipO while the PI stay in solution together with most of the PA (see lane 1, very weak LipO band in the supernatant A). When adding 350 mg sodium silicate per 100 ml juice the major content of potato proteins stay in solution (see lane 2). Addition of calcium silicate does not precipitate any significant amount of proteins (see lane 4).

Example 22. Synthesis of Polysiloxanes with Organic Functional Groups

Five solutions comprising different organic functional groups and labelled A) through E) are prepared by mixing at ambient temperature as follows:

Solution A:
20 ml water is added 2 g 4-aminobenzoic acid (Sigma Aldrich, USA, cat. no.: A9878) followed by adjustment of pH to 11.8 with 5 M sodium hydroxide.

Solution B:
20 ml water is added 2 g 4-mercaptobenzoic acid (Sigma Aldrich, USA, cat. no.: 706329) followed by adjustment of pH to 11.0 with 5 M sodium hydroxide.

Solution C:
20 ml water is added 2 g hexylamine (Sigma Aldrich, USA, cat. no.: 219703).

Solution D:
20 ml water is added 2 g benzylamine (Sigma Aldrich, USA, cat. no.: A9878).

Solution E:
20 ml water is added 2 g benzylaminoethanol (Sigma Aldrich, USA, cat. no.: B22003).

To each solution is then added 5 ml glycidoxypropyltrimethoxysilane (Sigma Aldrich, USA, cat. no.: 440167) under constant stirring and the temperature is increased to 40 degrees Celsius. The reaction is carried out for 18 hours after which the solutions are cooled to ambient temperature and each applied for dialysis against 5 L demineralized water in dialysis tubing cellulose membranes (Sigma-Aldrich, USA, cat. No.: D9652). The dialysis is continued for 48 hours at ambient temperature with 4 shifts of the water. Following removal of any surplus and unreacted reactants by dialysis acid-base titrations and elemental analysis for determination of nitrogen, sulfur and silicon confirm that the glycidoxypropyltrimethoxysilane reacts with the added organic functional groups. All solutions also form a heavy precipitate upon acidification with hydrochloric acid.

Example 23. Isolation of Potato Proteins Using Polysiloxanes Coupled with Organic Functional Groups 50 ml of potato juice produced according to materials and methods (test solution 1, protein concentration 10 g/L) is mixed with a solution of the polysiloxane-4-mercatobenzoic acid derivative prepared according to example 22 to reach a final concentration of 10 mg polysiloxane derivative per ml potato juice and pH is adjusted to pH 5.1 at ambient temperature. A heavy precipitate is formed. Following mixing for 5 minutes the mixture is centrifuged at 1430 g for 10 minutes. The resulting supernatant is decanted (test solution 2) and analyzed by SDS-PAGE according to materials and methods. From the SDS-PAGE analysis it is concluded that most of the PI in the sample is bound while only a smaller fraction of the PA is removed.

Example 24. Pre-Treatment of Potato Juice with Calcium Chloride and Water Glass 200 ml of potato juice produced according to materials and methods (test solution 1, true protein concentration 11 g/L) is divided into 2 samples (A and B respectively) of 100 ml juice. Calcium chloride (1 M solution) and water glass solution (from Borup Kemi, Denmark, 36° BE) are added in the following concentrations:

A: 0 ml 1 M $CaCl_2$)+0 ml water glass=reference
B: 1 ml 1 M $CaCl_2$) (10 mM)+0.5 ml water glass The solutions are incubated for 1 hr at room temperature. The solutions are then centrifuged in 2 separate tubes for 10 min at 1430 g and the supernatants are collected (test solutions 2 and 3 respectively). The turbidity of the supernatants is measured by spectrophotometry at 620 nm.

The test solutions are then freeze dried and the amount of glycoalkaloids (solanine and chaconine) are determined in the two dried products. Protein composition is determined by SDS-PAGE.

Results:

Table 3 below shows the 620 nm reading and glycoalkaloid content of the dry substances derived from test solution 2 and 3.

| Test solution | 620 nm reading | Solanine, ppm | Chaconine, ppm |
| --- | --- | --- | --- |
| 2 (reference) | 0.721 | 1336 | 107 |
| 3 | 0.313 | 1026 | 0 |

It is concluded that a pre-treatment of the juice with calcium chloride and water glass, reduces the turbidity significantly compared to the untreated reference. The content of chaconine in the pretreated solution is eliminated completely while the solanine content is reduced with 23%.

Analysis by SDS-PAGE revealed no significant change in the composition and concentration of the major protein groups in the pretreated sample compared to the reference.

Example 25. Pre-Treatment of Potato Juice with Different Calcium Chloride and Water Glass Concentrations 2400 ml of potato juice produced according to materials and methods (test solution 1, true protein concentration 11 g/L) is divided into 4 samples (A, B, C and D respectively) of 600 ml juice. Calcium chloride (1 M solution) and water glass solution (from Borup Kemi, Denmark, 36° BE) are added in the following concentrations:
A: 6 ml 1 M CaCl$_2$) (10 mM)+3 ml water glass (5 ml/L)
B: 6 ml water (0 mM)+3 ml water glass (5 ml/L)
C: 12 ml 1 M CaCl$_2$) (20 mM)+3 ml water glass (5 ml/L)
D: 12 ml 1 M CaCl$_2$) (20 mM)+4.5 ml water glass (7.5 ml/L)

The solutions are incubated for 1 hr at room temperature. The solutions are then centrifuged in 4 separate tubes for 10 min at 1430 g and the supernatants are collected (test solutions 2-5 respectively). The turbidity of the supernatants and non-treated juice is measured by spectrophotometry at 620 nm.

Results:
Table 4 shows the 620 nm reading for test solutions 1-5.

| Test solution | CaCl2, mM | Water glass ml/L | 620 nm reading |
|---|---|---|---|
| 1 | 0 | 0.0 | 0.721 |
| 2 | 10 | 5.0 | 0.313 |
| 3 | 0 | 5.0 | 0.366 |
| 4 | 20 | 5.0 | 0.243 |
| 5 | 20 | 7.5 | 0.186 |

The experiment shows that by adding only water glass at 5 ml/L juice the 620 nm signal is reduced from 0.721 to 0.366 relative to the untreated juice (test solution 1). By also adding 10 mM calcium chloride to the juice containing 5 ml/L water glass (test solution 2) the 620 nm signal is decreased further 15% from 0.366 to 0.313. Increasing the concentration of calcium chloride further to 20 mM in juice containing 5 ml/L water glass (test solution 4) reduces the 620 nm signal with further 22% from 0.313 to 0.243. An increase of calcium chloride to 20 mM and the water glass from 5 to 7.5 ml/L juice reduces the 620 nm reading with 74% relative to the untreated juice.

The brown coloration of test solution 4 and 5 were significantly less than in test 1, 2 and 3 indicating an efficiently removal of phenolic compounds such as polyphenols as well.

Analysis by SDS-PAGE revealed no significant change in the composition and concentration of the major protein groups in the pretreated sample compared to the reference.

Example 26. Pre-Treatment of Potato Juice with Calcium Chloride and Water Glass at Different Temperature and Incubation Time 300 ml of potato juice produced according to materials and methods (test solution 1, true protein concentration 11 g/L) is divided into 3 samples (A, B and C respectively) of 100 ml juice. Calcium chloride (1 M solution) and water glass solution (from Borup Kemi, Denmark, 36° BE) are added in the following concentrations to all three samples: 1 ml 1 M CaCl$_2$) (10 mM)+0.5 ml water glass (5 ml/L)

The solutions are then incubated for a total of 1 hr at the following temperatures:
A: Room temperature, 22° C.
B: 30° C. in a controlled temperature water bath
C: 37° C. in a controlled temperature water batch For each temperature, 4 ml samples are withdrawn after 5, 10, 15 and 60 min of incubation.

The withdrawn samples are immediately centrifuged in separate tubes for 5 min at 1430 g and the supernatants are collected (A: test solution 2, 3, 4 and 5 respectively, B: test solution 6, 7, 8 and 9 respectively, C: test solution 10, 11 and 12 respectively). The turbidity of the test solutions is measured by spectrophotometry at 620 nm.

Results:
Table 5 shows the 620 nm reading for test solution 1-13.

| Test solution | Temperature, ° C. | Incubation time, min | 620 nm reading |
|---|---|---|---|
| 1 | 22 | — | 1.043 |
| 2 | 22 | 5 | 0.485 |
| 3 | 22 | 10 | 0.427 |
| 4 | 22 | 15 | 0.377 |
| 5 | 22 | 60 | 0.334 |
| 6 | 30 | 5 | 0.358 |
| 7 | 30 | 10 | 0.340 |
| 8 | 30 | 15 | 0.295 |
| 9 | 30 | 60 | 0.252 |
| 10 | 37 | 5 | 0.230 |
| 11 | 37 | 10 | 0.222 |
| 12 | 37 | 15 | 0.196 |
| 13 | 37 | 60 | 0.188 |

The experiment shows that for all three temperatures the turbidity decreases over time while higher temperature leads to a faster and more efficient precipitation of the light scattering substances.

Example 27. Isolating Protein from Pretreated Potato Juice Using Sodium Alginate 700 ml of potato juice produced according to materials and methods (test solution 1, true protein concentration 10 g/L) pretreated with calcium chloride and water glass and centrifuged as described in example A is mixed with 100 ml of 1.5% sodium alginate solution (ligand solution A) and pH is adjusted to 3.5 with 1 M hydrochloric acid under thorough stirring at ambient temperature. The resulting solution is incubated under stirring for 10 min. The solution is then centrifuged for 10 min at 1430 g and the supernatant removed (test solution 2). The precipitate is washed twice by resuspension in 200 ml water at pH 3.0 (with 1 M hydrochloric acid) and repeated centrifugation. The resulting precipitate is then dissolved in 100 ml water by adjustment of pH to pH 7.5 with 1 M NaOH. The dissolved product is dried by freeze drying (Product 1).

The concentration of glycoalkaloids (solanine and chaconine) as well as the protein content (N×6.25) is determined on product 1 after freeze-drying.

Results:
A yield of 7.5 gram dried Product 1 was achieved after freeze drying.

Table 6 shows the content of glycoalkaloids and protein in the freeze-dried product 1.

| Sample | Protein content, % | Solanine, ppm | Chaconine, ppm |
|---|---|---|---|
| Product 1 | 74.6 | 75 | 5 |

Example 28. Isolating a PA Enriched Fraction and a PI Fraction from Pretreated Potato Juice with Sodium Alginate Precipitation Followed by Ultrafiltration 2.2 L of potato juice produced according to materials and methods (test solution 1, true protein concentration 9 g/L) and pretreated with calcium chloride and water glass and centrifuged as described in example A is mixed with 63 ml of 1.5% sodium alginate solution (ligand solution A) and pH is adjusted to pH 3.5 with 1 M hydrochloric acid.

Following mixing for 5 minutes at ambient temperature the sample is centrifuged at 1430 g for 10 min. The supernatant is collected (test solution 2). The precipitate is washed two time by resuspension in water pH adjusted to 3.0 with hydrochloric acid and repeated centrifugation. The precipitate is then suspended in 100 ml water and pH is slowly adjusted to pH 10 with 1 M NaOH during mixing at ambient temperature for 30 min. (test solution 3).

The supernatant (2.25 L, test solution 2) is ultrafiltered at pH 3.5 using a 10 kDa hollow fiber membrane. When 2.05 L permeate (test solution 4) is collected the retentate is diafiltered with six additions of 200 mL water pH adjusted with hydrochloric acid to 3.0. The permeate of each addition of diafiltration water is pooled and denoted test solution 5, while the retentate resulting from the diafiltration is denoted test solution 6.

Figure 21:
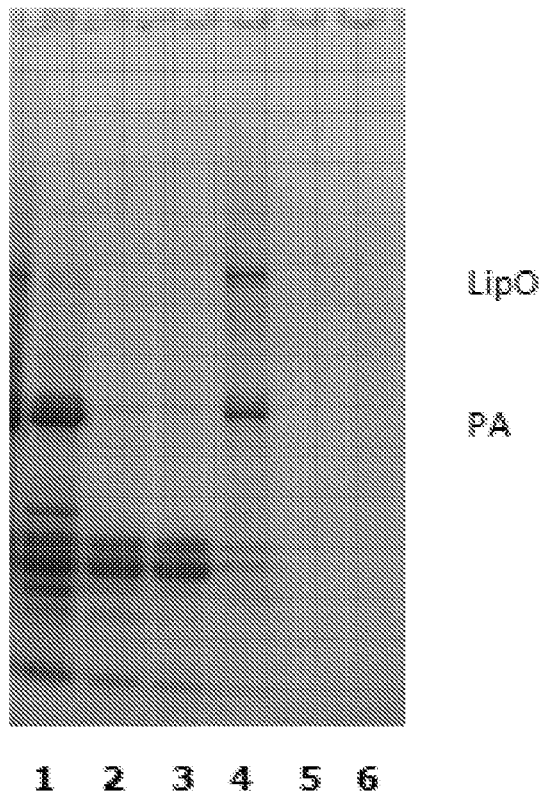

The test solutions are analyzed with SDS-PAGE as illustrated in FIG. 21-22.

Test solution 3 and 6 are freeze dried resulting in respectively product 1 (PA enriched fraction) and product 2 (PI enriched fraction). The concentration of glycoalkaloids (solanine and chaconine) is determined in dried product 1 and product 2. Furthermore the protein content (N×6.25) is determined in dried product 1 and product 2.

Results:

The SDS-PAGE of FIG. 21-22 illustrates that the supernatant from the alginate precipitation (see lane 2) contains only a very small fraction of the PA compared to the starting material. The major part of PI is still in solution resulting in a highly enriched PI fraction, product 2 (see lane 3, strong PI bands in retentate).

The dissolved precipitate contains PA and only a minor fraction of PI resulting in a highly enriched PA product (product 1), see lane 4.

The ultrafiltered and diafiltered PI enriched product (see lane 3) have very similar protein profile as the supernatant from the alginate precipitation (see lane 2) meaning that only a very small amount of protein pass through the 10 kDa hollow fiber membrane during ultrafiltration and diafiltration when performed at pH 3.5 (see lane 5 and 6, no protein bands are detected in test solution 4 and 5).

The yield of product 1 was 11.2 g

The yield of product 2 was 10.4 g

Table 7 shows the content of glycoalkaloids and protein in the freeze dried product 1 and product 2.

| Sample | Protein content, % | Solanine, ppm | Chaconine, ppm |
|---|---|---|---|
| Product 1 (PA enriched) | 73.2 | 54 | <10 |
| Product 2 (PI enriched) | 83.7 | 270 | <10 |

Example 29. Pre-Treatment of Potato Juice with Different Calcium Chloride and Water Glass Concentrations at Room Temperature (20-22° C.)

400 ml of potato juice produced according to materials and methods (test solution 1, true protein concentration 11 g/L) is divided into 4 samples (A, B, C and D respectively) of 100 ml juice. Calcium chloride (1 M solution) and water glass solution (from Borup Kemi, Denmark, 36° BE) are added in the following concentrations:

A: 1 ml 1 M $CaCl_2$) (10 mM)+0.67 ml water glass (6.7 ml/L)
B: 1 ml water (0 mM)+0.67 ml water glass (6.7 ml/L)
C: 1 ml 1 M $CaCl_2$) (10 mM)+0.5 ml water glass (5.0 ml/L)
D: 1 ml water (0 mM)+0.5 ml water glass (5.0 ml/L)

For each solution, 5 ml samples are withdrawn after 5, 10, 15 and 30 min of incubation.

The withdrawn samples are immediately centrifuged in separate tubes for 5 min at 1430 g and the supernatants are collected (A: test solution 2, 3, 4 and 5 respectively, B: test solution 6, 7, 8 and 9 respectively, C: test solution 10, 11, 12 and 13 respectively, D: test solution 14, 15, 16 and 17 respectively). The turbidity of the test solutions is measured by spectrophotometry at 620 nm.

Results:

Table 8 shows the 620 nm reading for test solutions 1-17.

| Test solution | CaCl2, mM | Water glass, ml/L | Incubation time, min | 620 nm reading |
|---|---|---|---|---|
| 1 | 0 | 0 | — | 1.043 |
| 2 | 10 | 6.7 | 5 | 0.432 |
| 3 | 10 | 6.7 | 10 | 0.298 |
| 4 | 10 | 6.7 | 15 | 0.277 |
| 5 | 10 | 6.7 | 30 | 0.278 |
| 6 | 0 | 6.7 | 5 | 0.480 |
| 7 | 0 | 6.7 | 10 | 0.357 |
| 8 | 0 | 6.7 | 15 | 0.331 |
| 9 | 0 | 6.7 | 30 | 0.321 |
| 10 | 10 | 5.0 | 5 | 0.416 |
| 11 | 10 | 5.0 | 10 | 0.425 |
| 12 | 10 | 5.0 | 15 | 0.390 |
| 13 | 10 | 5.0 | 30 | 0.347 |
| 14 | 0 | 5.0 | 5 | 0.454 |
| 15 | 0 | 5.0 | 10 | 0.452 |
| 16 | 0 | 5.0 | 15 | 0.416 |
| 17 | 0 | 5.0 | 30 | 0.373 |

The experiment shows that for all the test solutions the turbidity decreases over time while a higher water glass concentration leads to a more efficient precipitation of the light scattering substances. Addition of 10 mM Calcium chloride results in a lower turbidity than solutions without calcium chloride for both concentrations of water glass.

Example 30. Pre-Treatment of Potato Juice with Different Calcium Chloride and Water Glass Concentrations at 35° C.

400 ml of potato juice produced according to materials and methods (test solution 1, true protein concentration 11 g/L) is divided into 4 samples (A, B, C and D respectively) of 100 ml juice. Calcium chloride (1 M solution) and water glass solution (from Borup Kemi, Denmark, 36°BE) are added in the following concentrations:

A: 0 ml 1 M $CaCl_2$) (0 mM)+0 ml water glass (0 ml/L)
B: 1 ml 1 M $CaCl_2$) (10 mM)+0 ml water glass (0 ml/L)
C: 1 ml 1 M $CaCl_2$) (10 mM)+0.33 ml water glass (3.33 ml/L)
D: 1 ml 1 M $CaCl_2$) (10 mM)+0.25 ml water glass (2.5 ml/L)

For each solution, 5 ml samples are withdrawn after 5, 10, 15 and 30 min of incubation at 35° C. in a controlled temperature water bath.

The withdrawn samples are immediately centrifuged in separate tubes for 5 min at 1430 g and the supernatants are collected (A: test solution 2, 3, 4 and 5 respectively, B: test solution 6, 7, 8 and 9 respectively, C: test solution 10, 11, 12 and 13 respectively, D: test solution 14, 15, 16 and 17 respectively). The turbidity of the test solutions is measured by spectrophotometry at 620 nm.

Results:
Table 9 shows the 620 nm reading for test solutions 1-17.

| Test solution | CaCl2, mM | Water glass, ml/L | Incubation time, min | 620 nm reading |
| --- | --- | --- | --- | --- |
| 1 | 0 | 0 | — | 1.043 |
| 2 | 0 | 0 | 5 | 0.604 |
| 3 | 0 | 0 | 10 | 0.574 |
| 4 | 0 | 0 | 15 | 0.576 |
| 5 | 0 | 0 | 30 | 0.575 |
| 6 | 10 | 0 | 5 | 0.529 |
| 7 | 10 | 0 | 10 | 0.498 |
| 8 | 10 | 0 | 15 | 0.510 |
| 9 | 10 | 0 | 30 | 0.496 |
| 10 | 10 | 3.33 | 5 | 0.346 |
| 11 | 10 | 3.33 | 10 | 0.336 |
| 12 | 10 | 3.33 | 15 | 0.311 |
| 13 | 10 | 3.33 | 30 | 0.315 |
| 14 | 10 | 2.5 | 5 | 0.416 |
| 15 | 10 | 2.5 | 10 | 0.397 |
| 16 | 10 | 2.5 | 15 | 0.375 |
| 17 | 10 | 2.5 | 30 | 0.370 |

The experiment shows that when incubating at 35° C. the effect of the pre-treatment is practically complete within 10 minutes. The addition of calcium chloride and water glass decreases the turbidity most efficiently.

Example 31. Pre-Treatment of Potato Juice with Water Glass at Different Concentrations 800 ml of potato juice produced according to materials and methods (test solution 1, true protein concentration 11 g/L) is divided into 4 samples (A, B, C and D respectively) of 200 ml juice. Water glass solution (from Borup Kemi, Denmark, 36° BE) are added in the following volumes:

A: 10 ml/L
B: 6.7 ml/L
C: 5 ml/L
D: 5 ml/L+2 ml 1 M $CaCl_2$) (10 mM)=reference solution The solutions A, B and C are then incubated for 1 hr at room temperature (20-22° C.). Solution D is incubated for 1 hr at 35° C. in a controlled temperature water bath.

The samples are immediately centrifuged in separate tubes for 10 min at 1430 g and the supernatants are collected (A: test solution 2, B: test solution 3, C: test solution 4, D: test solution 5). The turbidity of the test solutions is measured by spectrophotometry at 620 nm.

Results:
Table 10 shows the 620 nm reading for test solution 1-5.

| Test solution | Temperature | CaCl2, mM | Water glass ml/L | 620 nm reading |
| --- | --- | --- | --- | --- |
| 1 | Room temp. | 0 | 0.0 | 0.721 |
| 2 | Room temp. | 0 | 10.0 | 0.223 |
| 3 | Room temp. | 0 | 6.7 | 0.428 |
| 4 | Room temp. | 0 | 5.0 | 0.642 |
| 5 | 35° C. | 10 | 5.0 | 0.271 |

The experiment shows that the turbidity decreases when the concentration of water glass increases and a more efficient precipitation of the light scattering substances is achieved. Elevated temperature (35° C.) decreases the turbidity significantly even at the relatively lower concentration of water glass.

Example 32. Isolating a PA Enriched Fraction with pH Adjustment from Pretreated Potato Juice (with Water Glass)

200 ml of potato juice produced according to materials and methods (test solution 1, true protein concentration 11 g/L) is pre-treated by addition of 2 ml water glass solution (from Borup Kemi, Denmark, 36° BE) followed by incubation at room temperature (20-22° C.) for 1 hr. The sample is then centrifuged for 10 min at 1430 g and the supernatant is collected (test solution 2). The turbidity of test solution 2 is measured by spectrophotometry at 620 nm.

Test solution 2 is then adjusted to pH 3.0 with 1 M hydrochloric acid. The sample is then centrifuged again at 1430 g for 10 min. The supernatant is collected (test solution 3). The turbidity of test solution 3 is measured by spectrophotometry at 620 nm.

The precipitate is washed by resuspension in water pH adjusted to 3.0 with hydrochloric acid and repeated centrifugation (precipitate 1).

Precipitate 1 is then suspended in 50 ml water and pH is slowly adjusted to pH 9 with 1 M NaOH during mixing at ambient temperature, total volume was then 55 ml (test solution 4).

The test solutions are analyzed with SDS-PAGE as illustrated in figure xx.

The dry matter content in the PA enriched product (test solution 4) is determined Results:
The SDS-PAGE of FIG. 22 illustrates that the supernatant from the pH precipitation (see lane 3) contains only a very small fraction of the PA compared to the starting material. The major part of PI is still in solution resulting in a highly enriched PI fraction (see lane 3, strong PI bands). The dissolved precipitate contains PA and only an insignificant fraction of PI resulting in a highly enriched PA product, see lane 4.

Table 11 shows the 620 nm reading for test solution 2 and 3

| Test solution | Sample description | 620 nm reading |
| --- | --- | --- |
| 2 | Pre-treated juice | 0.321 |
| 3 | Supernatant at pH 3 | 0.105 |

The low turbidity of test solution 3 (containing the non-precipitated PI fraction) is highly advantageous for further processing e.g. by membrane filtration or an additional precipitation step.

The dry matter content in test solution 4 was 1.80%, and with a volume of 55 ml this results in a yield of 4.95 g/L potato juice.

When compared to a corresponding dissolved precipitate containing PA from a potato juice that is not pre-treated according to the invention, test solution 4 would have significantly better re-solubilization characteristics and a lower turbidity.

Example 33. Isolating a PI Fraction with pH Adjustment from Immediately Processed Potato Juice Part A 1000 ml of potato juice was produced from raw potatoes as described in materials and methods except that the potatoes and the juicer were pre-heated to 40 degrees Celsius and the initial removal of larger particles by centrifugation was not performed (test solution 1, true protein concentration 8.5 g/L). Within less than 10 minutes from producing the juice and adding the sodium sulfite, test solution 1 was divided into four fractions of each 250 ml and adjusted in pH as follows: The first 250 ml fraction was adjusted to pH 4.0 (test solution 2), the second fraction was adjusted to pH 3.5 (test solution 3), the third fraction was adjusted to pH 3.0 and the fourth fraction was adjusted to pH 2.5. All pH adjustments were performed using 1 M sulfuric acid.

The four fractions were then centrifuged at 1430 G for 10 minutes and the four supernatants separated from the precipitates. The four supernatants were subsequently analysed by SDS-PAGE, scanning densitometry and spectrophotometry to determine the optical density at 620 nm and by an assay to determine the content of polyphenoloxidase as described in materials and methods.

Part B 2000 ml potato juice prepared as in Part A was adjusted to pH 3.0 within less than 10 minutes from producing the juice and centrifuged at 1430 G for 10 minutes. The precipitate from the centrifugation was immediately frozen and stored while the resulting clear supernatant was then ultra-filtered on a 10 kD cut-off hollow fiber cartridge to concentrate the supernatant 10 times and hereafter a diafiltration step using, first 5 retentate volumes of water/H2SO4 pH 3.0 and then 5 retentate volumes of demineralized water was performed. The resulting slightly turbid solution (approx. 200 ml) was subsequently freeze-dried and analysed for protein purity by Kjeldahl nitrogen determination, solanine content, gelling functionality and solubility.

Part C

This test was carried out in the same way as described for Part B above with an additional adsorption step after the last diafiltration step with demineralized water as follows: The retentate (approx. 200 ml) was incubated with mixed at room temperature with 10 ml Dowex optipore L-285 resin (adsorbent from DOW Chemical Company) for 6 hours. Following incubation the suspension was allowed to rest and the resin was allowed to settle. The supernatant above the settled resin was recovered by decantation, freeze dried and analyzed for solanine and chaconine content.

Part D

This test was carried out in the same way as described in Part C except that the resin (adsorbent) used was a Lewatite VP OC 1064 adsorbent (from LanXess).

Results:

Part A

Measured concentrations of lipoxygenase, polyphenoloxidase, PA and PI relative to test solution 1 (100%).

| Supernatant/ Test solution | Lipoxygenase % | Polyphenol oxidase % | PA % | PI % | OD 620 nm |
|---|---|---|---|---|---|
| 2 (pH 4.0) | 35 | Approx. 25 | >85 | >95 | 0.09 |
| 3 (pH 3.5) | <10 | Approx. 10 | 50 | >95 | 0.06 |
| 4 (pH 3.0) | ND | ND | <10 | >95 | 0.03 |
| 5 (pH 2.5) | ND | ND | ND | >95 | 0.03 |

ND: Not detected From these data it is concluded that the highest purity of the PI relative to PA, lipoxygenase and polyphenoloxidase under the conditions tested is achieved by acididification of the juice to pH about 2.5-3.0.

Part B.

The yield of the PI dried protein fraction corresponded to 4.8 g/L test solution 1, corresponding to approx. 95% of the PI present in test solution 1. The freeze-dried PI powder was off-white to slightly yellow, had a bland to slightly acidic taste and was found to be more than 90% soluble in an aqueous phosphate buffer (0.05 M, pH 7.4). A 2% solution in 0.05 M sodium acetate pH 4.5 formed excellent and firm gels by heating to 80 degrees C. for 30 min. The protein content of the powder as determined by the Kjeldahl method was 88% and the solanine content was 145 ppm.

Thus, it is concluded that the applied separation process from crude and freshly made potato juice provides a highly functional and non-denatured PI protein fraction having high purity.

Part C.

The solanine and chaconine content of the freeze dried powder was found to be 35 and 22 ppm respectively which demonstrates that the Dowex adsorbent bound and removed a substantial amount of the glycoalkaloid present in the untreated retentate (see Part B).

Part D.

The solanine and chaconine content of the freeze dried powder was both found to be less than 10 ppm which demonstrates that the Dowex adsorbent bound and removed a substantial amount of the glycoalkaloid present in the untreated retentate (see Part B).

Items of the Invention

1. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, glycoalkaloid and phenolic compounds said method comprising:

a) providing an aqueous phase comprising compounds selected from two or more of PA, PI, PPO, LipO, glycoalkaloid and phenolic compounds of which at least one compound is selected from PA, PI, LipO and PPO;

b) contacting the aqueous phase with a mobile solubilized ligand at physico-chemical conditions allowing formation of a complex between the ligand and the compounds selected from one or more of PA, PI, LipO and PPO;

c) allowing the complex to separate from the aqueous supernatant phase, optionally by changing said physico-chemical conditions in the composition to reduce the solubility of the complex; and d) isolating the complex separated from the aqueous phase.

2. The method of item 1, wherein the separated complex comprises a combination of PA and PI and PPO and wherein the complex separates from the aqueous supernatant phase by precipitation.

3. The method of item 2, wherein the dry weight ratio PA:PI in the precipitate is higher than the dry weight PA:PI ratio for PA and PI remaining dissolved in the aqueous supernatant phase.

4. The method of item 3, further comprising dissolving the precipitated complex in an aqueous solvent and isolating PA from one or more compounds selected from PI and PPO by a mechanical separation process concentrating the PA in the retentate 5. The method of item 3, further comprising isolating the precipitated complex by a mechanical separation process concentrating one or more of PA, PI and PPO in the retentate.

6. The method of item 2, further comprising
a) contacting the aqueous supernatant phase with a further mobile solubilized ligand at physico-chemical conditions in the aqueous supernatant phase allowing formation of a complex between the ligand and compounds selected from one or more of PI, and PPO;
b) allowing the complex to separate from the aqueous supernatant phase, optionally by changing said physico-chemical conditions in the composition to reduce the solubility of the complex so that the complex separates from the aqueous supernatant phase; and
c) isolating the complex.

7. The method of item 2, wherein the sum of PA and PI remaining dissolved in the aqueous supernatant phase is less than 20%, optionally less than 10 wt. % of the total PA and PI.

8. The method of item 7, further comprising dissolving the precipitated complex in an aqueous solvent and isolating PA from one or more compounds selected from PI, and PPO by a mechanical separation process concentrating the PA in the retentate.

9. The method of item 7, further comprising isolating the precipitated complex by mechanical separation process concentrating the one or more of PA, PI, and PPO in the retentate.

10. The method of item 7, further comprising dissolving the precipitated complex in an aqueous solvent and isolating PA from one or more compounds selected from PI, and PPO by selectively adsorbing the one or more compounds selected from PI and PPO on an immobilized solid carrier at conditions where the carrier will bind the one or more compounds selected from PI and PPO.

11. The method of item 2, wherein the dry weight ratios PI:PA or PPO:PA in the precipitate is higher than the dry weight ratios PI:PA or PPO:PA for PA, PI and PPO remaining dissolved in the aqueous supernatant phase.

12. The method of item 11, further comprising concentrating PA in the aqueous supernatant phase by a mechanical separation process concentrating PA in the retentate, optionally combined with diafiltration.

13. The method of item 11, further comprising
a) contacting the aqueous supernatant phase with a further mobile solubilized ligand at physico-chemical conditions in aqueous supernatant phase allowing formation of a complex between the ligand and PA;
b) allowing the complex to separate from the aqueous supernatant phase, optionally by changing said physico-chemical conditions in the composition to reduce the solubility of the complex so that the complex separates from the aqueous supernatant phase; and
c) isolating the complex.

14. The method of item 11, further comprising adsorbing dissolved PA in the aqueous supernatant phase on an immobilized solid carrier at conditions where the carrier will bind PA.

15. The method of item 1, further comprising pre-treating the aqueous phase of 1a) by adsorbing one or more of PI, LipO and PPO on an immobilized solid carrier at conditions where the carrier will bind the one or more of PI, LipO or PPO.

16. The method of any preceding items, wherein the isolated complex comprises one or more of PA, PI, LipO and PPO.

17. The method of item 16, wherein the isolated complex on a dry weight basis comprises more than 51.9 wt % PA, optionally more than 55 wt % PA, optionally more than 65 wt % PA, optionally more than 75 wt % PA, optionally more than 85 wt % PA, optionally more than 95 wt % PA relative to the total amount of PA, PI, LipO and PPO in the isolated complex.

The method of item 16, wherein the isolated complex comprises more than 88.6 wt % PA of total PA, optionally more than 90 wt % PA of total PA, optionally more than 95 wt % PA of total PA, optionally more than 97 wt % PA of total PA, optionally more than 99 wt % PA of total PA.

18. The method of item 16, wherein the isolated complex on a dry weight basis comprises more than 50 wt % PI, optionally more than 55 wt % PI, optionally more than 65 wt % PI, optionally more than 75 wt % PI, optionally more than 85 wt % PI, optionally more than 95 wt % PI relative to the total amount of PA, PI, LipO and PPO in the isolated complex.

19. The method of item 16, wherein the isolated complex comprises more than 90 wt % PI of total PI, optionally more than 95 wt % PI of total PI, optionally more than 97 wt % PI of total PI, optionally more than 99 wt % PI of total PI.

20. The method of item 16, wherein the isolated complex on a dry weight basis comprises more than 50 wt % PPO, optionally more than 55 wt % PPO, optionally more than 65 wt % PPO, optionally more than 75 wt % PPO, optionally more than 85 wt % PPO, optionally more than 95 wt % PPO relative to the total amount of PA, PI, LipO and PPO in the isolated complex.

21. The method of item 16, wherein the isolated complex comprises more than 90 wt % PPO of total PPO, optionally more than 95 wt % PPO of total PPO, optionally more than 97 wt % PPO of total PPO, optionally more than 99 wt % PPO of total PPO.

22. The method of item 16, wherein the isolated complex relative to the total amount of PA, PI, LipO and PPO in the isolated complex comprises from 60 to 95 wt % PA; and from 0.9 to 39.9 wt % PI and from 0.1 to 4.1 wt % PPO.

23. The method of item 16, wherein the isolated complex comprises from 80-99.9 wt % PA of total PA in the aqueous phase; from 0.1 to 20 wt % PI of total PI in the aqueous phase and from 0.1 to 20 wt % PPO of total PPO in the aqueous phase.

24. The method of any of items 1 to 23, wherein the PA is complexed to the ligand in a PA:ligand dry weight ratio of at least 4:1, optionally at least 8:1, optionally at least 10:1, optionally at least 15:1.

25. The method of any of items 1 to 23, wherein the PI is complexed to the ligand in a PI:ligand dry weight ratio of at least 3:1, optionally at least 5:1, optionally at least 8:1, optionally at least 10:1.

26. The method of any of items 1 to 23, wherein the PPO is complexed to the ligand in a PPO:ligand dry weight ratio of at least 2:1, optionally at least 4:1 optionally at least 7:1

27. The method of any of items 1 to 23, wherein the PA is complexed to the ligand in a PA:ligand dry weight ratio of at least 6:1; the PI is complexed to the ligand in a PI:ligand dry weight ratio of at least 5:1 and the PPO is complexed to the ligand in a PPO:ligand dry weight ratio of at least 2:1, optionally in a PA:ligand dry weight ratio of at least 6:1; the PI is complexed to the ligand in a PI:ligand dry weight ratio of at least 7:1 and the PPO is complexed to the ligand in a PPO:ligand dry weight ratio of at least 2:1.

28. The method of item 3, wherein the PA:PI dry weight ratio in the precipitate is at least 25% higher than the PA:PI dry weight ratio for PA and PI remaining dissolved in the aqueous supernatant phase, optionally at least 50% higher, optionally at least 75% higher.

29. The method of item 7, wherein the sum of PA and PI remaining dissolved in the aqueous supernatant phase is less than 15 wt. % of the total PA and PI, optionally less than 12%, optionally less than 10%, optionally less than 8%, optionally less than 6%, optionally less than 5%, optionally less than 4%, optionally less than 3%, optionally less than 2%, optionally less than 1%, optionally less than 0.5%.

30. The method of any of items 1 to 29, wherein the complex contains less than 200 milligrams of glycoalkaloid per kilogram dry matter, optionally less than 150, optionally less than 110, optionally less than 95 mg, optionally less than 80, optionally less than 65, optionally less than 45, optionally less than 25, optionally less than 10 milligram glycoalkaloid per kilogram dry matter.

31. The method of any of items 1 to 29, wherein at least 50%, optionally at least 65%, optionally at least 75%, optionally at least 82%, optionally at least 89%, optionally at least 93% of the glycoalkaloid in the aqueous phase remains in the aqueous supernatant phase after separation of the complex.

32. The method of any of items 1 to 29, wherein the complex contains less than 300 milligram phenolic compounds per kilogram dry matter. optionally less than 250, optionally less than 200, optionally less than 150, optionally less than 125, optionally less than 95, optionally less than 70, optionally less than 35 milligram phenolic compounds per kilogram dry matter.

33. The method of any of items 1 to 29, wherein at least 50%, optionally at least 65%, optionally at least 75%, optionally at least 85%, optionally at least 90% of the phenolic compounds in the aqueous phase remains in the aqueous supernatant phase after separation of the complex.

34. The method of any preceding items, wherein the phenolic compound is chlorogenic acid.

35. The method of item 34, wherein the complex comprise, on a dry weight basis, less than 120 mg/kg of chlorogenic acid, optionally less than 100 mg/kg, optionally less than 80 mg/kg, optionally less than 60 mg/kg, optionally less than 40 mg/kg, optionally less than 20 mg/kg, optionally less than 10 mg/kg.

36. The method of any preceding items, wherein the aqueous phase of step a) comprise an aqueous solution liberated when disintegrating a portion of a plant optionally a tuber portion of a plant of the genus *Solanum*, optionally of the species *S. tuberosum*.

37. The method of item 36, wherein the aqueous phase of step a) comprise the liberated aqueous solution diluted with less than 50 wt % added solvent, optionally less than 25 wt % added solvent, optionally less than 20 wt % added solvent, optionally less than 15 wt % added solvent, optionally less than 10 wt % added solvent, optionally less than 5 wt % added solvent, optionally less than 2 wt % added solvent, optionally less than 1 wt % added solvent.

38. The method of item 36 to 37, wherein the aqueous phase of step a) comprise at least 3 grams protein per litre, optionally at least 5 g/L, optionally at least 8 g/L, optionally at least 10 g/L, optionally at least 12 g/L, optionally between 5 to 25 g/L, optionally between 6 to 20 g/L, optionally between 7 to 15 g/L, optionally between 8 to 12 g/L, optionally between 9 to 11 g/L.

39. The method of item 38, wherein 30 to 50% of the protein in the aqueous phase of step a) is PA.

40. The method of item 38, wherein 30 to 50% of the protein in the aqueous phase of step a) is PI.

41. The method of item 38, wherein at least 60% of the protein in the aqueous phase of step a) is PA or PI.

42. The method of item 38, wherein the aqueous phase of step a) comprise at least 50 mg/kg, optionally at least 75 mg/kg, optionally at least 100 mg/kg, optionally at least 125 mg/kg, optionally at least 150 mg/kg, optionally at least 175 mg/kg, optionally at least 200 mg/kg, optionally at least 250 mg/kg, optionally at least 300 mg/kg, optionally between 50-400 mg/kg, optionally between 75-350 mg/kg, optionally between 100-300 mg/kg glycoalkaloid.

43. The method of item 38, wherein the aqueous phase of step a) comprise at least 10 mg/kg, optionally at least 25 mg/kg, optionally at least 50 mg/kg, optionally at least 125 mg/kg, optionally at least 170 mg/kg, optionally at least 225 mg/kg, optionally at least 300 mg/kg, optionally at least 400 mg/kg, optionally at least 600 mg/kg, optionally between 25 to 2000 mg/kg, optionally between 75 to 1500 mg/kg, optionally between 200 to 1000 mg/kg phenolic compounds.

44. The method of item 36 to 43, wherein the aqueous phase consists of the aqueous solution liberated when disintegrating the said plant portion.

45. The method of item 36 to 44, wherein said disintegration includes shredding, crushing, squeezing or pressurizing the plant portion.

46. The method of item 36 to 45, wherein the plant portion is unpeeled before disintegration.

47. The method of item 36 to 46, wherein the tuber portion is a common potato.

48. The method of item 36 to 47, further comprising separating insoluble solid components, including suspended fibres, of the disintegrated plant portion from the liberated aqueous solution.

49. The method of any preceding item, wherein the ligand is a functional group comprised in a polymer.

50. The method of item 49, wherein the functional group is selected from one or more of hydrophobic, amphiphilic and hydrophilic groups, optionally an organic group.

51. The method of item 50, wherein the functional group is selected from one or more of anionic groups, cationic groups, aryl groups, aromatic groups, heteroaromatic groups and alkyl groups.

52. The method of item 51, wherein the functional group is selected from one or more of carboxyl, sulphate, sulphonate, phosphate, phosphonate, silicate and silicone groups.

53. The method of item 52, wherein the functional group is selected from one or more of aromatic sulfonic acids including polystyrene sulfonic acid (PSS), aromatic carboxylic acids, aromatic phosphonic acids 54. The method of items 49 to 53, wherein the ligand comprises a negative charge at pH 5, optionally at pH 4.5, optionally at pH 4.0, optionally at pH 3.5, optionally at pH 3.

55. The method of item 49 to 54, wherein the polymer has an average molecular size of at least 500 KDa, optionally at least 1500, optionally at least 5.000 kDa, optionally between 5,000 to 10,000,000 KDa, optionally between 10,000 to 1,000,000 KDa, optionally between 10,000 to 500,000 KDa, optionally between 10,000 to 200,000 KDa, optionally between 12,000 to 190,000 KDa. optionally between 200,000 to 400,000 KDa.

56. The method of items 49 to 55, wherein the polymer is linear.

57. The method of items 49 to 55, wherein the polymer is branched.

58. The method of items 49 to 57, wherein the ligand is capable of binding to PA, PI, LipO or PPO by bonds selected from one or more of hydrogen bonds, hydrophobic bonds, $\pi$-$\pi$ (pi-pi) bonds and ionic bonds.

59. The method of items 49 to 58, wherein the polymer in aqueous solution at pH 7 and 20° C. has a solubility of at least 50 g/L, optionally at least 100 g/L.

60. The method of items 49 to 59, wherein the polymer in aqueous solution at a concentration of 50 g/L, at pH 7 and at 20° C. has a shear viscosity of less than 100000, optionally less than 50000, optionally less than 25000 cP.

61. The method of items 49 to 60, wherein the polymer in aqueous solution provides a liquid selected from a shear thinning liquid, a Newtonian liquid and a thixotropic liquid.

62. The method of items 49 to 61, wherein the polymer in aqueous solution has an isoelectric point of less than pH 4.

63. The method of items 49 to 62, wherein the polymer in aqueous solution has a net negative charge at pH less than 7, optionally less than pH 6, optionally less than pH 5, optionally less than pH 4.5, optionally less than pH 4.0

64. The method of items 49 to 63, wherein the polymer in aqueous solution at pH 7 comprise at least 0.5 millimoles anionic groups per gram polymer, such as at least 2 millimoles anionic groups per gram polymer, such as at least 4 millimoles anionic groups per gram polymer, such as between 0.5 to 8 millimoles anionic groups per gram polymer, such as 1 to 7 millimoles anionic groups per gram polymer, such between 2 to 6 millimoles anionic groups per gram.

65. The method of items 49 to 64, wherein the polymer is an inorganic polymer, optionally comprising one or more organic groups.

66. The method of item 65, wherein the polymer comprises silicon, optionally in the form of a silicate or a silicone or a combination thereof.

67. The method of item 66, wherein the polymer comprises a silicone derivatized with the functional group.

68. The method of items 49 to 67, wherein the polymer is solubilized prior to contacting with the compounds selected from two or more of PA, PI, PPO, LipO, glycoalkaloid and phenolic compounds.

69. The method of items 49 to 68, wherein the polymer is added to the aqueous phase in the form of a preparation of the polymer in an aqueous solvent.

70. The method of items 49 to 64, wherein the polymer is a naturally occurring polymer.

71. The method of item 70, wherein the polysaccharide is a naturally occurring polysaccharide.

72. The method of item 71, wherein the polysaccharide is selected from one or more of chitosanate, carrageenanate, alginate, pectinate, agarose, xanthan gum, gum Arabic and dextran.

73. The method of items 49 to 64, wherein the polymer is a synthetic polymer. 74. The method of item 73, wherein the polymer is a derivatized naturally occurring polysaccharide.

75. The method of item 74, wherein the derivatized naturally occurring polysaccharide is selected from one or more of dextran sulphate, carboxymethyl dextran, carboxymethylcellulose (CMC), carboxymethyl starch, cellulose sulphate, starch sulphate, cellulose phosphate, cellulose phosphonate, starch phosphate, starch phosphonate.

76. The method of item 73, wherein the synthetic polymer is selected from one or more of polyacrylic acids (PAA), polymethacrylic acids (PMAA) and polyvinylsulfonic acids (PVS), silicones, and derivatives hereof.

77. The method of any preceding items, further comprising adsorbing compounds selected from one or more of PA, PI, LipO, PPO, glycoalkaloid and phenolic compounds to a solid immobilized carrier, wherein the immobilized solid carrier, optionally comprising a porous cross-linked polymer comprising a ligand capable of binding to the one or more of PA, PI, LipO, PPO, glycoalkaloid and phenolic compounds.

78. The method of item 77, wherein the polymer is the polymer of items 49 to 67 or items 70 to 76.

79. The method of items 77 to 78, wherein the cross-linking is non-covalent.

80. The method of items 77 to 78, wherein the cross-linking is covalent.

81. The method of items 77 to 80, wherein the immobilized carrier is in the form of a porous powder or bead.

82. The method of items 77 to 81, wherein the immobilized carrier at the selected conditions adsorbs more PI than compounds selected from one or more of PA, LipO and PPO.

83. The method of items 77 to 81, wherein the immobilized carrier at the selected conditions adsorbs more PA than compounds selected from one or more of PI, LipO and PPO.

84. The method of item 77 to 81, wherein the immobilized carrier at the conditions adsorbs more PPO and LipO than compounds selected from one or more of PA an PI.

85. The method of items 77 to 81, wherein the immobilized carrier at the conditions adsorbs more compounds selected from one or more of PI, LipO and PPO than PA.

86. The method of items 77 to 81, wherein the immobilized carrier at the conditions adsorbs more compounds selected from one or more of PI and PA than PPO and LipO.

87. The method of items 77 to 81, wherein the immobilized carrier at the conditions adsorbs more compounds selected from one or more of PPO, LipO and PA than PI.

88. The method of items 77 to 81, wherein the immobilized carrier at the conditions adsorbs more compounds selected from one or more of glycoalkaloid and phenolic compounds than compounds selected from one or more of PPO, PA, LipO and PI.

89. The method of any preceding items, wherein the complex formation between the ligand and the compound selected from one or more of PA, PI, LipO, PPO, glycoalkaloid and phenolic compounds is carried out in aqueous phase at pH 7 or less, optionally pH 6 or less, optionally pH 5.0 or less, optionally pH 4.6, optionally pH 4.5 or less, pH 2 or more, optionally pH 3 or more, optionally pH between 3.5 to 4, optionally pH between 5 to 6.

90. The method of any preceding items, wherein the complex formation between the ligand and the compound selected from one or more of PA, PI, LipO, PPO, glycoalkaloid and phenolic compounds is carried out in aqueous phase having a conductivity of at least 5 mS/cm, optionally at least 7 mS/cm, optionally at least 9 mS/cm, optionally at least 10 mS/cm, optionally at least 12 mS/cm, optionally between 5-20 mS/cm, optionally between 8-15 mS/cm, optionally between 9-13 mS/cm.

91. The method of any preceding items, wherein the complex formation between the ligand and the compound selected from one or more of PA, PI, LipO, PPO, glycoalkaloid and phenolic compounds is carried out in aqueous phase having a temperature of between 4° C. to 50° C., optionally between 10° C. to 45° C., optionally between 12° C. to 40° C., optionally between 15° C. to 35° C.

92. The method of any preceding items, wherein the complex formation between the ligand and the compound selected from one or more of PA, PI, LipO, PPO, glycoalkaloid and phenolic compounds is carried out in aqueous phase having a polymer concentration between 0.1 to 50 g/L, optionally between 0.2 to 20 g/L, optionally between 0.2 to 5 g/L, optionally between 0.2 to 3 g/L, optionally between 0.2 to 2 g/L, optionally between 0.5 to 3 g/L optionally between 0.5 to 2 g/L, optionally between 1.0 to 10 g/L, optionally between 1.0 to 5 g/L, optionally between 1.0 to 3 g/L.

93. The method of any preceding items, wherein the complex formation between the ligand and the compound selected from one or more of PA, PI, LipO, PPO is carried out in aqueous phase having a protein concentration corresponding to the sum of PA, PI, LipO and PPO of at least 2 g/L g/L. optionally at least 4 g/L, optionally at least 7 g/L, optionally at least 8 g/L, optionally at least 9 g/L, optionally between 2 to 22 g/L, optionally between 3 to 20 g/L, optionally between 5 to 15 g/L, optionally between 6 to 12 g/L, optionally between 7 to 11 g/L.

94. The method of any preceding items, wherein the complex formed between the ligand and the compound selected from one or more of PA, PI, LipO and PPO comprise between 0.01 mg to 0.5 mg, optionally 0.03 mg to 0.3 mg, optionally 0.05 mg to 0.3 mg complexed polymer per mg complexed protein.

95. The method of any preceding items, wherein the complex between the mobile solubilized ligand and the compound separates from the aqueous supernatant by changing the physico-chemical conditions in the aqueous phase to reduce the solubility of the complex in the aqueous phase.

96. The method of item 95, wherein the changing of the physico-chemical conditions comprises adjusting the pH to between 2 to 6 preferably to between 3 to 6, optionally between 3.5 to 5.5, optionally between 4.0 to 5.0

97. The method of item 96, wherein the changing of the physico-chemical conditions comprises adjusting the pH to between 3.5 to 4.

98. The method of item 96, wherein the changing of the physico-chemical conditions comprises adjusting the pH to between 5 to 6.

99. The method of item 95, wherein the changing of the physico-chemical conditions comprises adjusting the conductivity, optionally by adding salts such as sodium chloride or calcium chloride.

100. The method of item 95, wherein the changing of the physico-chemical conditions comprises adding an organic solvent to the aqueous phase, optionally ethanol.

101. The method of item 95, wherein the changing of the physico-chemical conditions comprises adjusting the temperature.

102. The method of any preceding items, wherein the precipitated complex is separated from the aqueous supernatant phase by a mechanical separation process selected from one or more of membrane separation and centrifugal separation.

103. The method of item 102, wherein the membrane separation process is a continuous membrane separation process, optionally a cross flow, a dynamic or a tangential flow membrane separation process.

104. The method of item 102 or 103, wherein the membrane separation process comprise use of a membrane module selected from one or more of tubular membranes, hollow fibre membranes, spiral wound membranes and plate and frame membranes.

105. The method of item 102 to 104, wherein the membrane comprises a material selected from one or more of ceramics, metal, artificial polymer and natural polymer.

106. The method of item 105, wherein the membrane is a polyether sulfone membrane or an esterified cellulose membrane.

107. The method of item 104, wherein the membrane module is a hollow fibre membrane and wherein the separation process is performed at the following conditions:
pH of the aqueous phase of between 2 to 6.
Feed pressure of between 9 to 15 psi
Backwash pressure of between 9 to 15 psi.
Temperature of the aqueous phase of between 5° C. to 30° C.

108. The method of item 104, wherein the membrane module is a spiral wound membrane and wherein the separation process is performed at the following conditions:
pH of the aqueous phase of between 2 to 6.
Feed pressure of less than 120 psi
Backwash pressure of between 20 to 40 psi.
Temperature of the aqueous phase of between 5° C. to 45° C.

109. The method of item 104, wherein the membrane module is a ceramic tubular membrane and wherein the separation process is performed at the following conditions:
pH of the aqueous phase of between 3 to 7.
Feed pressure of 60 to 100 psi
Backwash pressure of between 10 to 30 psi.
Temperature of the aqueous phase of between 5° C. to 40° C.

110. The method of item 102 to 109 further comprising a diafiltration step.

111. The method of item 102, wherein the complex is separated from aqueous supernatant phase by centrifugal separation.

112. The method of item 111, wherein the centrifugation is performed at an acceleration between 500 to 5000 G, optionally between 1000 to 4000 G, optionally between 1500 to 3000 G.

113. The method of items 111 or 112, wherein the centrifugal separation is performed by a centrifuge or a liquid cyclone separator.

114. The method of item 113, wherein the centrifugation is a continuous process and the retention time is less than 30 min, optionally less than 15 min, optionally less than 10 min, optionally less than 5 min, optionally less than 3 min, optionally less than 2 min.

115. The method of item 114, wherein the flow rate to the centrifuge is more than 50 L/min, optionally more than 100 L/min, optionally more than 200 L/min, optionally more than 300 L/min, optionally more than 400 L/min, optionally more than 500 L/min, optionally between 50 to 1000 L/min, optionally between 100-750 L/min, optionally between 75 to 400 L/min.

116. The method of items 111 or 112, wherein the liquid cyclone separator is a multistage separator comprising at least two serial hydrocyclones, optionally at least three serial hydrocyclones, optionally at least four serial hydrocyclones.

117. The method of item 102 to 116, wherein the mechanical separation process is capable of retaining compounds having a size of more than 50 kDa, optionally having a size of more than 75 kDa, optionally having a size of more than 100 kDa, optionally having a size of more than 125 kDa, optionally having a size of more than 150 kDa.

118. The method of item 2, further comprising mixing the precipitated complex with a substance capable of extracting one or more compounds selected from PA, PI, LipO, PPO, glycoalkaloid and phenolic compounds from the complex and isolating the one or more compounds selected from PA, PI, LipO, PPO, glycoalkaloid and phenolic compounds by a mechanical separation process concentrating the one or more compounds selected from PA, PI, LipO, PPO, glycoalkaloid and phenolic compounds in the retentate.

119. The method of item 118, wherein the substance is an aqueous solvent.

120. The method of item 119, wherein the aqueous solvent has an increased pH and optionally an increased conductivity compared to the aqueous supernatant phase from which the complex separated.

121. The method of item 120, wherein the aqueous solvent has a pH between 7 to 14 and optionally a conductivity between 10 mS/cm to 200 mS/cm.

122. The method of item 118, wherein the substance is a solid substance increasing the pH in the isolated complex.

123. The method of item 122, wherein the solid substance is selected from one or more of oxides, hydroxides, phosphates, carboxylates and ammonia, optionally in the form of salts of ammonium or metals, such as sodium, potassium, calcium, magnesium.

124. The method of items 118 to 123, wherein the mechanical separation process is a process of items 102 to 117.

125. The method of any preceding items, further comprising at least one step of selective elution.

126. The method of item 125, wherein the selective elution step releases one or more compounds associated with the isolated complex, optionally by entrapment, by being bound to a moiety of the ligand or complexed compound or by being comprised in liquid remaining in the complex.

127. The method of items 125 to 126, wherein the released compound is selected from one or more of glycoalkaloid, phenolic compounds, PPO, PA, LipO, PI and the ligand.

128. The method of items 125 to 126, wherein the released compound is selected from one or more of glycoalkaloid, LipO, phenolic compounds, PPO and the ligand.

129. The method of items 125 to 127, wherein the released compound is selected from one or more of PA and PI.

130. The method of items 125 to 127, wherein the released compound is selected from one or more of PPO, PA and PI.

131. The method of items 125 to 130 wherein the selective elution is performed by contacting the isolated complex with a solvent which releases the one or more compounds.

132. The method of items 131, wherein the solvent is an aqueous solvent, optionally wherein conditions are selected from pH 1 to pH 6 and a conductivity between 1 mS/cm to 300 mS/cm optionally from pH 2 and a conductivity between 10 mS/cm to 200 mS/cm, optionally from pH 3 to pH 4.5 and a conductivity between 50 mS/cm and 100 mS/cm, optionally from pH 4.6 to pH 5 and a conductivity between 25 mS/cm to 250 mS/cm.

133. The method of items 131 to 132, wherein the solvent comprise an organic solvent selected from one or more of alcohols, glycols, esters, ethers, amines, aromatic acids, alkyl acids such as methanol, ethanol, propanol, polyethylene glycol, (PEG), propylene glycol (PG), monopropylene glycol (MPG), glycerol, benzoic acid, hexanoic acid, octanoic acid and derivatives of these.

134. The method of item 131 to 133, wherein the solvent comprise a surfactant selected from one or more of non-ionic surfactants, anionic surfactants, cationic surfactants, zwitterionic or amphoteric surfactants.

135. The method of item 134, wherein the surfactant is selected from one or more of sodium dodecyl sulphate, Tween 20, cetyl trimethyl ammonium bromide.

136. The method of item 131, wherein the eluted compound is PI and the solvent is an aqueous solution of sodium chloride at a concentration between 0.2 M to 2 M, optionally a concentration between 0.3 M to 1 M, optionally a concentration between 0.4 M to 0.8 M, optionally a concentration between 0.45 M to 0.65 M.

137. The method of items 131 to 136 wherein the aqueous solvent further comprises a buffer having a pH between pH 1 to pH 4.5, optimally a pH between 2 to pH 4.0, optionally a pH between pH 2.5 to pH 3.6.

138. The method of items 131 to 137, wherein the buffer is selected from one or more of acetate, citrate, sulphate, phosphate.

139. The method of items 131 to 138, wherein the aqueous solvent comprises a salt, optionally selected from alkali or earth alkali metal salts of chloride, nitrate, nitrite sulphate, sulphite, phosphate, acetate or citrate.

140. The method of any preceding items, further comprising subjecting the isolated compound(s) to microbial control step.

141. The method of item 140, wherein the microbial control step comprises adding an agent selected from bactericidal agents, bacteriostatic agent, fungicidal agents and fungistatic agents.

142. The method of item 140, wherein the microbial control step comprises one or more operations selected from heating, irradiating and filtering.

143. The method of any preceding items, further comprising a step of separating the compound selected from one or more of PA, PI, LipO and PPO from the ligand.

144. The method of any preceding items, further comprising a step of, optionally irreversibly, inactivating the one or more of PA, PI, LipO and PPO.

145. The method of item 144, wherein the one or more of PA, PI, LipO and PPO is inactivated by denaturation, optionally thermal or solvent denaturation.

146. The method of any preceding items, further comprising forming the isolated compound(s) into a formulation selected from powders, pastes, slurries or liquids.

147. The method of item 146, wherein the formulation is a powder selected from a dried product, a spray dried product, a prilled product, a layered product, an absorbed core product, an extruded product and a mixer granulated product.

148. The method of items 146 or 147, wherein the water activity, aw, of the formulation is below 0.9, optionally below 0.7, optionally below 0.6.

149. The method of items 146 to 148, comprising reducing the water activity by adding a mono- or disaccharide to the formulation.

150. The method of item 149, wherein the mono- or disaccharide is selected from one or more of glucose, fructose, sucrose and lactose.

151. The method of items 146 to 148, wherein the water activity is reduced by adding a dextrin derived from starch.

152. The method of any preceding items, further comprising stabilising the one or more of PA, PI, LipO and PPO by adding a protein stabilizing agent, optionally selected from one or more antioxidants, reducing agents, PVP, PVA and PEG.

153. The method of any preceding items, wherein the formation of the complex is carried out in an, optionally thermos controlled, and agitated reactor having a volume of at least 500 L, optionally at least 1000 L, optionally at least 4000 L, optionally at least 8000 L optionally at least 15000 L optionally at least 25000 L.

154. The method of item 153, wherein the reactor is a continuous reactor or a batch reactor.

155. The method of items 153 to 154, wherein the agitation is selected from stirring, shaking, rotation, pumping and vibrating.

156. The method of items 153 to 155, wherein the thermal control includes a heating source selected from steam, electricity and fuel and optionally a cooling source selected from liquid or gas cooling.

157. The method of any preceding item wherein a compound selected in the first group is deselected in the second group.

158. The method of any preceding item, wherein the aqueous phase of step a) comprises a compound selected from one or more of PA, PI, PPO and a compound selected from one or more of glycoalkaloid, LipO and phenolic compounds.

159. A method for isolating one or more of glycoalkaloid, LipO and phenolic compounds said method comprising:
  a) providing an aqueous phase comprising one or more of glycoalkaloid, LipO and phenolic compounds and at least one protein;
  b) contacting the aqueous phase with a mobile solubilized ligand at physico-chemical conditions allowing formation of a complex between the ligand and the protein;
  c) allowing the complex to separate from the aqueous supernatant phase, optionally by changing said physico-chemical conditions in the composition to reduce the solubility of the complex; and
  d) isolating the one or more of glycoalkaloid, LipO and phenolic compounds comprised in the aqueous phase from the complex.

160. A method for isolating one or more of glycoalkaloid, LipO and phenolic compounds said method comprising:
  a) providing an aqueous phase comprising one or more of glycoalkaloid LipO and phenolic compounds and at least one protein;
  b) contacting the aqueous phase with a mobile solubilized ligand at physico-chemical conditions allowing formation of a complex between the ligand and the one or more of glycoalkaloid, LipO and phenolic compounds;
  c) allowing the complex to separate from the aqueous supernatant phase, optionally by changing said physico-chemical conditions in the composition to reduce the solubility of the complex; and
  d) isolating the one or more of glycoalkaloid, LipO and phenolic compounds comprised in the complex.

161. The method of items 159 or 160, wherein the mobile solubilized ligand is selected from one or more of silicates and silicones.

162. A composition comprising one or more of patatin protein (PA), protease inhibitor protein (PI), lipoxygenase (UK)), polyphenol oxidase (PPO), glycoalkaloid and phenolic compounds obtainable from the method of items 1 to 158.

163. The composition of item 162, comprising one or more of lipoxygenase (LipO), glycoalkaloid and phenolic compounds.

164. The composition of item 162, comprising one or more of PA, PI and PPO.

165. The composition of item 162, further comprising the ligand of items 49 to 54.

166. The composition of item 166, comprising at least 25%, optionally at least 50%, optionally at least 75% of the polymer contained in the complex of item 1.

167. The composition of item 162, wherein the composition is an additive for one or more of foods, animal feeds, pet foods, beverages, cosmetics, pharmaceuticals, nutraceuticals, dietary supplements and fermentations.

168. The composition of item 167, wherein the additive is an additive to a food or beverage selected from one or more of meats, confectionary, bread, dairy, ready-to-eat food and sports food and drinks.

169. The composition of item 167, wherein the additive is an additive to animal feed selected from poultry feed, ruminants feed, pig feed, horse feed, fish feed and insect feed.

170. The composition of item 167, wherein the additive is an additive to a pet food selected from canine or feline pet foods.

171. The composition of item 167, wherein the additive is an additive to a cosmetic selected from lotions, creams, gels, ointments, soaps, shampoos, conditioners, antiperspirants, deodorants, mouth wash, contact lens products and foot bath products.

172. The composition of item 167, wherein the additive is an additive to a nutraceutical.

173. The composition of item 167, wherein the additive is an additive to is an additive to a dietary supplement, optionally to a protein supplement or to a senior nutrition product.

174. The composition of item 167, wherein the additive is an additive to a fermentation selected from a bacterial fermentation, a fungal fermentation or a yeast fermentation.

175. The composition of items 162 to 166, wherein the composition is a food or beverage composition 176. The composition of items 162 to 166, wherein the composition is an animal feed composition.

177. The composition of items 162 to 166, wherein the composition is a pet food composition.

178. The composition of items 162 to 166, wherein the composition is a cosmetic composition.

179. The composition of item 178, wherein the cosmetic composition is a composition comprising glycoalkaloid, optionally for use as an exfoliant.

180. The composition of items 162 to 166, wherein the composition is a pharmaceutical composition.

181. The composition of item 180, wherein the pharmaceutical composition is a composition comprising glycoalkaloid for use as a medicament.

182. The composition of item 181 for use as a medicament for treating cancer.

183. The composition of items 162 to 166, wherein the composition is a nutraceutical composition.

184. The composition of items 162 to 166, wherein the composition is a dietary supplement.

185. The composition of items 162 to 166, wherein the composition is a fermentation broth.

186. A composition, comprising a natural or synthetic polymer having aromatic or heteroaromatic acid ligands covalently attached.

187. The composition of item 186, wherein the polymer is soluble in aqueous solvent above pH 6.

188. The composition of items 186 or 187, wherein the polymer is insoluble below pH 5.9. optionally below pH 5.5, optionally below pH 5.0, optionally below pH 4.8, optionally below pH 4.5, optionally below pH 4.2, optionally below pH 4.0, optionally below pH 3.5

189. The composition of items 186 to 188, wherein the polymer is a soluble starch reacted with a bifunctional reagent for attachment of the ligands 190. The composition of item 189, wherein the bifunctional reagent is chosen from one or more of epichlorohydrin, allyldiglycidyl ether, allyl bromide and divinyl sulfone.

191. The composition of item 186 to 190, wherein the aromatic or heteroaromatic acid is chosen from the group of hydroxybenzoic acid, aminobenzoic acid, mercaptobenzoic acid and derivatives hereof.

192. A container comprising a composition or a product of any of items 162 to 191.

193. Use of the composition of item 162 to 174, in a process for providing one or more functions selected from foam control, emulsion control, control of proteolytic activity, nutrition, gelation, solubility, organoleptic improvement, allergenicity reduction and oxidation.

194. A method for isolating one or more proteins comprising contacting a composition, optionally an aqueous composition, comprising the one or more proteins with a water-soluble silicon containing anionic polymer capable of binding to the protein; optionally adjusting the conditions in the composition to promote binding between the protein(s) and the polymer and causing the bound proteins to separate from the composition, optionally by precipitation and isolating the separated bound protein(s), optionally comprising one or more selective elution steps to achieve one or more isolated protein fractions, optionally separated from the polymer.

195. The method of item 194, wherein the polymer is a solubilized silicon containing anionic polymer.

196. The method of item 194, wherein the polymer is dissolved in the aqueous composition under conditions that does not lead to formation of substantial amounts of separated proteins until the conditions have been adjusted to effect separation.

197. The method of item 196, wherein the polymer is dissolved in the aqueous composition at pH 7 or higher, optionally at pH 8 or higher, optionally at pH 9 or higher, optionally at pH 10 or higher.

198. The method of items 194 to 197, wherein precipitation of protein bound to the silicon containing polymer is caused by adjusting pH to below pH 8, optionally to below 7, optionally to below pH 6.5, optionally to a pH between 1 to 9, optionally to a pH between 2 to 8, optionally to a pH between 3 to 7, optionally to a pH between 3.5 to 6.5, optionally to a pH between 4.5 to 6.5, optionally to a pH between 5.5 to 6.5.

199. The method of items 194 to 198, wherein the polymer is a silicate, optionally a metal silicate.

200. The method of item 199, wherein the silicate is selected from the group of sodium silicate, potassium silicate, ammonium silicates, quaternary ammonium silicates and mixtures of these.

201. The method of item 200, wherein the silicate is a water glass (sodium metasilicate).

202. The method of items 194 to 198, wherein the silicon containing polymer comprise silicone moieties, optionally in a mixture with silicates.

203. The method of item 202, wherein the silicone moieties comprise an organic functional group capable of binding to proteins.

204. The method of item 202, wherein the organic functional group comprise a hydrophobic group such as a C2-C12 branched or un-branched alkyl group, an aromatic or heteroaromatic ring system or a combination of these.

205. The method of item 202, wherein the organic functional group comprise one or more anionic groups, one or more cationic groups or a combination of these.

206. The method of items 202 to 205, wherein the silicone moieties are derived from the a reactive silane, optionally glycidoxypropyl or allyl silane, optionally 3-glycidoxypropyldimethoxymethylsilane, 3-glycidoxypropyldimethylethoxysilane, (3-glycidyloxypropyl)trimethoxysilane, allyltrimethoxysilane, allyltriethoxysilane.

207. The method of items 202 to 206, wherein the silicone moieties are mixed with silicates in a molar ratio silicone:silicate in the range of 0.001 to 0.99, optionally 0.01 to 0.90, optionally 0.02 to 0.8, optionally 0.03 to 0.7, optionally 0.05 to 0.6, optionally 0.07 to 0.5, optionally 0.1 to 0.4, optionally 0.05 to 0.30, optionally 0.1 to 0.2.

208. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
   a) providing an aqueous phase comprising compounds selected from two or more of PA, PI, PPO, LipO, pectin, lipid, glycoalkaloid and phenolic compounds of which at least one compound is selected from PA, PI, LipO and PPO;
   b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1;
   c) contacting the remaining aqueous phase with a mobile solubilized ligand at physico-chemical conditions allowing formation of a complex between the ligand and the compounds selected from one or more of PA, PI, LipO and PPO;
   d) allowing the complex to separate from the aqueous supernatant phase, optionally by changing said physico-chemical conditions in the composition to reduce the solubility of the complex; and
   e) isolating the complex separated from the aqueous phase.

209. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
   a) providing an aqueous phase comprising compounds selected from two or more of PA, PI, PPO, LipO, pectin, lipid, glycoalkaloid and phenolic compounds of which at least one compound is selected from PA, PI, LipO and PPO;
   b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1;

f) adjusting pH of the remaining aqueous phase (from step b)) to allow the formation of a precipitate comprising PA; and g) isolating the precipitate from the aqueous phase.

210. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1; and
  h) subjecting the remaining aqueous phase (from step b)) to a membrane filtration process separating at least one of PA and PI in the retentate from at least one of PA, PI, LipO, PPO, pectin, lipid, glycoalkaloid and phenolic compounds in the permeate.

211. A method for reducing turbidity of an aqueous phase comprising compounds selected from two or more of PA, PI, PPO, LipO, pectin, lipid, glycoalkaloid and phenolic compounds of which at least one compound is selected from PA, PI, LipO and PPO;
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) contacting the aqueous phase with a soluble silicate at a pH in the range of 3-10 and optionally, a divalent or trivalent metal ion allowing formation of an insoluble precipitate comprising said silicate and one or more the compounds selected from LipO, PPO, pectin, lipid, glycoalkaloid and phenolic compounds, and optionally, a divalent or trivalent metal ion, said insoluble precipitate is subsequently removed from the aqueous phase by physical means;
thereby obtaining an aqueous phase having reduced turbidity compared to an untreated aqueous phase.

212. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) contacting the aqueous phase with a soluble silicate at a pH, in the range of 3-10 and optionally, a divalent or trivalent metal ion allowing formation of an insoluble precipitate comprising said silicate and one or more the compounds selected from LipO, PPO, pectin, lipid, glycoalkaloid and phenolic compounds, and optionally, a divalent or trivalent metal ion, said insoluble precipitate is subsequently removed from the aqueous phase by physical means;
  c) contacting the remaining aqueous phase with a mobile solubilized ligand at physico-chemical conditions allowing formation of a complex between the ligand and the compounds selected from one or more of PA, PI, LipO and PPO;
  d) allowing the complex to separate from the aqueous supernatant phase, optionally by changing said physico-chemical conditions in the composition to reduce the solubility of the complex; and
  e) isolating the complex separated from the aqueous phase.
OR
  f) adjusting pH of the remaining aqueous phase (from step b)) to allow the formation of a precipitate comprising PA;
  g) isolating the precipitate from the aqueous phase
OR
  h) subjecting the remaining aqueous phase (from step b)) to a membrane filtration process separating at least one of PA and PI in the retentate from at least one of PA, PI, LipO, PPO, pectin, lipid, glycoalkaloid and phenolic compounds in the permeate 213. A method according to any of claims 211-212, wherein the silicate concentration is in the range of 0.2-5 g/L, preferably in the range of 0.5-3 g/L 214. A method according to any of claims 211-213, wherein silicate is sodium silicate.

215. A method according to any of claims 211-214, wherein the concentration of the divalent or trivalent metal ion in the aqueous phase is between 2-100 mM, preferably in the range of 5-25 mM 216. A method according to any of claims 211-215, wherein the divalent or trivalent metal ion is a calcium, magnesium or aluminum ion.

217. A method according to any of claims 211-215, wherein the physical means in step b) is centrifugation and the supernatant is subsequently removed.

218. A method according to claim 217, wherein the precipitate is washed by resuspension in water and pH adjusted to 3.0 with hydrochloric acid and centrifuged and the supernatant removed.

219. A method according to claim 218, wherein the washed precipitate is suspended in water and pH is slowly adjusted to pH 7-10 with 1 M NaOH.

220. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1;

c) contacting the remaining aqueous phase with a mobile solubilized ligand at physico-chemical conditions allowing formation of a complex between the ligand and the compounds selected from one or more of PA, PI, LipO and PPO;

d) allowing the complex to separate from the aqueous supernatant phase, optionally by changing said physico-chemical conditions in the composition to reduce the solubility of the complex; and e) isolating the complex separated from the aqueous phase.

221. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1;

f) adjusting pH of the remaining aqueous phase (from step b)) to allow the formation of a precipitate comprising PA; and g) isolating the precipitate from the aqueous phase.

222. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) performing one or more steps to reduce the concentration of solanine in the dry matter of the aqueous phase with at least 15 percent, such as at least 20%, such as at least 25% and to achieve an optical density at 620 nm of the remaining aqueous phase of less than 0.7; such as less than 0.5; such as less than 0.3; such as less than 0.2; such as less than 0.1; and h) subjecting the remaining aqueous phase (from step b)) to a membrane filtration process separating at least one of PA and PI in the retentate from at least one of PA, PI, LipO, PPO, pectin, lipid, glycoalkaloid and phenolic compounds in the permeate.

223. A method according to any of claims 211-222, wherein the pH of the aqueous phase in step b) is adjusted to a pH in the range of 5-9, preferably in the range of 6-8.

224. A method according to any of claims 211-223, wherein the formation of an insoluble precipitate in step b) is made by incubating the aqueous phase for less than 120 min, preferably less than 60 min, preferably less than 30 min, preferably less than 15 min.

225. A method according to any of claims 211-224, wherein the formation of an insoluble precipitate in step b) is made by incubating the aqueous phase at 15-50° C., preferably at 20-45° C., preferably at 22-40° C., preferably at 25-35° C.

226. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising a) providing an aqueous phase comprising compounds selected from two or more of PA, PI, PPO, LipO, pectin, lipid, glycoalkaloid and phenolic compounds of which at least one compound is selected from PA, PI, LipO and PPO;

b) adjusting pH of the aqueous phase to allow the formation of a precipitate comprising at least 10% of the PA initially present in the aqueous phase and to achieve an optical density at 620 nm of the remaining aqueous phase of less than 0.7;

c) isolating the precipitate from the aqueous phase d) isolating PI from the remaining aqueous phase (from step c)).

227. The method according to claim 226, wherein the optical density at 620 nm of the remaining aqueous phase in step b) is less than 0.5; such as less than 0.3; such as less than 0.2; such as less than 0.1; such as less than 0.07

228. The method according to claims 226-227, wherein the concentration of solanine in the dry matter of the remaining aqueous phase in step b) reduced with at least 5 percent.

229. The method according to claims 226-228, wherein the aqueous phase in step a) is potato fruit juice obtained from industrial manufacture of potato starch.

230. The method according to claims 226-229, wherein the fruit juice is further treated in a defoamer to substantially reduce the amount of foam in the fruit juice.

231. The method according to claims 226-230, wherein the fruit juice has been treated to substantially reduce the amount of insoluble substances in the fruit juice prior to pH adjustment in step b)

232. The method according to claims 226-231, wherein the pH adjustment in step b) is performed less than 200 minutes after the fruit juice has been released from the potatoes, such as less than 150 minutes, such as less than 100 minutes, such as less than 60 minutes, such as less than 30 minutes, such as less than 20 minutes, such as less than 10 minutes, such as less than 5 minutes after the fruit juice has been released from the potatoes.

233. The method according to claims 226-232, wherein the fruit juice is pH adjusted by an in-line mixing with an acid.

234. The method according to claims 226-233, wherein the fruit juice has been added an antioxidant, such as sodium bisulfite or sodium sulfite.

235. The method according to claims 226-234, wherein the fruit juice has a total true protein concentration of at least 5 g/L such at least 6 g/L, such as at least 7 g/L, such as at least 8 g/L fruit juice.

236. The method according to claims 226-235, wherein the aqueous phase in step b) is adjusted to a pH below pH 5.5, such as below pH 5.0, such as below pH 4.5, such as below pH 4.0

237. The method according to claims 226-236, wherein the aqueous phase in step b) is adjusted to a pH in the range of pH 1-5.5, such as in the range of pH 1.5-5.0, such as in the range of 2.0-4.5, such as in the range of pH 2.0-3.8, such as in the range of pH 2.5-3.5.

238. The method according to claims 226-237, wherein the aqueous phase in step b) is adjusted to a pH in the range of pH 3.0-5.0, such as in the range of pH 3.0-4.5, such as in the range of pH 3.3-4.2, whereby Lipoxygenase in the resulting precipitate is separated from PI in the remaining aqueous phase.

239. The method according to claims 226-238, wherein the aqueous phase in step b) has a temperature in the range of 20-62 degrees Celsius, such as in the range of 24-48 degrees Celsius, such as in the range of 30-45 degrees Celsius, such as in the range of 35-45 degrees Celsius, such as in the range of 41-60 degrees Celcius, such as in the range of 45-58 degrees Celcius, such as in the range of 48-58 degrees Celcius.

240. The method according to claims 226-239, wherein the precipitate in step b) comprise at least 10% of the PA initially present in the aqueous phase, such as at least 20%, such as at least 30%, such as at least 50%, such as at least 70%, such as at least 85%, such as at least 90% of the PA initially present in the aqueous phase.

241. The method according to claims 226-240, wherein the isolation of the precipitate from the aqueous phase in step c is performed using a decanter centrifuge.

242. The method according to claims 226-241, wherein the isolated precipitate in step c) is further treated to produce a protein powder as an animal feed product. In one embodiment, the precipitate is washed with an aqueous solution of an acid and dried.

243. The method according to claims 226-242, wherein the optimal business model for utilizing potato fruit juice is the combined production of a PA product not intended for use as a functional protein and a highly functional PI product, rather than the production of both a functional PA and a functional PI product.

244. The method according to claims 226-243, wherein the isolated precipitate in step c) contains less than 50%, such as less than 40%, such as less than 30%, such as less than 20%, such as less than 10% functional PA.

245. The method according to claims 226-244, wherein the isolated precipitate in step c) contains less than 50%, such as less than 40%, such as less than 30%, such as less than 20%, such as less than 10% PA being soluble by suspension of the precipitate in an aqueous phosphate buffer at 2% dry matter and at pH 7.0.

246. The method according to claims 226-245, wherein the isolated precipitate in step c) is further treated to produce a protein powder as a human nutritional food product. In one embodiment, the precipitate is washed with an aqueous solution of an acid and dried.

247. The method according to claims 226-246, wherein the isolated precipitate in step c) is further treated to produce a protein powder as a human functional protein ingredient product. In one embodiment, the precipitate is washed with an aqueous solution of an acid and dried.

248. The method according to claims 226-247, wherein the isolated precipitate in step c) is dissolved by adjusting pH to a pH above pH 5 such as a pH above pH 6, such as a pH above 7 such as a pH in the range of pH 5-10, such as a pH in the range of 6-9, such as a pH in the range of pH 6.5-8.5.

249. The method according to claims 226-248, wherein the dissolved precipitate is treated to further increase the purity of the PA.

250. The method according to claims 226-249, wherein the dissolved precipitate is clarified by centrifugation and/or filtration 251. The method according to claims 226-250, wherein the dissolved precipitate is added a soluble silicate and pH adjusted (if necessary) to achieve the precipitation of unwanted impurities.

252. The method according to claims 226-251, wherein the dissolved precipitate is added a divalent or trivalent metal ion and pH adjusted (if necessary) to achieve the precipitation of unwanted impurities.

253. The method according to claims 226-252, wherein the dissolved precipitate is treated with a solid phase adsorbent to adsorb unwanted impurities.

254. The method according to claims 226-253, wherein the dissolved precipitate is treated with a solid phase adsorbent to adsorb glycoalkaloids and/or phenolic compounds.

255. The method according to claims 226-254, wherein the dissolved precipitate is subjected to a membrane filtration process to separate PA in the retentate from unwanted impurities in the permeate 256. The method according to claims 226-255, wherein the membrane filtration process is a tangential flow ultrafiltration process employing a membrane having a nominal pore size in the range of approx. 10,000-200,000 kDa, such as in the range of approx. 30,000-150,000 kDa, such as in the range of approx. 50,000-100,000 kDa 257. The method according to claims 226-256, wherein the isolation of PI in step d) above comprise subjecting the remaining aqueous phase to a solid phase adsorption step thereby adsorbing the PI and separating it from the aqueous phase.

258. The method according to claims 226-257, wherein the phase adsorption is performed using an adsorbent having negatively charged ligands such as ion exchanging ligands including carboxylic acid, sulfonic acid and phosphonic acid ligands.

259. The method according to claims 226-258, wherein the solid phase adsorption is performed using an adsorbent having aromatic acid ligands attached thereto.

260. The method according to claims 226-259, wherein the solid phase adsorbent comprises a benzoic acid, a carboxymethyl benzene, a benzene sulfonic acid or a (sulfomethyl) benzene ligand or derivatives hereof.

261. The method according to claims 226-260, wherein the isolation of PI in step d) above comprise subjecting the remaining aqueous phase to a membrane filtration process separating PI in the retentate from at least one of lipid, glycoalkaloid and phenolic compounds in the permeate.

262. The method according to claims 226-261, wherein said membrane filtration process is a tangential flow ultrafiltration process.

263. The method according to claims 226-262, wherein said ultrafiltration process is performed using a membrane having a nominal pore size (cut-off value) of less than 50,000 D, such as less than 30,000 D. In one embodiment, the membrane has a nominal pore size of about 10,000 D.

264. The method according to claims 226-263, wherein the ultrafiltration process is performed at a pH value in the range of pH 1-6, such as pH 1.5-5.0, such as pH 2.0-4.5, such as pH 2.5-4.0 such as pH 3.0-4.0, such as pH 1.5-2.5.

265. The method according to claims 226-264, wherein the PI isolated in step d) contains less than 0.30 g PA per PI, such as less than 0.20 g PA, such as less than 0.15 g PA, such as less than 0.10 g PA per g PI.

266. The method according to claims 226-265, wherein the PI isolated in step d) contains less than 200 ppm solanine, such as less than 100 ppm solanine such as less than 70 ppm solanine, such as less than 50 ppm solanine, such as less than 25 ppm solanine, such as less than 10 ppm solanine on a dry matter basis.

267. The method according to claims 226-266, wherein the PI isolated in step d) has a purity (N×6.25) corresponding to at least 70%, such as at least 75%, such as at least 80%, such as at least 85%, such as at least 90% PI on a dry matter basis.

268. The method according to claims 226-267, wherein the PI isolated in step d) constitutes more than 75%, such as more than 80%, such as more than 85%, such as, more than 90%, such as more than 95% of the PI present in the aqueous phase of step a)

269. The method according to claims 226-268, wherein the PI isolated in step d) contains less than 25%, such as less than 15%, such as less than 10%, such as less than 5%, such as less than 2% of the polyphenoloxidase activity present in the aqueous phase provided in step a) on a dry matter basis.

270. The method according to claims 226-269, wherein the ultrafiltration process is performed at a pH value in the range of pH 0.1-1.0, such as pH 0.5-0.9, 271. The method according to claims 226-270, wherein the isolation of PI in step d) comprise subjecting the remaining aqueous phase to a solid phase adsorption step thereby adsorbing glycoalkaloids and phenolic compounds and separating it from the aqueous phase.

272. The method according to claims 226-271, wherein the isolation of PI in step d) comprise subjecting the PI retentate after the ultration process to a solid phase adsorption step thereby adsorbing glycoalkaloids and phenolic compounds and separating it from the PI retentate.

273. The method according to claim 272, wherein the solid phase adsorption is performed by contacting the remaining aqueous phase or the PI retentate with a solid phase adsorbent selected from the group of activated carbon, layered silicate adsorbents and porous synthetic polymers.

274. The method according to claim 273, wherein the porous synthetic polymer is a hydrophobic adsorbent 275. The method according to claim 274, wherein the porous synthetic polymer is a hydrophobic adsorbent comprising a cross-linked aromatic backbone such as a cross-linked vinyl benzene backbone.

276. The method according to claim 275, wherein the porous synthetic polymer is a Dowex, Lewatit or Amberlite adsorbent.

277. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 15 percent, and to achieve an optical density at 620 nm of the remaining aqueous phase of less than 0.7;
  c) contacting the remaining aqueous phase with a mobile solubilized ligand at physico-chemical conditions allowing formation of a complex between the ligand and the compounds selected from one or more of PA, PI, LipO and PPO;
  d) allowing the complex to separate from the aqueous supernatant phase, optionally by changing said physico-chemical conditions in the composition to reduce the solubility of the complex; and
  e) isolating the complex separated from the aqueous phase.

278. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 15 percent, to achieve an optical density at 620 nm of the remaining aqueous phase of less than 0.7;
  f) adjusting pH of the remaining aqueous phase (from step b)) to allow the formation of a precipitate comprising PA; and
  g) isolating the precipitate from the aqueous phase.

279. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, pectin, lipid, glycoalkaloid and phenolic compounds said method comprising
  a) providing an aqueous phase comprising compounds selected from two or more of PA, PI, PPO, LipO, pectin, lipid, glycoalkaloid and phenolic compounds of which at least one compound is selected from PA, PI, LipO and PPO;
  b) performing one or more steps to reduce the concentration of solanine in the dry matter of the aqueous phase with at least 15 percent, to achieve an optical density at 620 nm of the remaining aqueous phase of less than 0.7; and
  h) subjecting the remaining aqueous phase (from step b)) to a membrane filtration process separating at least one of PA and PI in the retentate from at least one of PA, PI, LipO, PPO, pectin, lipid, glycoalkaloid and phenolic compounds in the permeate.

280. The method according to any one of claims 277-279, wherein the concentration of solanine in the dry matter of the aqueous phase reduced with at least 20%, such as at least 25%.

281. The method according to any one of claims 277-280, wherein the optical density at 620 nm of the remaining aqueous phase of less than less than 0.5. The optical density may be less than 0.3. The optical density may be less than 0.2. The optical density may be less than 0.1.

282. The method according to any one of claims 277-281, wherein the reduction of the concentration of solanine in step b) can be done by changing the physico-chemical conditions by any of the methods mentioned herein, including contacting the aqueous phase with soluble silicate.

283. The method according to any one of claims 277-282, wherein the reduction of the concentration of solanine (step b) and to achieving an optical density at 620 nm of the remaining phase the result of two or more independent steps.

284. The method according to any one of claims 277-283, wherein the reduction of the concentration of solanine (step b) and achieving an optical density at 620 nm of the remaining phase is the result of a single step.

285. The method according to any one of claims 277-284, wherein the one or more steps needed to achieve the reduction of the concentration of solanine (step b) and achieving an optical density at 620 nm of the remaining phase can comprise any of the procedures for reducing turbidity mentioned herein, for example a combined step with treatment using silicate and calcium.

286. The method according to any one of claims 1-285, wherein step b) does not comprise the addition of an acrylic polymer.

The invention claimed is:

1. A method for isolating a first group of compounds selected from one or more of patatin protein (PA), protease inhibitor protein (PI), lipoxygenase (LipO) and polyphenol oxidase (PPO) from a second group of compounds selected from one or more of PA, PI, LipO, PPO, glycoalkaloid and phenolic compounds, said method comprising:
 a) providing an aqueous phase comprising compounds selected from two or more of PA, PI, PPO, LipO, glycoalkaloid and phenolic compounds of which at least one compound is selected from one or more of PA, PI, LipO and PPO;
 b) contacting the aqueous phase with a mobile solubilized ligand at physico-chemical conditions allowing formation of a complex between the ligand and the compounds selected from one or more of PA, PI, LipO and PPO;
 c) allowing the complex to separate from the aqueous supernatant phase, optionally by changing said physico-chemical conditions in the composition to reduce the stability of the complex; and
 d) isolating the complex separated from the aqueous supernatant phase by precipitation.

2. The method of claim 1, wherein the separated complex comprises a combination of PA and PI and PPO and wherein the complex separates from the aqueous supernatant phase by precipitation.

3. The method of claim 2, wherein the dry weight ratio PA:PI in the precipitate is higher than the dry weight PA:PI ratio for PA and PI remaining dissolved in the aqueous supernatant phase.

4. The method of claim 3, further comprising dissolving the precipitated complex of step d) in an aqueous solvent and isolating PA from one or more compounds selected from PI and PPO by a mechanical separation process concentrating the PA in the retentate.

5. The method of claim 3, further comprising isolating the precipitated complex by a mechanical separation process concentrating one or more of PA, PI and PPO in the retentate.

6. The method of claim 3, further comprising:
 a) contacting the aqueous supernatant phase with a further mobile solubilized ligand at physico-chemical conditions in the aqueous supernatant phase allowing formation of a complex between the ligand and compounds selected from one or more of PI, and PPO;
 b) allowing the complex to separate from the aqueous supernatant phase, optionally by changing the physico-chemical conditions in the composition to reduce the solubility of the complex so that the complex separates from the aqueous supernatant phase; and
 c) isolating the complex.

7. The method of claim 2, wherein the sum of PA and PI remaining dissolved in the aqueous supernatant phase is less than 20%, optionally less than 10 wt. % of the total PA and PI.

8. The method of claim 7, further comprising dissolving the precipitated complex in an aqueous solvent and isolating PA from one or more compounds selected from PI, and PPO by a mechanical separation process concentrating the PA in the retentate.

9. The method of claim 7, further comprising isolating the precipitated complex by mechanical separation process concentrating the one or more or PA, PI, and PPO in the retentate.

10. The method of claim 2, wherein the dry weight ratios PI:PA or PPO:PA in the precipitate is higher than the dry weight ratios PI:PA or PPO:PA for PA, Pi and PPO remaining dissolved in the aqueous supernatant phase.

11. The method of claim 10, further comprising concentrating PA in the aqueous supernatant phase by mechanical separation process concentrating PA in the retentate, optionally combined with diafiltration.

12. The method of claim 10 further comprising:
 a) contacting the aqueous supernatant phase with a further mobile solubilized ligand at physico-chemical conditions in aqueous supernatant phase allowing formation of a complex between the ligand and PA;
 b) allowing the complex to separate from the aqueous supernatant phase, optionally by changing said physico-chemical conditions in the composition to reduce the solubility of the complex so that the complex separates from the aqueous supernatant phase; and
 c) isolating the complex.

13. The method of claim 10, further comprising adsorbing dissolved PA in the aqueous supernatant phase on an immobilized solid carrier at conditions where the carrier will bind PA.

14. The method of claim 1, further comprising pre-treating the aqueous phase of a) by absorbing one or more of PI, LipO and PPO on an immobilized solid carrier at conditions where the carrier will bind the one or more of PI, LipO or PPO.

15. The method of claim 1, wherein the PA is complexed to the ligand in a PA: ligand dry weight ratio of at least 4:1.

16. The method of claim 1, wherein the PI is complexed to the ligand in a PI: ligand dry weight ratio of at least 3:1.

17. The method of claim 1, wherein the PPO is complexed to the ligand in a PPO: ligand dry weight ratio of at least 2:1.

18. The method of claim 1, wherein the aqueous phase of step a) comprise an aqueous solution liberated when disintegrating a portion of a plant optionally a tuber portion of a plant of the genus *Solanum*, optionally of the species *S. tuberosum*.

19. A method for isolating one or more of glycoalkaloid, LipO and phenolic compounds said method comprising:
 a) providing an aqueous phase comprising one or more of glycoalkaloid, LipO and phenolic compounds and at least one protein;
 b) contacting the aqueous phase with a mobile solubilized ligand at physico-chemical conditions allowing formation of a complex between the ligand and the protein;
 c) allowing the complex to separate from the aqueous supernatant phase, optionally by changing said physico-chemical conditions in the composition to reduce the solubility of the complex; and d) isolating the one or more of glycoalkaloid, LipO and phenolic compounds comprised in the aqueous phase from the complex.

20. A method for isolating one or more of glycoalkaloid, LipO and phenolic compounds said method comprising:
   a) providing an aqueous phase comprising one or more of glycoalkaloid, LipO and phenolic compounds and at least one protein;
   b) contacting the aqueous phase with a mobile solubilized ligand at physico-chemical conditions allowing formation of a complex between the ligand and the one or more glycoalkaloid, LipO and phenolic compounds;
   c) allowing the complex to separate from the aqueous supernatant phase, optionally by changing said physico-chemical conditions in the composition to reduce the solubility of the complex; and
   d) isolating the one or more of glycoalkaloid, LipO and phenolic compounds comprised in the aqueous phase from the complex.

* * * * *

UNITED STATES PATENT AND TRADEMARK OFFICE
CERTIFICATE OF CORRECTION

PATENT NO. : 12,274,279 B2  
APPLICATION NO. : 18/079984  
DATED : April 15, 2025  
INVENTOR(S) : Allan Otto Fog Lihme et al.

Page 1 of 1

It is certified that error appears in the above-identified patent and that said Letters Patent is hereby corrected as shown below:

In the Claims

At Column 84, Line 19, "Pi" should be -- PI --.

Signed and Sealed this
Twenty-fifth Day of November, 2025

John A. Squires
*Director of the United States Patent and Trademark Office*